US010273496B2

(12) United States Patent
Peterhaensel et al.

(10) Patent No.: US 10,273,496 B2
(45) Date of Patent: Apr. 30, 2019

(54) PLANTS WITH IMPROVED PHOTOSYNTHETIC CARBON FIXATION CAPACITY

(71) Applicant: BASF SE, Ludwigshafen am Rhein (DE)

(72) Inventors: Christoph Peterhaensel, Paderborn (DE); Jeroen Van Rie, Merelbeke (BE); Claus Frohberg, Kleinmachnow (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/534,519

(22) PCT Filed: Dec. 14, 2015

(86) PCT No.: PCT/EP2015/079649
§ 371 (c)(1),
(2) Date: Jun. 9, 2017

(87) PCT Pub. No.: WO2016/096761
PCT Pub. Date: Jun. 23, 2016

(65) Prior Publication Data
US 2017/0327836 A1 Nov. 16, 2017

(30) Foreign Application Priority Data
Dec. 17, 2014 (EP) .................... 14198663

(51) Int. Cl.
C12N 15/82 (2006.01)
C12N 9/04 (2006.01)
C12N 9/16 (2006.01)

(52) U.S. Cl.
CPC ....... *C12N 15/8269* (2013.01); *C12N 9/0006* (2013.01); *C12N 9/16* (2013.01); *C12N 15/8261* (2013.01); *C12Y 101/99014* (2013.01); *C12Y 301/03011* (2013.01); *C12Y 301/03037* (2013.01); *Y02A 40/146* (2018.01)

(58) Field of Classification Search
None
See application file for complete search history.

(56) References Cited

U.S. PATENT DOCUMENTS

| | | |
|---|---|---|
| 5,004,863 A | 4/1991 | Umbeck |
| 5,159,135 A | 10/1992 | Umbeck |
| 5,188,642 A | 2/1993 | Shah et al. |
| 5,405,765 A | 4/1995 | Vasil et al. |
| 5,472,869 A | 12/1995 | Krzyzek et al. |
| 5,510,471 A | 4/1996 | Lebrun et al. |
| 5,538,877 A | 7/1996 | Lundquist et al. |
| 5,538,880 A | 7/1996 | Lundquist et al. |
| 5,550,318 A | 8/1996 | Adams et al. |
| 5,641,664 A | 6/1997 | D'Halluin et al. |
| 5,679,558 A | 10/1997 | Gobel et al. |
| 5,736,369 A | 4/1998 | Bowen et al. |
| 6,483,013 B1 | 11/2002 | Reynaerts et al. |
| 6,815,580 B1* | 11/2004 | Miller ................ C12N 15/8245 536/23.2 |
| 7,473,822 B1 | 1/2009 | Paz et al. |
| 2005/0289667 A1 | 12/2005 | Jefferson |
| 2005/0289672 A1 | 12/2005 | Jefferson |
| 2012/0317683 A1* | 12/2012 | Kreuzaler ............ C12N 9/0006 800/306 |

FOREIGN PATENT DOCUMENTS

| | | |
|---|---|---|
| EP | 0508909 A1 | 3/1992 |
| EP | 0189707 B1 | 8/1993 |
| EP | 0633317 B1 | 6/1994 |
| WO | 8707644 A1 | 12/1987 |
| WO | 9209696 A1 | 6/1992 |
| WO | 9215675 A1 | 9/1992 |
| WO | 9732977 A1 | 9/1997 |
| WO | 9837212 A1 | 8/1998 |
| WO | 0039313 A1 | 7/2000 |
| WO | 0070062 A1 | 11/2000 |
| WO | 0071733 A1 | 11/2000 |
| WO | 0142441 A2 | 6/2001 |
| WO | 0164023 A1 | 9/2001 |
| WO | 0181605 A2 | 11/2001 |
| WO | 02055651 A2 | 7/2002 |
| WO | 02057466 A2 | 7/2002 |
| WO | 03100066 A1 | 12/2003 |
| WO | 2004005480 A2 | 1/2004 |
| WO | 2004015115 A1 | 2/2004 |
| WO | 2004016793 A2 | 2/2004 |

(Continued)

OTHER PUBLICATIONS

Feng et al, 2007, Plant Cell Rep, 26:1635-1646.*
Xin et al , 2015, Plant Physiology, 167:574-585.*
Bari, Rafijul, et al., A glycolate dehydrogenase in the mitochondria of *Arabidopsis thaliana*, Journal of Experimental Botany, Mar. 2004, pp. 623-630, vol. 55, No. 397.
Carrington, James C., et al., Cap-Independent Enhancement of Translation by a Plant Potyvirus 5' Nontranslated Region, Journal of Virology, Apr. 1990, pp. 1590-1597, vol. 64, No. 4.
Christou, Paul, Rice transformation: bombardment, Plant Molecular Biology, 1997, pp. 197-203, vol. 35.
Clemente, Thomas E., et al., Progeny Analysis of Glyphosate Selected Transgenic Soybeans Derived from Agrobacterium-Medidated Transformation, Crop Sci, 2000, pp. 797-803, vol. 40.

(Continued)

*Primary Examiner* — Jason Deveau Rosen
(74) *Attorney, Agent, or Firm* — Arent Fox LLP

(57) ABSTRACT

Plants are provided with increased ribulose-1,5-bisphosphate (RuBP) regeneration capacity during the Calvin cycle through increased expression of sedoheptulose 1,7 bisphosphatase, in combination with reduced photo-respiratory losses through expression of glycolate catabolizing enzymes. Such plants have a greater growth rate and/or improved biomass and/or increased carbon fixation compared to untreated plants, or plants comprising only one of the features above.

33 Claims, No Drawings
Specification includes a Sequence Listing.

(56) References Cited

FOREIGN PATENT DOCUMENTS

| WO | 2004035734 A2 | 4/2004 |
|---|---|---|
| WO | 2006072607 A2 | 7/2006 |
| WO | 2006108830 A2 | 10/2006 |
| WO | 2007031547 A1 | 3/2007 |
| WO | 2008003666 A1 | 1/2008 |
| WO | 2010012796 A1 | 2/2010 |
| WO | 2010061186 A2 | 6/2010 |
| WO | 2010079117 A2 | 7/2010 |
| WO | 2011013764 A1 | 2/2011 |
| WO | 2011095460 A1 | 8/2011 |
| WO | 2011095528 A1 | 8/2011 |

OTHER PUBLICATIONS

Crossway, Anne, et al., Integration of foreign DNA following microinjection of tabacco mesophyll protoplasts, Mol. Gen Genet, 1986, pp. 179-185, vol. 2002.

De Block, Marc, et al., Transformation of *Brassica napus* and *Brassica oleracea* Using Agrobacterium tumefaciens and the Expression of the bar and neo Genes in the Transgenic Plants, Plant Physiol., 1989, pp. 694-701, vol. 91.

De Greve, H., et al., Nucleotide Sequence and Transcript Map of the Agrobacterium tumefaciens Ti Plasmid-Encoded Octopine Synthase Gene, Journal of Molecular and Applied Genetics, 1982, pp. 499-511, vol. 1.

De Pater, B. Sylvia, et al., The promoter of the rice gene GOS2 is active in various different monocot tissues and binds rice nuclear factor ASF-1, The Plant Journal, 1992, pp. 837-844, vol. 2, No. 6.

Depicker, A., et al., Nopaline Synthase: Transcript Mapping and Dna Sequence, Journal of Molecular and Applied Genetics, 1982, pp. 561-573, vol. 1.

Droste, Annette, et al., Transgenic fertile plants of soybean [*Glycine max* (L.) Merrill] obtained from bombarded embryogenic tissue, Euphytica, 2002, pp. 367-376, vol. 127.

Feng, Lingling, et al., Overexpression of SBPase enhances photosynthesis against high temperature stress in transgenic rice plants, Plant Cell Reporter, 2007, pp. 1635-1646, vol. 26.

GenBank Accession No. G68077, amino acids 1-58.

Hiei, Yukoh, et al., Efficient transformation of rice (*Oryza sativa* L.) mediated by Agrobacterium and sequence analysis of the boundaries of the T-DNA, The Plant Journal, 1994, pp. 271-282, vol. 6, No. 2.

Hiei, Yukoh, et al., Transformation of rice mediated by Agrobacterium tumefaciens, Plant Molecular Biology, 1997, pp. 205-218, vol. 35.

Kebeish, Rashad, et al., Chloroplastic photorespiratory bypass increases photosynthesis and biomass production in *Arabidopsis thaliana*, Nature Biotechnology, May 2007, pp. 593-599, vol. 25.

Klein, T.M., et al., High-velocity microprojectiles for delivery nucleic acids into living cells, Nature, 1987, pp. 70-73, vol. 327.

Krens, F.A., et al., In vitro transformation of plant protoplasts with Ti-plasmid DNA, Nature, Mar. 1982, pp. 72-74, vol. 296.

Kyozuka, Junko, et al., Light-Regulated and Cell-Specific Expression of Tomato rbcS-gusA and Rice rbcS-gusA Fusion Genes in Transgenic Rice 1, Plant Physiol., 1993, pp. 991-1000, vol. 102.

Lawson, T., et al., Decreased SBPase activity alters growth and development in transgenic tobacco plants, Plant, Cell and Environment, 2006, pp. 48-58, vol. 29.

Lefebvre, Stephanie, et al., Increased Sedoheptulose-1, 7-Bisphosphatase Activity in Transgenic Tobacco Plants Stimulates Photosynthesis and Growth from an Early Stage in Development1, Plant Physiology, May 2005, pp. 451-460, vol. 138.

Lord, J.M., Glycolate Oxidoreductase in *Escherichia coli*, Biochimica Et Biophysica ACTA, 1972, pp. 227-237, vol. 267.

Maughan, P.J., et al., Biolistic Transformation, Expression, and Inheritance of Bovine B-Casein in Soybean (*Glycine max*), In Vitro Cell. Dev. Biol. Plant, Jul.-Aug. 1999, pp. 344-349, vol. 35.

McElroy, David, et al., Isolation of an Efficient Actin Promoter for Use in Rice Transformation, The Plant Cell, Feb. 1990, pp. 163-171, vol. 2.

Miyagawa, Yoshiko, et al., Overexpression of a cyanobacterial fructose-1, 6-/sedoheptulose-1, 7-bisphosphatase in tobacco enhances photosynthesis and growth, Nature Biotechnology, 2001, pp. 965-969, vol. 19.

Nakamura, Yoshiko, et al., Disruption of the glycolate dehydrogenase gene in the high-CO2-requiring mutant HCR89 of Chlamydomonas reinhardtii1, Canadian Journal of Botany, 2005, pp. 820-833, vol. 83.

Negrutiu, I., et al., Hybrid genes in the analysis of transformation conditions, Plant Molecular Biology, 1987, pp. 363-373, vol. 8.

Nolke, Greta, et al., The expression of a recombinant glycolate dehydrogenase polyprotein in potato (*Solanum tuberosum*) plastids strongly enhances photosynthesis and tuber yield, Plant Biotechnology Journal, 2014, pp. 734-742, vol. 12.

Nomura, Mika, et al., The promoter of rbcS in a C3 plant (rice) directs organ-specific, light-dependent expression in a C4 plant (maize), but does not confer bundle sheath cell-specific expression, Plant Molecular Biology, 2000, pp. 99-106, vol. 44.

Odell, T., et al., Identification of DNA sequences required for activity of the cauliflower mosaic virus 35S promoter, Nature, Feb. 1985, pp. 810-812, vol. 313.

Olhoft, P.M., et al., L-Cysteine increases Agrobacterium-mediated T-DNA delivery into soybean cotyledonary-node cells, Plant Cell Report, 2001, pp. 706-711, vol. 20.

Olhoft, P.M., et al., The role of thiol compounds in increasing Agrobacterium-mediated transformation of soybean cotyledonary-node cells, Plant Cell Report, 2001, pp. 731-737, vol. 20.

Raines, Christine A., Increasing Photosynthetic Carbon Assimilation in C3 Plants to Improve Crop Yield: Current and Future Strategies, Plant Physiology, Jan. 2011, pp. 36-42, vol. 155.

Sanfacon, Helene, et al., A dissection of the cauliflower mosaic virus polyadenylation signal, Genes and Development, 1991, pp. 141-149, vol. 5.

Santarem, Eliane R., et al., Transformation of soybean [*Glycine max* (L.) Merrill] using proliferative embryogenic tissue maintained on semi-solid medium, In Vitro Cell. Dev. Biol.—Plant, Nov.-Dec. 1999, pp. 451-455, vol. 35.

Shillito, R.D., et al., High efficiency direct gene transfer to plants, Bio Technol., 1985, pp. 1099-1102, vol. 3.

Si, Li-Zhen et al., Isolation of a 1 195 bp 5'-Flanking region of rice cytosolic fructose-1, 6-bisphosphatase and analysis of its expression in transgenic rice, Acta Botanica Sinica, 2003, pp. 359-364, vol. 45, No. 3.

Tamoi, Masahiro, et al., Contribution of Fructose-1, 6-bisphosphatase and Sedoheptulose-1, 7-bisphosphatase to the Photosynthetic Rate and Carbon Flow in the Calvin Cycle in Transgenic Plants, Plant Cell Physiol., 2006, pp. 380-390, vol. 47, No. 3.

Thompson, Charles J., et al., Characterization of the herbicide-resistance gene bar from Streptomyces hygroscopicus, The EMBO Journal, 1987, pp. 2519-2523, vol. 6, No. 9.

Trick, Harold N., et al., Induction of somatic embryogenesis and genetic transformation of Ohio Buckeye (*Aesculus glabra* Willd.), In Vitro Cell. Dev. Biol.-Plant, Jan.-Feb. 1999, pp. 57-60, vol. 35.

Zambryski, Patricia, Basic Processes Underlying Agrobacterium-Mediated DNA Transfer to Plant Cells, Annual Review of Genetics, 1988, pp. 1-30, vol. 22.

Zhang, Zhanyuan, et al., The use of glufosinate as a selective agent in Agrobacterium-mediated transformation of soybean, Plant Cell, Tissue and Organ Culture, 1999, pp. 37-46, vol. 56.

\* cited by examiner

SEQUENCE LISTING

```
<160> NUMBER OF SEQ ID NOS: 12

<210> SEQ ID NO 1
<211> LENGTH: 1179
<212> TYPE: DNA
<213> ORGANISM: Oryza sativa

<400> SEQUENCE: 1
atggagacgg tggccgcggc cagctacacc cgcggggcgg cgacgcgctc gccagcgtgc      60
tgcgccgcca tgtccttttc gcagtcctac aggccaaagg ccgctagacc gccgagcacg     120
ttctacgggg agtcgctgcg ggttaacacg gcgaggtcgc tgccgtctgg gaggcagtcc     180
aaggcggcga gccgggcggc gctcagcacc cggtgcgaga tcggggacag cctggaggag     240
ttcctcacca aggcgacgcc agacaagaac ctcatcaggc tcctcatctg catgggcgag     300
gcgatgagga ccatctcgtt caaggtcagg acggcgtcgt gcggcggcac cgcctgcgtc     360
aactccttcg gtgacgagca gctcgccgtc gatatgctcg ccgataagct cctcttcgag     420
gctctggaat actctcatgt ctgcaagtat gcgtgctccg aggaagtccc ggagctgcaa     480
gacatgggtg gaccagtcga tggtggtttc agtgtagcat tcgaccctct tgatgggtcc     540
agcattgtcg acacgaactt cacagttgga accatatttg gtgtctggcc tggtgacaag     600
ctgacaggcg tcaccggtgg agaccaagtt gctgctgcga tgggcatcta tggccctcgc     660
actacttaca ttatcgctct caaagattgt cctggaactc acgagttcct tcttcttgat     720
gaaggaaaat ggcagcacgt caaggacacc acaaccattg gagaggggaa aatgttctct     780
cctggcaacc tgagggctac atttgataat cctgaatatg acaagctcat caactactat     840
gtcaaggaga agtacacatt gcgttacact ggaggaatgg ttcctgatgt caaccagatc     900
atagttaagg agaagggcat tttcaccaac gtgacgtctc cgacagccaa ggccaagctg     960
aggctcctgt tcgaggtggc gccgttgggt ttcttgatag agaaagccgg cgggtacagc    1020
agcgacggca acagtcggt gctcgacaag gtgatcaaca acctcgacga gcggactcaa    1080
gtggcctacg gttccaagaa cgagattatc cggttcgagg agactctcta cggctcgtcg    1140
aggctcaccg ccggcgccac cgtgggcgcc gccgcctga                           1179

<210> SEQ ID NO 2
<211> LENGTH: 392
<212> TYPE: PRT
<213> ORGANISM: Oryza sativa

<400> SEQUENCE: 2

Met Glu Thr Val Ala Ala Ala Ser Tyr Thr Arg Gly Ala Ala Thr Arg
1               5                   10                  15

Ser Pro Ala Cys Cys Ala Ala Met Ser Phe Ser Gln Ser Tyr Arg Pro
            20                  25                  30

Lys Ala Ala Arg Pro Pro Ser Thr Phe Tyr Gly Glu Ser Leu Arg Val
        35                  40                  45

Asn Thr Ala Arg Ser Leu Pro Ser Gly Arg Gln Ser Lys Ala Ala Ser
    50                  55                  60

Arg Ala Ala Leu Ser Thr Arg Cys Glu Ile Gly Asp Ser Leu Glu Glu
65                  70                  75                  80
```

-continued

```
Phe Leu Thr Lys Ala Thr Pro Asp Lys Asn Leu Ile Arg Leu Leu Ile
                85                  90                  95

Cys Met Gly Glu Ala Met Arg Thr Ile Ser Phe Lys Val Arg Thr Ala
            100                 105                 110

Ser Cys Gly Gly Thr Ala Cys Val Asn Ser Phe Gly Asp Glu Gln Leu
        115                 120                 125

Ala Val Asp Met Leu Ala Asp Lys Leu Leu Phe Glu Ala Leu Glu Tyr
    130                 135                 140

Ser His Val Cys Lys Tyr Ala Cys Ser Glu Glu Val Pro Glu Leu Gln
145                 150                 155                 160

Asp Met Gly Gly Pro Val Asp Gly Gly Phe Ser Val Ala Phe Asp Pro
                165                 170                 175

Leu Asp Gly Ser Ser Ile Val Asp Thr Asn Phe Thr Val Gly Thr Ile
            180                 185                 190

Phe Gly Val Trp Pro Gly Asp Lys Leu Thr Gly Val Thr Gly Gly Asp
        195                 200                 205

Gln Val Ala Ala Met Gly Ile Tyr Gly Pro Arg Thr Thr Tyr Ile
    210                 215                 220

Ile Ala Leu Lys Asp Cys Pro Gly Thr His Glu Phe Leu Leu Leu Asp
225                 230                 235                 240

Glu Gly Lys Trp Gln His Val Lys Asp Thr Thr Ile Gly Glu Gly
                245                 250                 255

Lys Met Phe Ser Pro Gly Asn Leu Arg Ala Thr Phe Asp Asn Pro Glu
            260                 265                 270

Tyr Asp Lys Leu Ile Asn Tyr Tyr Val Lys Glu Lys Tyr Thr Leu Arg
        275                 280                 285

Tyr Thr Gly Gly Met Val Pro Asp Val Asn Gln Ile Ile Val Lys Glu
    290                 295                 300

Lys Gly Ile Phe Thr Asn Val Thr Ser Pro Thr Ala Lys Ala Lys Leu
305                 310                 315                 320

Arg Leu Leu Phe Glu Val Ala Pro Leu Gly Phe Leu Ile Glu Lys Ala
                325                 330                 335

Gly Gly Tyr Ser Ser Asp Gly Lys Gln Ser Val Leu Asp Lys Val Ile
            340                 345                 350

Asn Asn Leu Asp Glu Arg Thr Gln Val Ala Tyr Gly Ser Lys Asn Glu
        355                 360                 365

Ile Ile Arg Phe Glu Glu Thr Leu Tyr Gly Ser Ser Arg Leu Thr Ala
    370                 375                 380

Gly Ala Thr Val Gly Ala Ala Ala
385                 390
```

<210> SEQ ID NO 3
<211> LENGTH: 499
<212> TYPE: PRT
<213> ORGANISM: Escherichia coli

<400> SEQUENCE: 3

```
Met Ser Ile Leu Tyr Glu Glu Arg Leu Asp Gly Ala Leu Pro Asp Val
1               5                   10                  15

Asp Arg Thr Ser Val Leu Met Ala Leu Arg Glu His Val Pro Gly Leu
            20                  25                  30

Glu Ile Leu His Thr Asp Glu Glu Ile Ile Pro Tyr Glu Cys Asp Gly
        35                  40                  45

Leu Ser Ala Tyr Arg Thr Arg Pro Leu Leu Val Val Leu Pro Lys Gln
    50                  55                  60
```

```
Met Glu Gln Val Thr Ala Ile Leu Ala Val Cys His Arg Leu Arg Val
 65                  70                  75                  80

Pro Val Val Thr Arg Gly Ala Gly Thr Gly Leu Ser Gly Gly Ala Leu
                 85                  90                  95

Pro Leu Glu Lys Gly Val Leu Val Met Ala Arg Phe Lys Glu Ile
            100                 105                 110

Leu Asp Ile Asn Pro Val Gly Arg Arg Ala Arg Val Gln Pro Gly Val
            115                 120                 125

Arg Asn Leu Ala Ile Ser Gln Ala Val Ala Pro His Asn Leu Tyr Tyr
130                 135                 140

Ala Pro Asp Pro Ser Ser Gln Ile Ala Cys Ser Ile Gly Gly Asn Val
145                 150                 155                 160

Ala Glu Asn Ala Gly Gly Val His Cys Leu Lys Tyr Gly Leu Thr Val
                165                 170                 175

His Asn Leu Leu Lys Ile Glu Val Gln Thr Leu Asp Gly Glu Ala Leu
            180                 185                 190

Thr Leu Gly Ser Asp Ala Leu Asp Ser Pro Gly Phe Asp Leu Leu Ala
            195                 200                 205

Leu Phe Thr Gly Ser Glu Gly Met Leu Gly Val Thr Thr Glu Val Thr
210                 215                 220

Val Lys Leu Leu Pro Lys Pro Pro Val Ala Arg Val Leu Leu Ala Ser
225                 230                 235                 240

Phe Asp Ser Val Glu Lys Ala Gly Leu Ala Val Gly Asp Ile Ile Ala
                245                 250                 255

Asn Gly Ile Ile Pro Gly Gly Leu Glu Met Met Asp Asn Leu Ser Ile
            260                 265                 270

Arg Ala Ala Glu Asp Phe Ile His Ala Gly Tyr Pro Val Asp Ala Glu
            275                 280                 285

Ala Ile Leu Leu Cys Glu Leu Asp Gly Val Glu Ser Asp Val Gln Glu
290                 295                 300

Asp Cys Glu Arg Val Asn Asp Ile Leu Leu Lys Ala Gly Ala Thr Asp
305                 310                 315                 320

Val Arg Leu Ala Gln Asp Glu Ala Glu Arg Val Arg Phe Trp Ala Gly
                325                 330                 335

Arg Lys Asn Ala Phe Pro Ala Val Gly Arg Ile Ser Pro Asp Tyr Tyr
            340                 345                 350

Cys Met Asp Gly Thr Ile Pro Arg Arg Ala Leu Pro Gly Val Leu Glu
            355                 360                 365

Gly Ile Ala Arg Leu Ser Gln Gln Tyr Asp Leu Arg Val Ala Asn Val
370                 375                 380

Phe His Ala Gly Asp Gly Asn Met His Pro Leu Ile Leu Phe Asp Ala
385                 390                 395                 400

Asn Glu Pro Gly Glu Phe Ala Arg Ala Glu Glu Leu Gly Gly Lys Ile
                405                 410                 415

Leu Glu Leu Cys Val Glu Val Gly Gly Ser Ile Ser Gly Glu His Gly
            420                 425                 430

Ile Gly Arg Glu Lys Ile Asn Gln Met Cys Ala Gln Phe Asn Ser Asp
            435                 440                 445

Glu Ile Thr Thr Phe His Ala Val Lys Ala Ala Phe Asp Pro Asp Gly
            450                 455                 460

Leu Leu Asn Pro Gly Lys Asn Ile Pro Thr Leu His Arg Cys Ala Glu
465                 470                 475                 480
```

```
Phe Gly Ala Met His Val His His Gly His Leu Pro Phe Pro Glu Leu
            485                 490                 495

Glu Arg Phe

<210> SEQ ID NO 4
<211> LENGTH: 350
<212> TYPE: PRT
<213> ORGANISM: Escherichia coli

<400> SEQUENCE: 4

Met Leu Arg Glu Cys Asp Tyr Ser Gln Ala Leu Leu Glu Gln Val Asn
1               5                   10                  15

Gln Ala Ile Ser Asp Lys Thr Pro Leu Val Ile Gln Gly Ser Asn Ser
            20                  25                  30

Lys Ala Phe Leu Gly Arg Pro Val Thr Gly Gln Thr Leu Asp Val Arg
        35                  40                  45

Cys His Arg Gly Ile Val Asn Tyr Asp Pro Thr Glu Leu Val Ile Thr
    50                  55                  60

Ala Arg Val Gly Thr Pro Leu Val Thr Ile Glu Ala Ala Leu Glu Ser
65                  70                  75                  80

Ala Gly Gln Met Leu Pro Cys Glu Pro Pro His Tyr Gly Glu Glu Ala
                85                  90                  95

Thr Trp Gly Gly Met Val Ala Cys Gly Leu Ala Gly Pro Arg Arg Pro
            100                 105                 110

Trp Ser Gly Ser Val Arg Asp Phe Val Leu Gly Thr Arg Ile Ile Thr
        115                 120                 125

Gly Ala Gly Lys His Leu Arg Phe Gly Gly Glu Val Met Lys Asn Val
    130                 135                 140

Ala Gly Tyr Asp Leu Ser Arg Leu Met Val Gly Ser Tyr Gly Cys Leu
145                 150                 155                 160

Gly Val Leu Thr Glu Ile Ser Met Lys Val Leu Pro Arg Pro Arg Ala
                165                 170                 175

Ser Leu Ser Leu Arg Arg Glu Ile Ser Leu Gln Glu Ala Met Ser Glu
            180                 185                 190

Ile Ala Glu Trp Gln Leu Gln Pro Leu Pro Ile Ser Gly Leu Cys Tyr
        195                 200                 205

Phe Asp Asn Ala Leu Trp Ile Arg Leu Glu Gly Gly Glu Gly Ser Val
    210                 215                 220

Lys Ala Ala Arg Glu Leu Leu Gly Gly Glu Glu Val Ala Gly Gln Phe
225                 230                 235                 240

Trp Gln Gln Leu Arg Glu Gln Leu Pro Phe Ser Leu Pro Gly
                245                 250                 255

Thr Leu Trp Arg Ile Ser Leu Pro Ser Asp Ala Pro Met Met Asp Leu
            260                 265                 270

Pro Gly Glu Gln Leu Ile Asp Trp Gly Gly Ala Leu Arg Trp Leu Lys
        275                 280                 285

Ser Thr Ala Glu Asp Asn Gln Ile His Arg Ile Ala Arg Asn Ala Gly
    290                 295                 300

Gly His Ala Thr Arg Phe Ser Ala Gly Asp Gly Phe Ala Pro Leu
305                 310                 315                 320

Ser Ala Pro Leu Phe Arg Tyr His Gln Gln Leu Lys Gln Gln Leu Asp
                325                 330                 335

Pro Cys Gly Val Phe Asn Pro Gly Arg Met Tyr Ala Glu Leu
            340                 345                 350
```

<210> SEQ ID NO 5
<211> LENGTH: 407
<212> TYPE: PRT
<213> ORGANISM: Escherichia coli

<400> SEQUENCE: 5

```
Met Gln Thr Gln Leu Thr Glu Glu Met Arg Gln Asn Ala Arg Ala Leu
 1               5                  10                  15

Glu Ala Asp Ser Ile Leu Arg Ala Cys Val His Cys Gly Phe Cys Thr
            20                  25                  30

Ala Thr Cys Pro Thr Tyr Gln Leu Leu Gly Asp Glu Leu Asp Gly Pro
        35                  40                  45

Arg Gly Arg Ile Tyr Leu Ile Lys Gln Val Leu Glu Gly Asn Glu Val
    50                  55                  60

Thr Leu Lys Thr Gln Glu His Leu Asp Arg Cys Leu Thr Cys Arg Asn
65                  70                  75                  80

Cys Glu Thr Thr Cys Pro Ser Gly Val Arg Tyr His Asn Leu Leu Asp
                85                  90                  95

Ile Gly Arg Asp Ile Val Glu Gln Lys Val Lys Arg Pro Leu Pro Glu
            100                 105                 110

Arg Ile Leu Arg Glu Gly Leu Arg Gln Val Val Pro Arg Pro Ala Val
        115                 120                 125

Phe Arg Ala Leu Thr Gln Val Gly Leu Val Leu Arg Pro Phe Leu Pro
    130                 135                 140

Glu Gln Val Arg Ala Lys Leu Pro Ala Glu Thr Val Lys Ala Lys Pro
145                 150                 155                 160

Arg Pro Pro Leu Arg His Lys Arg Arg Val Leu Met Leu Glu Gly Cys
                165                 170                 175

Ala Gln Pro Thr Leu Ser Pro Asn Thr Asn Ala Ala Thr Ala Arg Val
            180                 185                 190

Leu Asp Arg Leu Gly Ile Ser Val Met Pro Ala Asn Glu Ala Gly Cys
        195                 200                 205

Cys Gly Ala Val Asp Tyr His Leu Asn Ala Gln Glu Lys Gly Leu Ala
    210                 215                 220

Arg Ala Arg Asn Asn Ile Asp Ala Trp Trp Pro Ala Ile Glu Ala Gly
225                 230                 235                 240

Ala Glu Ala Ile Leu Gln Thr Ala Ser Gly Cys Gly Ala Phe Val Lys
                245                 250                 255

Glu Tyr Gly Gln Met Leu Lys Asn Asp Ala Leu Tyr Ala Asp Lys Ala
            260                 265                 270

Arg Gln Val Ser Glu Leu Ala Val Asp Leu Val Glu Leu Leu Arg Glu
        275                 280                 285

Glu Pro Leu Glu Lys Leu Ala Ile Arg Gly Asp Lys Lys Leu Ala Phe
    290                 295                 300

His Cys Pro Cys Thr Leu Gln His Ala Gln Lys Leu Asn Gly Glu Val
305                 310                 315                 320

Glu Lys Val Leu Leu Arg Leu Gly Phe Thr Leu Thr Asp Val Pro Asp
                325                 330                 335

Ser His Leu Cys Cys Gly Ser Ala Gly Thr Tyr Ala Leu Thr His Pro
            340                 345                 350

Asp Leu Ala Arg Gln Leu Arg Asp Asn Lys Met Asn Ala Leu Glu Ser
        355                 360                 365

Gly Lys Pro Glu Met Ile Val Thr Ala Asn Ile Gly Cys Gln Thr His
    370                 375                 380
```

-continued

Leu Ala Ser Ala Gly Arg Thr Ser Val Arg His Trp Ile Glu Ile Val
385                 390                 395                 400

Glu Gln Ala Leu Glu Lys Glu
            405

<210> SEQ ID NO 6
<211> LENGTH: 1058
<212> TYPE: PRT
<213> ORGANISM: Chlamydomonas reinhardtii

<400> SEQUENCE: 6

Ala Arg Gly Pro Ala Ser Pro Ser Ser Leu Glu Gln Gln Thr Arg Gln
1               5                   10                  15

Val Ala Gln Val Ala Val Gln Gln Ser Thr Gln Gln Ala Val Lys Val
            20                  25                  30

Val Val Pro Ala Ile Lys Val Asp Leu Val Gly Ala Val Ser Ser Val
        35                  40                  45

Ser Glu Ser Asp Lys Val Glu Pro Gly Val Phe Lys Asn Val Asp Gly
50                  55                  60

His Arg Phe Glu Asp Gly Arg Tyr Ala Ala Phe Val Glu Glu Ile Thr
65                  70                  75                  80

Lys Phe Ile Pro Lys Glu Arg Gln Tyr Ser Asp Pro Val Arg Thr Phe
                85                  90                  95

Ala Tyr Gly Thr Asp Ala Ser Phe Tyr Arg Leu Asn Pro Lys Leu Val
            100                 105                 110

Val Lys Val His Asn Glu Asp Glu Val Arg Arg Ile Met Pro Ile Ala
        115                 120                 125

Glu Arg Leu Gln Val Pro Ile Thr Phe Arg Ala Ala Gly Thr Ser Leu
130                 135                 140

Ser Gly Gln Ala Ile Thr Asp Ser Val Leu Ile Lys Leu Ser His Thr
145                 150                 155                 160

Gly Lys Asn Phe Arg Asn Phe Thr Val His Gly Asp Gly Ser Val Ile
                165                 170                 175

Thr Val Glu Pro Gly Leu Ile Gly Gly Glu Val Asn Arg Ile Leu Ala
            180                 185                 190

Ala His Gln Lys Lys Asn Lys Leu Pro Ile Gln Tyr Lys Ile Gly Pro
        195                 200                 205

Asp Pro Ser Ser Ile Asp Ser Cys Met Ile Gly Gly Ile Val Ser Asn
210                 215                 220

Asn Ser Ser Gly Met Cys Cys Gly Val Ser Gln Asn Thr Tyr His Thr
225                 230                 235                 240

Leu Lys Asp Met Arg Val Val Phe Val Asp Gly Thr Val Leu Asp Thr
                245                 250                 255

Ala Asp Pro Asn Ser Cys Thr Ala Phe Met Lys Ser His Arg Ser Leu
            260                 265                 270

Val Asp Gly Val Val Ser Leu Ala Arg Arg Val Gln Ala Asp Lys Glu
        275                 280                 285

Leu Thr Ala Leu Ile Arg Arg Lys Phe Ala Ile Lys Cys Thr Thr Gly
290                 295                 300

Tyr Ser Leu Asn Ala Leu Val Asp Phe Pro Asp Asn Pro Ile Glu
305                 310                 315                 320

Ile Ile Lys His Leu Ile Ile Gly Ser Glu Gly Thr Leu Gly Phe Val
                325                 330                 335

Ser Arg Ala Thr Tyr Asn Thr Val Pro Glu Trp Pro Asn Lys Ala Ser

```
                340                 345                 350
Ala Phe Ile Val Phe Pro Asp Val Arg Ala Ala Cys Thr Gly Ala Ser
            355                 360                 365
Val Leu Arg Asn Glu Thr Ser Val Asp Ala Val Glu Leu Phe Asp Arg
        370                 375                 380
Ala Ser Leu Arg Glu Cys Glu Asn Asn Glu Asp Met Met Arg Leu Val
385                 390                 395                 400
Pro Asp Ile Lys Gly Cys Asp Pro Met Ala Ala Leu Leu Ile Glu
                405                 410                 415
Cys Arg Gly Gln Asp Glu Ala Ala Leu Gln Ser Arg Ile Glu Glu Val
            420                 425                 430
Val Arg Val Leu Thr Ala Ala Gly Leu Pro Phe Gly Ala Lys Ala Ala
        435                 440                 445
Gln Pro Met Ala Ile Asp Ala Tyr Pro Phe His His Asp Gln Lys Asn
    450                 455                 460
Ala Lys Val Phe Trp Asp Val Arg Arg Gly Leu Ile Pro Ile Val Gly
465                 470                 475                 480
Ala Ala Arg Glu Pro Gly Thr Ser Met Leu Ile Glu Asp Val Ala Cys
                485                 490                 495
Pro Val Asp Lys Leu Ala Asp Met Met Ile Asp Leu Ile Asp Met Phe
            500                 505                 510
Gln Arg His Gly Tyr His Asp Ala Ser Cys Phe Gly His Ala Leu Glu
        515                 520                 525
Gly Asn Leu His Leu Val Phe Ser Gln Gly Phe Arg Asn Lys Glu Glu
    530                 535                 540
Val Gln Arg Phe Ser Asp Met Met Glu Glu Met Cys His Leu Val Ala
545                 550                 555                 560
Thr Lys His Ser Gly Ser Leu Lys Gly Glu His Gly Thr Gly Arg Asn
                565                 570                 575
Val Ala Pro Phe Val Glu Met Glu Trp Gly Asn Lys Ala Tyr Glu Leu
            580                 585                 590
Met Trp Glu Leu Lys Ala Leu Phe Asp Pro Ser His Thr Leu Asn Pro
        595                 600                 605
Gly Val Ile Leu Asn Arg Asp Gln Asp Ala His Ile Lys Phe Leu Lys
    610                 615                 620
Pro Ser Pro Ala Ala Ser Pro Ile Val Asn Arg Cys Ile Glu Cys Gly
625                 630                 635                 640
Phe Cys Glu Ser Asn Cys Pro Ser Arg Asp Ile Thr Leu Thr Pro Arg
                645                 650                 655
Gln Arg Ile Ser Val Tyr Arg Glu Met Tyr Arg Leu Lys Gln Leu Gly
            660                 665                 670
Pro Gly Ala Ser Glu Glu Glu Lys Lys Gln Leu Ala Ala Met Ser Ser
        675                 680                 685
Ser Tyr Ala Tyr Asp Gly Glu Gln Thr Cys Ala Ala Asp Gly Met Cys
    690                 695                 700
Gln Glu Lys Cys Pro Val Lys Ile Asn Thr Gly Asp Leu Ile Lys Ser
705                 710                 715                 720
Met Arg Ala Glu His Met Lys Glu Glu Lys Thr Ala Ser Gly Met Ala
                725                 730                 735
Asp Trp Leu Ala Ala Asn Phe Gly Val Ile Asn Ser Asn Val Pro Arg
            740                 745                 750
Phe Leu Asn Ile Val Asn Ala Met His Ser Val Val Gly Ser Ala Pro
        755                 760                 765
```

Leu Ser Ala Ile Ser Arg Ala Leu Asn Ala Thr Asn His Phe Val
                770                 775                 780

Pro Val Trp Asn Pro Tyr Met Pro Lys Gly Ala Ala Pro Leu Lys Val
785                 790                 795                 800

Pro Ala Pro Ala Pro Ala Ala Glu Ala Ser Gly Ile Pro Arg
                805                 810                 815

Lys Val Val Tyr Met Pro Ser Cys Val Thr Arg Met Met Gly Pro Ala
                820                 825                 830

Ala Ser Asp Thr Glu Thr Ala Ala Val His Glu Lys Val Met Ser Leu
                835                 840                 845

Phe Gly Lys Ala Gly Tyr Glu Val Ile Ile Pro Glu Gly Val Ala Ser
                850                 855                 860

Gln Cys Cys Gly Met Met Phe Asn Ser Arg Gly Phe Lys Asp Ala Ala
865                 870                 875                 880

Ala Ser Lys Gly Ala Glu Leu Glu Ala Ala Leu Leu Lys Ala Ser Asp
                885                 890                 895

Asn Gly Lys Ile Pro Ile Val Ile Asp Thr Ser Pro Cys Leu Ala Gln
                900                 905                 910

Val Lys Ser Gln Ile Ser Glu Pro Ser Leu Arg Phe Ala Leu Tyr Glu
                915                 920                 925

Pro Val Glu Phe Ile Arg His Phe Leu Val Asp Lys Leu Glu Trp Lys
                930                 935                 940

Lys Val Arg Asp Gln Val Ala Ile His Val Pro Cys Ser Ser Lys Lys
945                 950                 955                 960

Met Gly Ile Glu Glu Ser Phe Ala Lys Leu Ala Gly Leu Cys Ala Asn
                965                 970                 975

Glu Val Val Pro Ser Gly Ile Pro Cys Cys Gly Met Ala Gly Asp Arg
                980                 985                 990

Gly Met Arg Phe Pro Glu Leu Thr Gly Ala Ser Leu Gln His Leu Asn
                995                1000                1005

Leu Pro Lys Thr Cys Lys Asp Gly Tyr Ser Thr Ser Arg Thr Cys
               1010                1015                1020

Glu Met Ser Leu Ser Asn His Ala Gly Ile Asn Phe Arg Gly Leu
               1025                1030                1035

Val Tyr Leu Val Asp Glu Ala Thr Ala Pro Lys Lys Gln Ala Ala
               1040                1045                1050

Ala Ala Lys Thr Ala
               1055

<210> SEQ ID NO 7
<211> LENGTH: 622
<212> TYPE: PRT
<213> ORGANISM: Chlamydomonas reinhardtii

<400> SEQUENCE: 7

Ala Arg Gly Pro Ala Ser Pro Ser Ser Leu Glu Gln Gln Thr Arg Gln
1               5                   10                  15

Val Ala Gln Val Ala Val Gln Gln Ser Thr Gln Gln Ala Val Lys Val
                20                  25                  30

Val Val Pro Ala Ile Lys Val Asp Leu Val Gly Ala Val Ser Ser Val
                35                  40                  45

Ser Glu Ser Asp Lys Val Glu Pro Gly Val Phe Lys Asn Val Asp Gly
                50                  55                  60

His Arg Phe Glu Asp Gly Arg Tyr Ala Ala Phe Val Glu Glu Ile Thr

```
                65                  70                  75                  80
Lys Phe Ile Pro Lys Glu Arg Gln Tyr Ser Asp Pro Val Arg Thr Phe
                    85                  90                  95

Ala Tyr Gly Thr Asp Ala Ser Phe Tyr Arg Leu Asn Pro Lys Leu Val
                    100                 105                 110

Val Lys Val His Asn Glu Asp Glu Val Arg Arg Ile Met Pro Ile Ala
                    115                 120                 125

Glu Arg Leu Gln Val Pro Ile Thr Phe Arg Ala Ala Gly Thr Ser Leu
    130                 135                 140

Ser Gly Gln Ala Ile Thr Asp Ser Val Leu Ile Lys Leu Ser His Thr
145                 150                 155                 160

Gly Lys Asn Phe Arg Asn Phe Thr Val His Gly Asp Gly Ser Val Ile
                165                 170                 175

Thr Val Glu Pro Gly Leu Ile Gly Gly Glu Val Asn Arg Ile Leu Ala
                180                 185                 190

Ala His Gln Lys Lys Asn Lys Leu Pro Ile Gln Tyr Lys Ile Gly Pro
        195                 200                 205

Asp Pro Ser Ser Ile Asp Ser Cys Met Ile Gly Gly Ile Val Ser Asn
210                 215                 220

Asn Ser Ser Gly Met Cys Cys Gly Val Ser Gln Asn Thr Tyr His Thr
225                 230                 235                 240

Leu Lys Asp Met Arg Val Val Phe Val Asp Gly Thr Val Leu Asp Thr
                245                 250                 255

Ala Asp Pro Asn Ser Cys Thr Ala Phe Met Lys Ser His Arg Ser Leu
            260                 265                 270

Val Asp Gly Val Val Ser Leu Ala Arg Arg Val Gln Ala Asp Lys Glu
        275                 280                 285

Leu Thr Ala Leu Ile Arg Arg Lys Phe Ala Ile Lys Cys Thr Thr Gly
290                 295                 300

Tyr Ser Leu Asn Ala Leu Val Asp Phe Pro Val Asp Asn Pro Ile Glu
305                 310                 315                 320

Ile Ile Lys His Leu Ile Ile Gly Ser Glu Gly Thr Leu Gly Phe Val
                325                 330                 335

Ser Arg Ala Thr Tyr Asn Thr Val Pro Glu Trp Pro Asn Lys Ala Ser
                340                 345                 350

Ala Phe Ile Val Phe Pro Asp Val Arg Ala Ala Cys Thr Gly Ala Ser
            355                 360                 365

Val Leu Arg Asn Glu Thr Ser Val Asp Ala Val Glu Leu Phe Asp Arg
        370                 375                 380

Ala Ser Leu Arg Glu Cys Glu Asn Asn Glu Asp Met Met Arg Leu Val
385                 390                 395                 400

Pro Asp Ile Lys Gly Cys Asp Pro Met Ala Ala Leu Leu Ile Glu
                405                 410                 415

Cys Arg Gly Gln Asp Glu Ala Ala Leu Gln Ser Arg Ile Glu Glu Val
            420                 425                 430

Val Arg Val Leu Thr Ala Ala Gly Leu Pro Phe Gly Ala Lys Ala Ala
        435                 440                 445

Gln Pro Met Ala Ile Asp Ala Tyr Pro Phe His His Asp Gln Lys Asn
450                 455                 460

Ala Lys Val Phe Trp Asp Val Arg Arg Gly Leu Ile Pro Ile Val Gly
465                 470                 475                 480

Ala Ala Arg Glu Pro Gly Thr Ser Met Leu Ile Glu Asp Val Ala Cys
                485                 490                 495
```

```
Pro Val Asp Lys Leu Ala Asp Met Met Ile Asp Leu Ile Asp Met Phe
        500                 505                 510

Gln Arg His Gly Tyr His Asp Ala Ser Cys Phe Gly His Ala Leu Glu
        515                 520                 525

Gly Asn Leu His Leu Val Phe Ser Gln Gly Phe Arg Asn Lys Glu Glu
        530                 535                 540

Val Gln Arg Phe Ser Asp Met Met Glu Glu Met Cys His Leu Val Ala
545                 550                 555                 560

Thr Lys His Ser Gly Ser Leu Lys Gly Glu His Gly Thr Gly Arg Asn
                565                 570                 575

Val Ala Pro Phe Val Glu Met Glu Trp Gly Asn Lys Ala Tyr Glu Leu
                580                 585                 590

Met Trp Glu Leu Lys Ala Leu Phe Asp Pro Ser His Thr Leu Asn Pro
        595                 600                 605

Gly Val Ile Leu Asn Arg Asp Gln Asp Ala His Ile Lys Phe
        610                 615                 620

<210> SEQ ID NO 8
<211> LENGTH: 492
<212> TYPE: PRT
<213> ORGANISM: Synechocystis

<400> SEQUENCE: 8

Met Ala Ile Phe Ser Pro Val Asn Ala Val Thr Asp Ile Ile Pro Gln
1               5                   10                  15

Leu Glu Lys Ile Val Gly Gln Asp Gly Val Ile Lys Arg Lys Asp Glu
            20                  25                  30

Leu Phe Thr Tyr Glu Cys Asp Gly Leu Thr Gly Tyr Arg Gln Arg Pro
        35                  40                  45

Ala Leu Val Val Leu Pro Arg Thr Thr Glu Gln Val Ala Thr Ile Val
    50                  55                  60

Lys Leu Cys His Asp Arg Gln Ile Pro Trp Ile Ala Arg Gly Ala Gly
65                  70                  75                  80

Thr Gly Leu Ser Gly Gly Ala Leu Pro Gly Ala Asp Ser Leu Leu Ile
                85                  90                  95

Val Thr Thr Arg Met Arg Gln Ile Leu Ala Val Asp Tyr Asp Asn Gln
            100                 105                 110

Thr Ile Val Val Gln Pro Gly Val Asn Asn Trp Val Thr Gln Thr
        115                 120                 125

Val Ser Gly Ala Gly Phe Tyr Tyr Ala Pro Asp Pro Ser Ser Gln Ile
    130                 135                 140

Val Cys Ser Ile Gly Gly Asn Ile Ala Glu Asn Ser Gly Gly Val His
145                 150                 155                 160

Cys Leu Lys Tyr Gly Thr Thr Thr Asn His Val Leu Gly Leu Lys Leu
                165                 170                 175

Val Ile Pro Asp Gly Ser Ile Val Glu Val Gly Gly Gln Val Pro Glu
            180                 185                 190

Thr Pro Gly Tyr Asp Leu Thr Gly Leu Phe Val Gly Ser Glu Gly Thr
        195                 200                 205

Leu Gly Ile Ala Thr Glu Ile Thr Leu Lys Ile Leu Lys Thr Pro Glu
    210                 215                 220

Ser Ile Cys Val Val Leu Ala Asp Phe Leu Ser Leu Glu Ala Thr Ala
225                 230                 235                 240

Gln Ser Val Ala Asp Ile Ile Ala Ala Gly Ile Val Pro Ala Gly Met
```

```
            245                 250                 255
Glu Ile Met Asp Asn Phe Ser Ile Asn Ala Val Glu Asp Val Val Ala
            260                 265                 270

Thr Asn Cys Tyr Pro Arg Asp Ala Ala Ile Leu Leu Val Glu Leu
        275                 280                 285

Asp Gly Leu Pro Ile Glu Val Glu Leu Asn Gln Ala Lys Val Glu Glu
        290                 295                 300

Ile Cys Arg Asn Asn Gly Ala Arg Asn Thr Ala Ile Ala Tyr Asp Gln
305                 310                 315                 320

Glu Thr Arg Leu Lys Met Trp Lys Gly Arg Lys Ala Ala Phe Ala Ala
                325                 330                 335

Ala Gly Lys Leu Ser Pro Ser Tyr Phe Val Gln Asp Gly Val Val Pro
                340                 345                 350

Arg Thr Gln Leu Val Gln Ile Leu Ser Asp Ile Asn Asp Leu Ser Lys
                355                 360                 365

Lys Tyr Gly Phe Ala Ile Ala Asn Val Phe His Ala Gly Asp Gly Asn
        370                 375                 380

Leu His Pro Leu Ile Leu Tyr Asp Gln Lys Val Pro Gly Ala Trp Glu
385                 390                 395                 400

Lys Val Glu Glu Leu Gly Gly Glu Ile Leu Lys Arg Cys Val Glu Leu
                405                 410                 415

Gly Gly Ser Leu Ser Gly Glu His Gly Ile Gly Ile Asp Lys Asn Cys
                420                 425                 430

Phe Met Pro Asn Met Phe Asn Glu Val Asp Leu Glu Thr Met Gln Trp
        435                 440                 445

Val Arg Gln Cys Phe Asn Pro Asp Asn Leu Ala Asn Pro Gly Lys Leu
        450                 455                 460

Phe Pro Thr Pro Arg Ser Cys Gly Glu Val Ala Asn Ala Gln Arg Leu
465                 470                 475                 480

Asn Leu Gly Gln Asp Lys Lys Met Glu Glu Ile Tyr
                485                 490

<210> SEQ ID NO 9
<211> LENGTH: 537
<212> TYPE: PRT
<213> ORGANISM: Arabidopsis thaliana

<400> SEQUENCE: 9

Gly Asp Val Thr Val Leu Ser Pro Val Lys Gly Arg Arg Leu Pro
1               5                  10                  15

Thr Cys Trp Ser Ser Leu Phe Pro Leu Ala Ile Ala Ala Ser Ala
            20                  25                  30

Thr Ser Phe Ala Tyr Leu Asn Leu Ser Asn Pro Ser Ile Ser Glu Ser
            35                  40                  45

Ser Ser Ala Leu Asp Ser Arg Asp Ile Thr Val Gly Gly Lys Asp Ser
        50                  55                  60

Thr Glu Ala Val Val Lys Gly Glu Tyr Lys Gln Val Pro Lys Glu Leu
65                  70                  75                  80

Ile Ser Gln Leu Lys Thr Ile Leu Glu Asp Asn Leu Thr Thr Asp Tyr
                85                  90                  95

Asp Glu Arg Tyr Phe His Gly Lys Pro Gln Asn Ser Phe His Lys Ala
            100                 105                 110

Val Asn Ile Pro Asp Val Val Phe Pro Arg Ser Glu Glu Val
            115                 120                 125
```

```
Ser Lys Ile Leu Lys Ser Cys Asn Glu Tyr Lys Val Pro Ile Val Pro
    130                 135                 140
Tyr Gly Gly Ala Thr Ser Ile Glu Gly His Thr Leu Ala Pro Lys Gly
145                 150                 155                 160
Gly Val Cys Ile Asp Met Ser Leu Met Lys Arg Val Lys Ala Leu His
                    165                 170                 175
Val Glu Asp Met Asp Val Ile Val Glu Pro Gly Ile Gly Trp Leu Glu
                180                 185                 190
Leu Asn Glu Tyr Leu Glu Tyr Gly Leu Phe Phe Pro Leu Asp Pro
            195                 200                 205
Gly Pro Gly Ala Ser Ile Gly Gly Met Cys Ala Thr Arg Cys Ser Gly
    210                 215                 220
Ser Leu Ala Val Arg Tyr Gly Thr Met Arg Asp Asn Val Ile Ser Leu
225                 230                 235                 240
Lys Val Val Leu Pro Asn Gly Asp Val Val Lys Thr Ala Ser Arg Ala
                245                 250                 255
Arg Lys Ser Ala Ala Gly Tyr Asp Leu Thr Arg Leu Ile Ile Gly Ser
                260                 265                 270
Glu Gly Thr Leu Gly Val Ile Thr Glu Ile Thr Leu Arg Leu Gln Lys
            275                 280                 285
Ile Pro Gln His Ser Val Val Ala Val Cys Asn Phe Pro Thr Val Lys
    290                 295                 300
Asp Ala Ala Asp Val Ala Ile Ala Thr Met Met Ser Gly Ile Gln Val
305                 310                 315                 320
Ser Arg Val Glu Leu Leu Asp Glu Val Gln Ile Arg Ala Ile Asn Met
                325                 330                 335
Ala Asn Gly Lys Asn Leu Thr Glu Ala Pro Thr Leu Met Phe Glu Phe
                340                 345                 350
Ile Gly Thr Glu Ala Tyr Thr Arg Glu Gln Thr Gln Ile Val Gln Gln
            355                 360                 365
Ile Ala Ser Lys His Asn Gly Ser Asp Phe Met Phe Ala Glu Glu Pro
    370                 375                 380
Glu Ala Lys Lys Glu Leu Trp Lys Ile Arg Lys Glu Ala Leu Trp Ala
385                 390                 395                 400
Cys Tyr Ala Met Ala Pro Gly His Glu Ala Met Ile Thr Asp Val Cys
                405                 410                 415
Val Pro Leu Ser His Leu Ala Glu Leu Ile Ser Arg Ser Lys Lys Glu
                420                 425                 430
Leu Asp Ala Ser Ser Leu Leu Cys Thr Val Ile Ala His Ala Gly Asp
            435                 440                 445
Gly Asn Phe His Thr Cys Ile Met Phe Asp Pro Ser Ser Glu Glu Gln
    450                 455                 460
Arg Arg Glu Ala Glu Arg Leu Asn His Phe Met Val His Ser Ala Leu
465                 470                 475                 480
Ser Met Asp Gly Thr Cys Thr Gly Glu His Gly Val Gly Thr Gly Lys
                485                 490                 495
Met Lys Tyr Leu Glu Lys Glu Leu Gly Ile Glu Ala Leu Gln Thr Met
                500                 505                 510
Lys Arg Ile Lys Lys Thr Leu Asp Pro Asn Asp Ile Met Asn Pro Gly
            515                 520                 525
Lys Leu Ile Pro Pro His Val Cys Phe
    530                 535
```

<210> SEQ ID NO 10
<211> LENGTH: 9013
<212> TYPE: DNA
<213> ORGANISM: Artificial Sequence
<220> FEATURE:
<223> OTHER INFORMATION: nucleotide sequence of the T-DNA of vector PTCD155

<400> SEQUENCE: 10

```
aattacaacg gtatatatcc tgccagtact gggcccctc gagggcgatc gctacgtacc      60
tgcagggcgg ccgcaagctt ttggtggtag gaatgtagtt ttctgacaaa gtcaattact    120
gaatataaaa aaaatctgca cagctctgcg tcaacagttg tccaagggat gcctcaaaaa    180
tctgtgcaga ttatcagtcg tcacgcagaa gcagaacatc atggtgtgct aggtcagctt    240
cttgcattgg gccatgaatc cggttggttg ttaatctctc ctctcttatt ctcttatatt    300
aagatgcata actctttat gtagtctaaa aaaaaatcca gtggatcgga tagtagtacg    360
tcatggtgcc attaggtacc gttgaaccta acagatattt atgcatgtgt atatatatag    420
ctatatagac aaaattggtg ccgattatag acccaaaagc aataggtata tataatataa    480
tacagaccac accaccaaac taagaatcga tcaaatagac aaggcatgtc tccaaattgt    540
cttaaactat ttccgtaggt tcagccgttc aggagtcgaa tcagcctctg ccggcgtttt    600
ctttgcacgt acgacggaca cacatgggca taccatatag ctggtccatg acattaggag    660
agagaacgta cgtgttgacc tgtagctgag atataacaag gttgattata atatcaccaa    720
acatgaaatc atccaaggat gacccataac tatcactact atagtactgc atctggtaaa    780
agaaattgta tagactctat ttcgagcact accacataac gcctgcaatg tgacaccta    840
cctattcact aatgtgcctc ttcccacacg cttccaccc gtactgctca cagctttaag    900
aaccagaaca atgagtaat attagtgtcg gttcatggct aaaaccagca ctgatgtaca    960
tgaccacata tgtcaaatgc tgcttctagg catgacccgc tcttactaat acctactcat   1020
cgctagaaga attttcggct gataaattt caatttaagc aagagttatc cgcgttggtt   1080
cataactcaa actgatggcc ccaaccatat tagtgcaaat ttcacatatg atcataacct   1140
tttcatatga aatcggatcg tgatgaactt tatataaaca ttgtagctgt cgatgatacc   1200
tacaatttta tagttcacaa cctttttatt tcaagtcatt taaatgccca aataggtgtt   1260
tcaaatctca gatagaaatg ttcaaaagta aaaaaggtcc ctatcataac ataattgata   1320
tgtaagtgag ttggaaaatg ataagtacgt gtgagagaga tcggagatca aattctggtg   1380
taataatgta tgtatttcag tcataaaaat tggtagcagt agttgggct ctgtatatat   1440
accggtaagg atgggatggt agtagaataa ttctttttt gttttagtt ttttctggtc   1500
caaaatttca aatttggatc ccttacttgt accaactaat attaatgagt gttgagggca   1560
gtagaggtgc aactttacca taatccctct gtttcaggtt ataagacgtt ttgactttaa   1620
atttgactaa gttatgcgc aaatatagta atatttataa tactaaatta gtttcattaa   1680
ataaataatt gaatatattt tcataataaa tttgtgttga gttcaaaata ttattaattt   1740
tttctacaaa cttggtcaaa cttaaagcag tttgactttg accaaagtca aaacgtctta   1800
taacttgaaa cggatggatt actttttttg tggggacaag tttacaatgt ttaataaaag   1860
cacaatccat cttaatgttt tcaagctgaa tattgtaaaa ttcatggata aaccagcttc   1920
taaatgttta accggaaaaa tgtcgaacga caattaata tttttaagtg atggggagta   1980
ttaattaagg agtgacaact caactttcaa tatcgtacta aactgtggga tttatttct   2040
aaaattttat acctgccaa ttcacgtgtt gtagatcttt tttttcact aaccgacacc   2100
```

```
aggtatatca attttattga atatagcagc aaaaagaatg tgttgtactt gtaaacaaaa    2160
agcaaactgt acataaaaaa aaatgcactc ctatataatt aagctcataa agatgctttg    2220
cttcgtgagg gcccaagttt tgatgacctt ttgcttgatc tcgaaattaa aatttaagta    2280
ctgttaaggg agttcacacc accatcaatt ttcagcctga agaaacagtt aaacaacgac    2340
cccgatgacc agtctactgc tctccacata ctagctgcat tattgatcac aaaacaaaac    2400
aaaacgaaat aaaaatcagc agcgagagtg tgcagagaga gacaaaggtg atctggcgtg    2460
gatatctccc catccatcct cacccgcgct gcccatcact cgccgccgca tactccatca    2520
tgtggagaga ggaagacgag gaccacagcc agagcccggg tcgagatgcc accacggcca    2580
caacccacga gcccggcgcg acaccaccgc gcgcgcgtga gccagccaca aacgcccgcg    2640
gataggcgcg cgcacgccgg ccaatcctac cacatccccg gcctccgcgg ctcgcgagcg    2700
ccgctgccat ccgatccgct gagttttggc tatttatacg taccgcggga gcctgtgtgc    2760
agagcagtgc atctcaagaa gtactcgagc aaagaaggag agagcttggt gagctgcaga    2820
gcaggtaacc accccgcccc tctcctcttt ctttctccgt tttttttttc cgtctcggtc    2880
tcgatctttg gccttggtag tttgggtggg cgagaggcgg cttcgtgcgc gcccagatcg    2940
gtgcgcggga ggggcgggat ctcgcggctg gggctctcgc cggcgtggat ccggcccgga    3000
tctcgcgggg aatggggctc tcggatgtag atctgcgatc cgccgttgtt ggggagatg     3060 atgggggtt taaaatttcc gccatgctaa acaagatcag gaagagggga aagggcact      3120 atggtttata tttttatata tttctgctgc ttcgtcaggc ttagatgtgc tagatctttc    3180
tttcttcttt ttgtgggtag aatttgaatc cctcagcatt gttcatcggt agttttctt     3240 ttcatgattt gtgacaaatg cagcctcgtg cggagctttt ttgtaggtag accatggcca    3300
gcatctcaag ctccgttgcc actgtatcaa ggacggctcc tgctcaagca aacatggtcg    3360
caccatttac cggcctaaag agcaacgctg ccttccccac cacaaagaag gcgaatgatt    3420
tctcgacact accctccaac ggtggccgtg ttcagtgcat gcaggtctgg cctgcctacg    3480
gcaacaagaa gttcgaaacc cttagttacc tgccgcccct ttcgatggcc caacagttta    3540
tgatggcgag ctcagcgacc gccgttgcac cgtttcaagg cctcaagagt acagctagtc    3600
tcccagtggc taggcgctcc agtaggagtt tgggaaacgt ctccaacgga ggaaggattc    3660
ggtgtatggc acgcggccca gcaagcccaa gctcgttgga gcaacaaaca aggcaagtgg    3720
cccaggtcgc tgtccaacag tctacccagc aagcggttaa ggtggttgtt cccgccatta    3780
aggtcgacct tgtgggagcc gtgagttcag tgtctgagtc cgacaaggtt gagccggggg    3840
ttttcaagaa cgttgatggc caccgcttcg aagatgggag atacgcagcg ttcgtggagg    3900
aaatcaccaa attcatcccg aaggagagac agtactccga ccccgttcgc acatttgcct    3960
atggaacgga tgcctccttc taccggctca acccaaagct agtcgtgaag gttcacaacg    4020
aggacgaagt gcgtaggata atgccaatcg ccgaaaggct ccaggtccct ataacgttca    4080
gagcggcagg cacttcactc tctggccaag ccatcacgga cagcgtgctg attaagctgt    4140
cccacaccgg gaagaacttc cgcaatttca cggtgcatgg cgacgggagc gtgataacgg    4200
tggaacctgg cctaattggg ggagaagtca accggatcct ggctgcgcat cagaagaaga    4260
acaagctccc gatccagtac aagatcggcc cggatccatc gtccattgac tcttgcatga    4320
tcggcgggat agtctcgaat aactcatccg ggatgtgctg cggcgtttca caaaatacct    4380
accacaccct caaggacatg cgcgttgtgt tcgtggatgg gactgtgcta gatacagccg    4440
```

```
acctaacag ctgcactgca tttatgaaga gccatcgaag cctcgtggat ggagtagtct    4500
ctctcgcaag gagagtccag gcggacaagg agttgactgc tctcatccgt cgcaagttcg    4560
cgattaagtg cacgaccggc tattccctga acgcacttgt cgacttcccg gttgacaacc    4620
ccatcgagat cattaagcac ctgatcatag gctctgaagg gaccctggga ttcgtgagtc    4680
gtgccaccta taacacggtg ccggaatggc aaacaaagc atccgccttc atcgtgtttc    4740
cagacgttag agccgcttgc accggagcat ctgtgctacg gaacgaaacc tcagttgacg    4800
cggttgagct gttcgatagg gcctcattgc gcgagtgcga gaataatgag gacatgatgc    4860
ggctcgtccc ggacattaaa ggctgcgacc caatggccgc ggcgttacta atcgagtgta    4920
gaggccaaga cgaggcggca cttcagtccc gaatagagga agtggtccga gtgttaactg    4980
ccgctggatt gccgttcgga gccaaggcag ctcagcctat ggcgatagac gcctacccct    5040
ttcaccatga ccagaagaac gccaaggtct tttgggatgt taggcgcgga ctgattccaa    5100
ttgtgggtgc cgcgagggaa cctgggactt cgatgctgat tgaggatgtg gcttgtcccg    5160
ttgacaagct ggccgacatg atgatcgacc tcatcgacat gtttcaacga catggctacc    5220
atgatgcgtc atgctttggc cacgcactgg agggtaactt gcacctcgtt ttctcccagg    5280
gctttaggaa caaggaggaa gttcagcgct tctcagacat gatggaggag atgtgccacc    5340
tggttgcgac aaagcattcc ggaagcctta agggcgaaca tggaaccggg agaaatgtcg    5400
cacccttcgt ggagatggag tggggaaaca aggcctatga gctgatgtgg gagctgaagg    5460
ctctgtttga tccaagccac accctcaatc ccggtgtcat cctgaaccgg gaccaagatg    5520
cgcacattaa gttttttgaaa cccagccctg ccgcgagccc aatcgtcaat cggtgcatcg    5580
aatgcgggtt ttgtgagagc aactgcccat ctagggacat cacactcaca cctcgccaac    5640
ggatcagcgt gtacagggaa atgtatcgct tgaaacaact tgggccggga gcctctgagg    5700
aagagaagaa gcagctggct gcgatgtcga gctcttacgc ttacgatggc gagcaaacgt    5760
gtgccgctga tgggatgtgc caagagaagt gcccagtgaa gatcaacacc ggcgacctca    5820
ttaagagcat gcgggccgag cacatgaaag aagagaagac agcctctggt atggcggact    5880
ggcttgctgc gaattttggc gtgatcaact ccaatgtccc tcgtttcctg aatatcgtga    5940
acgcgatgca ctccgtggtt ggtagcgccc ccttaagtgc catttcacgc gcactgaacg    6000
cagctacgaa ccacttcgtc ccagtttgga acccatacat gccgaaagga gcggcaccct    6060
taaaagttcc agcgccgcca gctccggccg ctgccgaagc ctcgggaatc cctaggaaag    6120
tcgtttacat gccctcctgc gtgacagaaa tgatgggtcc agcagcttcg gacactgaga    6180
ctgctgccgt ccatgagaaa gtcatgtcgc tcttcgggaa ggctggctac gaagtgatca    6240
tacctgaggg cgttgcgagc caatgctgcg ggatgatgtt caattcccgg ggatttaagg    6300
acgcagcggc ctcaaaaggt gccgaacttg aagcggcttt gctgaaggcc tccgataacg    6360
ggaagatccc gatcgtgatc gacacttccc catgccttgc ccaggtcaaa tcgcaaatta    6420
gcgagccgag tctccgcttt gccctctacg agccagtcga gtttataagg cacttcctcg    6480
tcgataagct cgaatggaag aaggtccgtg atcaggtcgc tattcacgtg ccgtgttcct    6540
cgaagaagat ggggatcgag gaatcgttcg cgaaattggc gggcttgtgt gcgaatgaag    6600
tggtcccaag cggaataccc tgctgtggta tggcgggaga tcgtggaatg cgattccctg    6660
agctcacggg agcgtctctg caacatctca atctcccgaa gacctgcaag gacggttact    6720
ctactagccg cacttgcgag atgtccctct taaccacgc ggggatcaat ttccgcggac    6780
ttgtctatct ggtcgacgaa gctaccgccc caaaaaagca agcggctgcc gcaaaaacgg    6840
```

```
cgtgattgct agcacgcgtt taattaaatt taaatggcgc gccgaagcag atcgttcaaa      6900
catttggcaa taaagtttct taagattgaa tcctgttgcc ggtcttgcga tgattatcat      6960
ataatttctg ttgaattacg ttaagcatgt aataattaac atgtaatgca tgacgttatt      7020
tatgagatgg gttttatga ttagagtccc gcaattatac atttaatacg cgatagaaaa      7080
caaaatatag cgcgcaaact aggataaatt atcgcgcgcg gtgtcatcta tgttactaga      7140
tcggaattcg atatcattac cctgttatcc ctaaagctta ttaatataac ttcgtatagc      7200
atacattata cgaagttatg tttcctacgc agcaggtctc atcaagacga tctacccgag      7260
taacaatctc caggagatca aatacettcc caagaaggtt aaagatgcag tcaaaagatt      7320
caggactaat tgcatcaaga acacagagaa agacatattt ctcaagatca gaagtactat      7380
tccagtatgg acgattcaag gcttgcttca taaaccaagg caagtaatag agattggagt      7440
ctctaaaaag gtagttccta ctgaatctaa ggccatgcat ggagtctaag attcaaatcg      7500
aggatctaac agaactcgcc gtgaagactg gcgaacagtt catacagagt cttttacgac      7560
tcaatgacaa gaagaaaatc ttcgtcaaca tggtggagca cgacactctg gtctactcca      7620
aaaatgtcaa agatacagtc tcagaagacc aaagggctat tgagacttttt caacaaagga      7680 taatttcggg aaacctcctc ggattccatt gcccagctat ctgtcacttc atcgaaagga      7740
cagtagaaaa ggaaggtggc tcctacaaat gccatcattg cgataaagga aaggctatca      7800
ttcaagatgc ctctgccgac agtggtccca agatggacc cccacccacg aggagcatcg      7860
tggaaaaaga agacgttcca accacgtctt caaagcaagt ggattgatgt gacatctcca      7920
ctgacgtaag ggatgacgca caatcccact atccttcgca agacccttcc tctatataag      7980
gaagttcatt tcatttggag aggacacgct gaaatcacca gtctctctct ataaatctat      8040
ctctctctct ataacaatgg acccagaacg acgcccggcc gacatccgcc gtgccaccga      8100
ggcggacatg ccggcggtct gcaccatcgt caaccactac atcgagacaa gcacggtcaa      8160
cttccgtacc gagccgcagg aaccgcagga gtggacggac gacctcgtcc gtctgcggga      8220
gcgctatccc tggctcgtcg ccgaggtgga cggcgaggtc gccggcatcg cctacgcggg      8280
cccctggaag gcacgcaacg cctacgactg gacggccgag tcgaccgtgt acgtctcccc      8340
ccgccaccag cggacgggac tgggctccac gctctacacc cacctgctga agtccctgga      8400
ggcacagggc ttcaagagcg tggtcgctgt catcgggctg cccaacgacc cgagcgtgcg      8460
catgcacgag gcgctcggat atgcccccg cggcatgctg cgggcggccg gcttcaagca      8520
cgggaactgg catgacgtgg gtttctggca gctggacttc agcctgccgg taccgccccg      8580
tccggtcctg cccgtcaccg agatctgaga tcacccgttc taggatccga agcagatcgt      8640
tcaaacattt ggcaataaag tttcttaaga ttgaatcctg ttgccggtct tgcgatgatt      8700
atcatatatt ttctgttgaa ttacgttaag catgtaataa ttaacatgta atgcatgacg      8760
ttatttatga gatgggtttt tatgattaga gtcccgcaat tatacatttta atacgcgata      8820 gaaaacaaaa tatagcgcgc aaactaggat aaattatcgc gcgcggtgtc atctatgtta      8880
ctagatcgaa acataacttc gtatagcata cattatacga agttatatgg atctcgaggc      8940
attacggcat tacggcactc gcgagggtcc caattcgagc atggagccat ttacaattga      9000
atatatcctg ccg                                                        9013
```

<210> SEQ ID NO 11
<211> LENGTH: 7461
<212> TYPE: DNA

<213> ORGANISM: Artificial Sequence
<220> FEATURE:
<223> OTHER INFORMATION: nucleotide sequence of the T-DNA of vector PTMV548

<400> SEQUENCE: 11

```
aattacaacg gtatatatcc tgccagtact gggcccccctc gagggcgatc gctacgtacc      60
tgcagggcgg ccgcaaaggt acactcgatt acattgccgg taataggcat atagtagttg     120
cgtaccatgt cgagttgatc atgagttcat gaccagcccc gtgtgaaatc ctcggttcaa     180
gttctttccg agttgcatat accatcgctt tacctcagcg acaataaat gagcagggac      240
tttttactcg gattatccgt cgcatatgct tgtcaaaaga tacgaaaggc agacgaatcc     300
agtaggataa gtcatatggg ggtgtgtttt atttctgaaa aaatggtaa gtttgaggaa      360
agttgggagt ttggaaaaaa agttaagttt atgtgtatag taaagttttt gatgtattat     420
gatgtgatgg aaagtcagaa ataggggaag actaaacaca gccatggtaa agcagctctt     480
ccccgagctg accggaagct cgagcagcct agcgtgaagg taaagcgtcc agtcgcctgc     540
gagtccccct cccgccctgt agctctcact cgaagtcgaa cccggtgcca tattccacgc     600
gtaaatgcta ggccattaaa ggcaaacaac ttctaccttg gagagttgga ggcttggagc     660
ccatttgcga gaccccctct ccggttaacc gtttcgccgt cacatcgggc gcacagctta     720
acacgacgta cttggtcata atctcgcacc atccgcgtcg gcgtcggcgt cggcgcctct     780
gctcaacaac aactacaccc ccgctagctt gctgcgttgc cgtagtacgt ggcggtacag     840
ggcaaagccg tgctcgcctc tagtagctcg acttagctcg ggcctcgatc acctgggggg     900
cgaaacgcga cgaccacaga cgcacacggc caccgcgcta ccagccatcg cggatagagg     960
ggataggcct ccgcgccgat ccgttggag ctcctcgccc ctcggctccc agcctcactt    1020
tctcccctcg ctacctccca aaacccctaa aaaaaacgcc caatacgtac accgcgcccg    1080
cgtcacgtca cctcaccggg tcagttcccg cgccgtgtga ccaatactca acacttaaac    1140
cgcgcgcttt ttagccgacc cgagcagccg gagagtgagg cgaggcgaag cgaagggaag    1200
agcgcgaggc agagtaagca gacgagaaga acagcgcgcg gcgcggtagc tgaggagagt    1260
ggtgcggagc aggtaaccac cccgcccctc tcctcttttct ttctccgttt ttttttccg    1320
tctcggtctc gatctttggc cttggtagtt tgggtgggcg agaggcggct tcgtgcgcgc    1380
ccagatcggt gcgcgggagg ggcgggatct cgcggctggg gctctcgccg gcgtggatcc    1440
ggcccggatc tcgcggggaa tggggctctc ggatgtagat ctgcgatccg ccgttgttgg    1500
gggagatgat gggggttta aaatttccgc catgctaaac aagatcagga agaggggaaa    1560
agggcactat ggtttatatt tttatatatt tctgctgctt cgtcaggctt agatgtgcta    1620
gatctttctt tcttcttttt gtgggtagaa tttgaatccc tcagcattgt tcatcggtag    1680
ttttttcttt catgatttgt gacaaatgca gcctcgtgcg gagcttttt gtaggtagac      1740
catggccagc atctcaagct ccgttgccac tgtatcaagg acggctcctg ctcaagcaaa    1800
catggtcgca ccatttaccg gcctaaagag caacgctgcc ttccccacca caagaaggc     1860
gaatgatttc tcgacactac cctccaacgg tggccgtgtt cagtgcatgc aggtctggcc    1920
tgcctacggc aacaagaagt cgaaaccct tagttacctg ccgcccctt cgatggcccc       1980
aacagttatg atggcgagct cagcgaccgc cgttgcaccg tttcaaggcc tcaagagtac    2040
agctagtctc ccagtggcta ggcgctccag taggagtttg ggaaacgtct ccaacggagg    2100
aaggattcgg tgtatggcac gcggcccagc aagcccaagc tcgttggagc aacaaacaag    2160
```

```
gcaagtggcc caggtcgctg tccaacagtc tacccagcaa gcggttaagg tggttgttcc    2220
cgccattaag gtcgacctttg tgggagccgt gagttcagtg tctgagtccg acaaggttga   2280
gccgggggtt ttcaagaacg ttgatggcca ccgcttcgaa gatgggagat acgcagcgtt    2340
cgtggaggaa atcaccaaat tcatcccgaa ggagagacag tactccgacc ccgttcgcac    2400
atttgcctat ggaacggatg cctccttcta ccggctcaac ccaaagctag tcgtgaaggt    2460
tcacaacgag gacgaagtgc gtaggataat gccaatcgcc gaaaggctcc aggtccctat    2520
aacgttcaga gcggcaggca cttcactctc tggccaagcc atcacggaca gcgtgctgat    2580
taagctgtcc cacaccggga agaacttccg caatttcacg gtgcatggcg acggagcgt    2640
gataacggtg gaacctggcc taattggggg agaagtcaac cggatcctgg ctgcgcatca    2700
gaagaagaac aagctcccga tccagtacaa gatcggcccg gatccatcgt ccattgactc    2760
ttgcatgatc ggcgggatag tctcgaataa ctcatccggg atgtgctgcg gcgtttcaca    2820
aaatacctac cacacccctca aggacatgcg cgttgtgttc gtggatggga ctgtgctaga    2880
tacagccgac cctaacagct gcactgcatt tatgaagagc catcgaagcc tcgtggatgg    2940
agtagtctct ctcgcaagga gagtccaggc ggacaaggag ttgactgctc tcatccgtcg    3000
caagttcgcg attaagtgca cgaccggcta ttccctgaac gcacttgtcg acttcccggt    3060
tgacaaccccc atcgagatca ttaagcacct gatcataggc tctgaaggga ccctgggatt    3120
cgtgagtcgt gccaccctata acacggtgcc ggaatggcca aacaaagcat ccgccttcat    3180
cgtgtttcca gacgttagag ccgcttgcac cggagcatct gtgctacgga acgaaacctc    3240
agttgacgcg gttgagctgt tcgataggggc ctcattgcgc gagtgcgaga ataatgagga    3300
catgatgcgg ctcgtcccgg acattaaagg ctgcgaccca atggccgcgg cgttactaat    3360
cgagtgtaga ggccaagacg aggcggcact tcagtcccga atagaggaag tggtccgagt    3420
gttaactgcc gctggattgc cgttcggagc caaggcagct cagcctatgg cgatagacgc    3480
ctaccccttt caccatgacc agaagaacgc caaggtctttt tgggatgtta ggcgcgcgact    3540
gattccaatt gtgggtgccg cgagggaacc tgggacttcg atgctgattg aggatgtggc    3600
ttgtcccgtt gacaagctgg ccgacatgat gatcgacctc atcgacatgt tcaacgaca    3660
tggctaccat gatgcgtcat gctttggcca cgcactggag ggtaacttgc acctcgtttt    3720
ctcccagggc tttaggaaca aggaggaagt tcagcgcttc tcagacatga tggaggagat    3780
gtgccacctg gttgcgacaa agcattccgg aagccttaag ggcgaacatg gaaccgggag    3840
aaatgtcgca cccttcgtgg agatggagtg gggaaacaag gcctatgagc tgatgtggga    3900
gctgaaggct ctgtttgatc caagccacac cctcaatccc ggtgtcatcc tgaaccggga    3960
ccaagatgcg cacattaagt ttttgaaacc cagcccctgcc gcgagcccaa tcgtcaatcg    4020
gtgcatcgaa tgcgggtttt gtgagagcaa ctgcccatct agggacatca cactcacacc    4080
tcgccaacgg atcagcgtgt acagggaaat gtatcgcttg aaacaacttg gccgggagc    4140
ctctgaggaa gagaagaagc agctggctgc gatgtcgagc tcttacgctt acgatggcga    4200
gcaaacgtgt gccgctgatg ggatgtgcca agagaagtgc ccagtgaaga tcaacaccgg    4260
cgacctcatt aagagcatgc gggccgagca catgaaagaa gagaagacag cctctggtat    4320
ggcggactgg cttgctgcga tttttggcgt gatcaactcc aatgtccctc gtttcctgaa    4380
tatcgtgaac gcgatgcact ccgtggttgg tagcgccccc ttaagtgcca tttcacgcgc    4440
actgaacgca gctacgaacc acttcgtccc agtttggaac ccatcacatgc cgaaaggagc    4500
ggcaccccta aaagttccag cgccgccagc tccggccgct gccgaagcct cgggaatccc    4560
```

```
taggaaagtc gtttacatgc cctcctgcgt gacgagaatg atgggtccag cagcttcgga    4620
cactgagact gctgccgtcc atgagaaagt catgtcgctc ttcgggaagg ctggctacga    4680
agtgatcata cctgagggcg ttgcgagcca atgctgcggg atgatgttca attcccgggg    4740
atttaaggac gcagcggcct caaaaggtgc cgaacttgaa gcggctttgc tgaaggcctc    4800
cgataacggg aagatcccga tcgtgatcga cacttcccca tgccttgccc aggtcaaatc    4860
gcaaattagc gagccgagtc tccgctttgc cctctacgag ccagtcgagt ttataaggca    4920
cttcctcgtc gataagctcg aatggaagaa ggtccgtgat caggtcgcta ttcacgtgcc    4980
gtgttcctcg aagaagatgg ggatcgagga atcgttcgcg aaattggcgg gcttgtgtgc    5040
gaatgaagtg gtcccaagcg gaataccctg ctgtggtatg gcgggagatc gtggaatgcg    5100
attccctgag ctcacgggag cgtctctgca acatctcaat ctcccgaaga cctgcaagga    5160
cggttactct actagccgca cttgcgagat gtccctctct aaccacgcgg ggatcaattt    5220
ccgcggactt gtctatctgg tcgacgaagc taccgcccca aaaagcaag cggctgccgc    5280 aaaaacggcg tgattgctag cacgcgttta attaaattta aatggcgcgc cgaagcagat    5340
cgttcaaaca tttggcaata aagtttctta agattgaatc ctgttgccgg tcttgcgatg    5400
attatcatat aatttctgtt gaattacgtt aagcatgtaa taattaacat gtaatgcatg    5460
acgttattta tgagatgggt ttttatgatt agagtcccgc aattatacat ttaatacgcg    5520
atagaaaaca aaatatagcg cgcaaactag gataaattat cgcgcgcggt gtcatctatg    5580
ttactagatc ggaattcgat atcattaccc tgttatccct aaagcttatt aatataactt    5640
cgtatagcat acattatacg aagttatgtt tcctacgcag caggtctcat caagacgatc    5700
tacccgagta acaatctcca ggagatcaaa taccttccca agaaggttaa agatgcagtc    5760
aaaagattca ggactaattg catcaagaac acagagaaag acatatttct caagatcaga    5820
agtactattc cagtatggac gattcaaggc ttgcttcata aaccaaggca agtaatagag    5880
attggagtct ctaaaaaggt agttcctact gaatctaagg ccatgcatgg agtctaagat    5940
tcaaatcgag gatctaacag aactcgccgt gaagactggc gaacagttca tacagagtct    6000
tttacgactc aatgacaaga agaaaatctt cgtcaacatg gtggagcacg acactctggt    6060
ctactccaaa aatgtcaaag atacagtctc agaagaccaa agggctattg agactttca    6120 acaaggata atttcgggaa acctcctcgg attccattgc ccagctatct gtcacttcat    6180
cgaaaggaca gtagaaaagg aaggtggctc ctacaaatgc catcattgcg ataaaggaaa    6240
ggctatcatt caagatgcct ctgccgacag tggtcccaaa gatggacccc cacccacgag    6300
gagcatcgtg gaaaaagaag acgttccaac cacgtcttca aagcaagtgg attgatgtga    6360
catctccact gacgtaaggg atgacgcaca atcccactat ccttcgcaag acccttcctc    6420
tatataagga agttcatttc atttggagag gacacgctga aatcaccagt ctctctctat    6480
aaatctatct ctctctctat aacaatggac ccagaacgac gcccggccga catccgccgt    6540
gccaccgagg cggacatgcc ggcggtctgc accatcgtca accactacat cgagacaagc    6600
acggtcaact tccgtaccga gccgcaggaa ccgcaggagt ggacggacga cctcgtccgt    6660
ctgcgggagc gctatccctg gctcgtcgcc gaggtggacg cgcgaggtcgc cggcatcgcc    6720 tacgcgggcc cctggaaggc acgcaacgcc tacgactgga cggccgagtc gaccgtgtac    6780
gtctcccccc gccaccagcg gacgggactg ggctccacgc tctacaccca cctgctgaag    6840
tccctggagg cacagggctt caagagcgtg gtcgctgtca tcgggctgcc caacgacccg    6900
```

| | |
|---|---:|
| agcgtgcgca tgcacgaggc gctcggatat gccccccgcg gcatgctgcg ggcggccggc | 6960 |
| ttcaagcacg ggaactggca tgacgtgggt ttctggcagc tggacttcag cctgccggta | 7020 |
| ccgccccgtc cggtcctgcc cgtcaccgag atctgagatc acccgttcta ggatccgaag | 7080 |
| cagatcgttc aaacatttgg caataaagtt tcttaagatt gaatcctgtt gccggtcttg | 7140 |
| cgatgattat catataattt ctgttgaatt acgttaagca tgtaataatt aacatgtaat | 7200 |
| gcatgacgtt atttatgaga tgggttttta tgattagagt cccgcaatta tacatttaat | 7260 |
| acgcgataga aaacaaaata tagcgcgcaa actaggataa attatcgcgc gcggtgtcat | 7320 |
| ctatgttact agatcgaaac ataacttcgt atagcataca ttatacgaag ttatatggat | 7380 |
| ctcgaggcat tacggcatta cggcactcgc gagggtccca attcgagcat ggagccattt | 7440 |
| acaattgaat atatcctgcc g | 7461 |

```
<210> SEQ ID NO 12
<211> LENGTH: 13922
<212> TYPE: DNA
<213> ORGANISM: Artificial Sequence
<220> FEATURE:
<223> OTHER INFORMATION: nucleotide sequence of the T-DNA of vector
      PTCD163

<400> SEQUENCE: 12
```

| | |
|---|---:|
| aattacaacg gtatatatcc tgccagtact gggcccccctc gagggcgatc gccaattgtt | 60 |
| tgttattgtg gcgctctatc atagatgtcg ctataaacct attcagcaca atatattgtt | 120 |
| ttcattttaa tattgtacat ataagtagta gggtacaatc agtaaattga acggagaata | 180 |
| ttattcataa aaatacgata gtaacgggtg atatattcat tagaatgaac cgaaaccggc | 240 |
| ggtaaggatc tgagctacac atgctcaggt tttttacaac gtgcacaaca gaattgaaag | 300 |
| caaatatcat gcgatcatag gcgtctcgca tatctcatta aagcaggacg cgtgctagca | 360 |
| atcaggcggc ggcgcccacg gtggcgccgg cggtgagcct cgacgagccg tagagagtct | 420 |
| cctcgaaccg gataatctcg ttcttggaac cgtaggccac ttgagtccgc tcgtcgaggt | 480 |
| tgttgatcac cttgtcgagc accgactgtt tgccgtcgct gctgtacccg ccggctttct | 540 |
| ctatcaagaa acccaacggc gccacctcga acaggagcct cagcttggcc ttggctgtcg | 600 |
| gagacgtcac gttggtgaaa atgcccttct ccttaactat gatctggttg acatcaggaa | 660 |
| ccattcctcc agtgtaacgc aatgtgtact tctccttgac atagtagttg atgagcttgt | 720 |
| catattcagg attatcaaat gtagccctca ggttgccagg agagaacatt ttcccctctc | 780 |
| caatggttgt ggtgtccttg acgtgctgcc attttccttc atcaagaaga aggaactcgt | 840 |
| gagttccagg acaatctttg agagcgataa tgtaagtagt gcgagggcca tagatgccca | 900 |
| tcgcagcagc aacttggtct ccaccggtga cgcctgtcag cttgtcacca ggccagacac | 960 |
| caaatatggt tccaactgtg aagttcgtgt cgacaatgct ggacccatca agagggtcga | 1020 |
| atgctacact gaaaccacca tcgactggtc cacccatgtc ttgcagctcc gggacttcct | 1080 |
| cggagcacgc atacttgcag acatgagagt attccagagc ctcgaagagg agcttatcgg | 1140 |
| cgagcatatc gacggcgagc tgctcgtcac cgaaggagtt gacgcaggcg gtgccgccgc | 1200 |
| acgacgccgt cctgaccttg aacgagatgg tcctcatcgc ctcgcccatg cagatgagga | 1260 |
| gcctgatgag gttcttgtct ggcgtcgcct tggtgaggaa ctcctccagg ctgtccccga | 1320 |
| tctcgcaccg ggtgctgagc gccgccggc tcgccgcctt ggactgcctc ccagacggca | 1380 |
| gcgacctcgc cgtgttaacc cgcagcgact ccccgtagaa cgtgctcggc ggtctagcgg | 1440 |

```
cctttggcct gtaggactgc gaaaaggaca tggcggcgca gcacgctggc gagcgcgtcg   1500
ccgccccgcg ggtgtagctg gccgcggcca ccgtctccat ggtctaccta caaaaaagct   1560
ccgcacgagg ctgcatttgt cacaaatcat gaaaagaaaa actaccgatg aacaatgctg   1620
agggattcaa attctaccca caaaaagaag aagaaagat ctagcacatc taagcctgac    1680
gaagcagcag aaatatataa aaatataaac catagtgccc ttttcccctc ttcctgatct   1740
tgtttagcat ggcggaaatt ttaaaccccc catcatctcc cccaacaacg gcggatcgca   1800
gatctacatc cgagagcccc attccccgcg agatccgggc cggatccacg ccggcgagag   1860
ccccagccgc gagatcccgc ccctcccgcg caccgatctg ggcgcgcacg aagccgcctc   1920
tcgcccaccc aaactaccaa ggccaaagat cgagaccgag acggaaaaaa aaaacggaga   1980
aagaaagagg agaggggcgg ggtggttacc tgctctgcag ctcaccaagc tctctccttc   2040
tttgctcgag tacttcttga gatgcactgc tctgcacaca ggctcccgcg gtacgtataa   2100
atagccaaaa ctcagcggat cggatggcag cggcgctcgc gagccgcgga ggccggggat   2160
gtggtaggat tggccggcgt gcgcgcgcct atccgcgggc gtttgtggct ggctcacgcg   2220
cgcgcggtgg tgtcgcgccg ggctcgtggg ttgtggccgt ggtggcatct cgacccgggc   2280
tctggctgtg gtcctcgtct tcctctctcc acatgatgga gtatgcggcg gcgagtgatg   2340
ggcagcgcgg gtgaggatgg atggggagat atccacgcca gatcacctt gtctctctct   2400 gcacactctc gctgctgatt tttatttcgt tttgttttgt tttgtgatca ataatgcagc   2460
tagtatgtgg agagcagtag actggtcatc ggggtcgttg tttaactgtt tcttcaggct   2520
gaaaattgat ggtggtgtga actcccttaa cagtacttaa attttaattt cgagatcaag   2580
caaaaggtca tcaaaacttg ggccctcacg aagcaaagca tctttatgag cttaattata   2640
taggagtgca tttttttta tgtacagttt gcttttgtt tacaagtaca acacattctt     2700
tttgctgcta tattcaataa aattgatata cctggtgtcg gttagtgaaa aaaaagatc    2760 tacaacacgt gaattggcag ggtataaaat tttagaaaat aaatcccaca gtttagtacg   2820
atattgaaag ttgagttgtc actccttaat taatactccc catcacttaa aaatattaat   2880
ttgtcgttcg acatttttccc ggttaaacat ttagaagctg gttatccat gaattttaca   2940 atattcagct tgaaaacatt aagatggatt gtgcttttat taaacattgt aaacttgtcc   3000
ccacaaaaaa agtaatccat ccgtttcaag ttataagacg ttttgacttt ggtcaaagtc   3060
aaactgcttt aagtttgacc aagtttgtag aaaaaattaa taatattttg aactcaacac   3120
aaatttatta tgaaaatata ttcaattatt tatttaatga aactaattta gtattataaa   3180
tattactata tttgcgcata aacttagtca aatttaaagt caaaacgtct tataacctga   3240
aacagaggga ttatggtaaa gttgcacctc tactgccctc aacactcatt aatattagtt   3300
ggtacaagta agggatccaa atttgaaatt ttggaccaga aaaactaaa aacaaaaaaa     3360 gaattattct actaccatcc catccttacc ggtatatata cagagcccca actactgcta   3420 ccaatttta tgactgaaat acatacatta ttacaccaga atttgatctc cgatctctct    3480
cacacgtact tatcattttc caactcactt acatatcaat tatgttatga tagggacctt   3540
ttttactttt gaacatttct atctgagatt tgaaacacct atttgggcat ttaaatgact   3600
tgaaataaaa aggttgtgaa ctataaaatt gtaggtatca tcgacagcta caatgtttat   3660
ataaagttca tcacgatccg atttcatatg aaaaggttat gatcatatgt gaaatttgca   3720
ctaatatggt tggggccatc agtttgagtt atgaaccaac gcggataact cttgcttaaa   3780
ttgaaaattt atcagccgaa aattcttcta gcgatgagta ggtattagta agagcgggtc   3840
```

```
atgcctagaa gcagcatttg acatatgtgg tcatgtacat cagtgctggt tttagccatg    3900
aaccgacact aatattactc atttgttctg gttcttaaag ctgtgagcag tacgggtgga    3960
aagcgtgtgg gaagaggcac attagtgaat aggtagggtg tcacattgca ggcgttatgt    4020
ggtagtgctc gaaatagagt ctatacaatt tcttttacca gatgcagtac tatagtagtg    4080
atagttatgg gtcatccttg gatgatttca tgtttggtga tattataatc aaccttgtta    4140
tatctcagct acaggtcaac acgtacgttc tctctcctaa tgtcatggac cagctatatg    4200
gtatgcccat gtgtgtccgt cgtacgtgca agaaaacgc cggcagaggc tgattcgact    4260
cctgaacggc tgaacctacg aaatagtttt aagacaattt ggagacatgc cttgtctatt    4320
tgatcgattc ttagtttggt ggtgtggtct gtattatatt atatatacct attgcttttg    4380
ggtctataat cggcaccaat tttgtctata tagctatata tatacacatg cataaatatc    4440
tgttaggttc aacggtacct aatggcacca tgacgtacta ctatccgatc cactggattt    4500
ttttttagac tacataaaag agttatgcat cttaatataa gagaataaga gaggagagat    4560
taacaaccaa ccggattcat ggcccaatgc aagaagctga cctagcacac catgatgttc    4620
tgcttctgcg tgacgactga taatctgcac agattttga ggcatccctt ggacaactgt    4680
tgacgcagag ctgtgcagat tttttttata ttcagtaatt gactttgtca gaaaactaca    4740
ttcctaccac caaaagctta aatcaccagt ctctctctac aaatctatct ctctctattt    4800
ttctccagaa taatgtgtga gtagttccca gataagggaa ttagggttct tatagggttt    4860
cgctcatgtg ttgagcatat aagaaacct tagtatgtat ttgtatttgt aaaatacttc    4920
tatcaataaa atttctaatt cctaaaacca aaatccagtg cggccgccct gcagggcggc    4980
cgcaagcttt tggtggtagg aatgtagttt tctgacaaag tcaattactg aatataaaaa    5040
aaatctgcac agctctgcgt caacagttgt ccaagggatg cctcaaaaat ctgtgcagat    5100
tatcagtcgt cacgcagaag cagaacatca tggtgtgcta ggtcagcttc ttgcattggg    5160
ccatgaatcc ggttggttgt taatctctcc tctcttattc tcttatatta agatgcataa    5220
ctcttttatg tagtctaaaa aaaaatccag tggatcggat agtagtacgt catggtgcca    5280
ttaggtaccg ttgaacctaa cagatattta tgcatgtgta tatatatagc tatatagaca    5340
aaattggtgc cgattataga cccaaaagca ataggtatat ataatataat acagaccaca    5400
ccaccaaact aagaatcgat caaatagaca aggcatgtct ccaaattgtc ttaaactatt    5460
tccgtaggtt cagccgttca ggagtcgaat cagcctctgc cggcgttttc tttgcacgta    5520
cgacggacac acatgggcat accatatagc tggtccatga cattaggaga gaaacgtac    5580 gtgttgacct gtagctgaga tataacaagg ttgattataa tatcaccaaa catgaaatca    5640
tccaaggatg acccataact atcactacta tagtactgca tctggtaaaa gaaattgtat    5700
agactctatt tcgagcacta ccacataacg cctgcaatgt gacaccctac ctattcacta    5760
atgtgcctct tcccacacgc tttccacccg tactgctcac agctttaaga accagaacaa    5820
atgagtaata ttagtgtcgg ttcatggcta aaaccagcac tgatgtacat gaccacatat    5880
gtcaaatgct gcttctaggc atgacccgct cttactaata cctactcatc gctagaagaa    5940
ttttcggctg ataaattttc aatttaagca agagttatcc gcgttggttc ataactcaaa    6000
ctgatggccc caaccatatt agtgcaaatt tcacatatga tcataacctt tcatatgaa    6060 atcggatcgt gatgaacttt atataaacat tgtagctgtc gatgataact acaatttat    6120 agttcacaac cttttatttt caagtcattt aaatgcccaa ataggtgttt caaatctcag    6180
```

```
atagaaatgt tcaaaagtaa aaaaggtccc tatcataaca taattgatat gtaagtgagt    6240
tggaaaatga taagtacgtg tgagagagat cggagatcaa attctggtgt aataatgtat    6300
gtatttcagt cataaaaatt ggtagcagta gttggggctc tgtatatata ccggtaagga    6360
tgggatggta gtagaataat tcttttttg ttttagttt tttctggtcc aaaatttcaa    6420
atttggatcc cttacttgta ccaactaata ttaatgagtg ttgagggcag tagaggtgca    6480
actttaccat aatccctctg tttcaggtta aagacgtttt tgactttaaa tttgactaag    6540
tttatgcgca aatatagtaa tatttataat actaaattag tttcattaaa taaataattg    6600
aatatatttt cataataaat ttgtgttgag ttcaaaatat tattaatttt ttctacaaac    6660
ttggtcaaac ttaaagcagt ttgactttga ccaaagtcaa aacgtcttat aacttgaaac    6720
ggatggatta cttttttgt ggggacaagt ttacaatgtt taataaaagc acaatccatc    6780
ttaatgtttt caagctgaat attgtaaaat tcatggataa accagcttct aaatgtttaa    6840
ccgggaaaat gtcgaacgac aaattaatat ttttaagtga tggggagtat taattaagga    6900
gtgacaactc aactttcaat atcgtactaa actgtgggat ttattttcta aaattttata    6960
ccctgccaat tcacgtgttg tagatctttt tttttcacta accgacacca ggtatatcaa    7020
ttttattgaa tatagcagca aaaagaatgt gttgtacttg taaacaaaaa gcaaactgta    7080
cataaaaaaa aatgcactcc tatataatta agctcataaa gatgctttgc ttcgtgaggg    7140
cccaagtttt gatgaccttt tgcttgatct cgaaattaaa atttaagtac tgttaaggga    7200
gttcacacca ccatcaattt tcagcctgaa gaaacagtta acaacgaccc cgatgacca    7260 gtctactgct ctccacatac tagctgcatt attgatcaca aaacaaaaca aaacgaaata    7320
aaaatcagca gcgagagtgt gcagagagag acaaaggtga tctggcgtgg atatctcccc    7380
atccatcctc acccgcgctg cccatcactc gccgccgcat actccatcat gtggagagag    7440
gaagacgagg accacagcca gagcccgggt cgagatgcca ccacggccac aacccacgag    7500 cccgcgcga caccaccgcg cgcgcgtgag ccagccacaa acgcccgcgg ataggcgcgc    7560
gcacgccggc caatcctacc acatccccgg cctccgcggc tcgcgagcgc cgctgccatc    7620
cgatccgctg agttttggct atttatacgt accgcgggag cctgtgtgca gagcagtgca    7680
tctcaagaag tactcgagca agaaggaga gagcttggtg agctgcagag caggtaacca    7740 ccccgccccct ctcctctttc tttctccgtt tttttttcc gtctcggtct cgatctttgg    7800
ccttggtagt ttgggtgggc gagaggcggc ttcgtgcgcg cccagatcgg tgcgcgggag    7860
gggcgggatc tcgcggctgg ggctctcgcc ggcgtggatc cggcccggat ctcgcgggga    7920
atggggctct cggatgtaga tctgcgatcc gccgttgttg ggggagatga tgggggttt    7980 aaaatttccg ccatgctaaa caagatcagg aagaggggaa aagggcacta tggtttatat    8040
ttttatatat ttctgctgct tcgtcaggct tagatgtgct agatctttct ttcttctttt    8100
tgtgggtaga atttgaatcc ctcagcattg ttcatcggta gttttctttt tcatgatttg    8160
tgacaaatgc agcctcgtgc ggagcttttt tgtaggtaga ccatggccag catctcaagc    8220
tccgttgcca ctgtatcaag gacggctcct gctcaagcaa acatggtcgc accatttacc    8280
ggcctaaaga gcaacgctgc cttccccacc acaaagaagg cgaatgattt ctcgacacta    8340
ccctccaacg gtggccgtgt tcagtgcatg caggtctggc ctgcctacgg caacaagaag    8400
ttcgaaaccc ttagttacct gccgcccctt tcgatggccc caacagttat gatggcgagc    8460
tcagcgaccc ccgttgcacc gtttcaaggc ctcaagagta cagctagtct cccagtggct    8520
aggcgctcca gtaggagttt gggaaacgtc tccaacggag gaaggattcg gtgtatggca    8580
```

```
cgcggcccag caagcccaag ctcgttggag caacaaacaa ggcaagtggc ccaggtcgct    8640
gtccaacagt ctacccagca agcggttaag gtggttgttc ccgccattaa ggtcgacctt    8700
gtgggagccg tgagttcagt gtctgagtcc gacaaggttg agccgggggt tttcaagaac    8760
gttgatggcc accgcttcga agatgggaga tacgcagcgt tcgtggagga aatcaccaaa    8820
ttcatcccga aggagagaca gtactccgac cccgttcgca catttgccta tggaacggat    8880
gcctccttct accggctcaa cccaaagcta gtcgtgaagg ttcacaacga ggacgaagtg    8940
cgtaggataa tgccaatcgc cgaaaggctc caggtcccta taacgttcag agcggcaggc    9000
acttcactct ctggccaagc catcacggac agcgtgctga ttaagctgtc ccacaccggg    9060
aagaacttcc gcaatttcac ggtgcatggc gacgggagcg tgataacggt ggaacctggc    9120
ctaattgggg gagaagtcaa ccggatcctg gctgcgcatc agaagaagaa caagctcccg    9180
atccagtaca agatcggccc ggatccatcg tccattgact cttgcatgat cggcgggata    9240
gtctcgaata actcatccgg gatgtgctgc ggcgtttcac aaaataccta ccacaccctc    9300
aaggacatgc gcgttgtgtt cgtggatggg actgtgctag atacagccga ccctaacagc    9360
tgcactgcat ttatgaagag ccatcgaagc ctcgtggatg gagtagtctc tctcgcaagg    9420
agagtccagg cggacaagga gttgactgct ctcatccgtc gcaagttcgc gattaagtgc    9480
acgaccggct attccctgaa cgcacttgtc gacttcccgg ttgacaaccc catcgagatc    9540
attaagcacc tgatcatagg ctctgaaggg accctgggat tcgtgagtcg tgccacctat    9600
aacacggtgc cggaatggcc aaacaaagca tccgccttca tcgtgtttcc agacgttaga    9660
gccgcttgca ccggagcatc tgtgctacgg aacgaaacct cagttgacgc ggttgagctg    9720
ttcgataggg cctcattgcg cgagtgcgag aataatgagg acatgatgcg gctcgtcccg    9780
gacattaaag gctgcgaccc aatggccgcg gcgttactaa tcgagtgtag aggccaagac    9840
gaggcggcac ttcagtcccg aatagaggaa gtggtccgag tgttaactgc cgctggattg    9900
ccgttcggag ccaaggcagc tcagcctatg gcgatagacg cctacccctt tcaccatgac    9960
cagaagaacg ccaaggtctt ttgggatgtt aggcgcggac tgattccaat tgtgggtgcc   10020
gcgagggaac ctgggacttc gatgctgatt gaggatgtgg cttgtcccgt tgacaagctg   10080
gccgacatga tgatcgacct catcgacatg tttcaacgac atggctacca tgatgcgtca   10140
tgctttggcc acgcactgga gggtaacttg cacctcgttt tctcccaggg ctttaggaac   10200
aaggaggaag ttcagcgctt ctcagacatg atggaggaga tgtgccacct ggttgcgaca   10260
aagcattccg gaagccttaa gggcgaacat ggaaccggga gaaatgtcgc acccttcgtg   10320
gagatggagt ggggaaacaa ggcctatgag ctgatgtggg agctgaaggc tctgtttgat   10380
ccaagccaca ccctcaatcc cggtgtcatc ctgaaccggg accaagatgc gcacattaag   10440
tttttgaaac ccagccctgc cgcgagccca atcgtcaatc ggtgcatcga atgcgggttt   10500
tgtgagagca actgcccatc tagggacatc acactcacac ctcgccaacg gatcagcgtg   10560
tacagggaaa tgtatcgctt gaaacaactt gggccgggag cctctgagga agagaagaag   10620
cagctggctg cgatgtcgag ctcttacgct tacgatggcg agcaaacgtg tgccgctgat   10680
gggatgtgcc aagagaagtg cccagtgaag atcaacaccg cgacctcat taagagcatg   10740 cgggccgagc acatgaaaga agagaagaca gcctctggta tggcggactg gcttgctgcg   10800 aatttttggcg tgatcaactc caatgtccct cgtttcctga atatcgtgaa cgcgatgcac   10860
tccgtggttg gtagcgcccc cttaagtgcc atttcacgcg cactgaacgc agctacgaac   10920
```

```
cacttcgtcc cagtttggaa cccatacatg ccgaaaggag cggcacccTt aaaagttcca   10980
gcgccgccag ctccggccgc tgccgaagcc tcgggaatcc ctaggaaagt cgtttacatg   11040
ccctcctgcg tgacgagaat gatgggtcca gcagcttcgg acactgagac tgctgccgtc   11100
catgagaaag tcatgtcgct cttcgggaag gctggctacg aagtgatcat acctgagggc   11160
gttgcgagcc aatgctgcgg gatgatgttc aattcccggg gatttaagga cgcagcggcc   11220
tcaaaaggtg ccgaacttga agcggctttg ctgaaggcct ccgataacgg gaagatcccg   11280
atcgtgatcg acacttcccc atgccttgcc caggtcaaat cgcaaattag cgagccgagt   11340
ctccgctttg ccctctacga gccagtcgag tttataaggc acttcctcgt cgataagctc   11400
gaatggaaga aggtccgtga tcaggtcgct attcacgtgc cgtgttcctc gaagaagatg   11460
gggatcgagg aatcgttcgc gaaattggcg ggcttgtgtg cgaatgaagt ggtcccaagc   11520
ggaatacccT gctgtggtat ggcgggagat cgtggaatgc gattccctga gctcacggga   11580
gcgtctctgc aacatctcaa tctcccgaag acctgcaagg acggttactc tactagccgc   11640
acttgcgaga tgtccctctc taaccacgcg gggatcaatt tccgcggact tgtctatctg   11700
gtcgacgaag ctaccgcccc aaaaaagcaa gcggctgccg caaaaacggc gtgattgcta   11760
gcacgcgttt aattaaattt aaatggcgcg ccgaagcaga tcgttcaaac atttggcaat   11820
aaagtttctt aagattgaat cctgttgccg gtcttgcgat gattatcata taatttctgt   11880
tgaattacgt taagcatgta ataattaaca tgtaatgcat gacgttattt atgagatggg   11940
tttttatgat tagagtcccg caattataca tttaatacgc gatagaaaac aaaatatagc   12000
gcgcaaacta ggataaatta tcgcgcgcgg tgtcatctat gttactagat cggaattcga   12060
tatcattacc ctgttatccc taaagcttat taatataact tcgtatagca tacattatac   12120
gaagttatgt ttcctacgca gcaggtctca tcaagacgct ctacccgagt aacaatctcc   12180
aggagatcaa ataccttccc aagaaggtta agatgcagt caaaagattc aggactaatt   12240
gcatcaagaa cacagagaaa gacatatttc tcaagatcag aagtactatt ccagtatgga   12300
cgattcaagg cttgcttcat aaaccaaggc aagtaataga gattggagtc tctaaaaagg   12360
tagttcctac tgaatctaag gccatgcatg gagtctaaga ttcaaatcga ggatctaaca   12420
gaactcgccg tgaagactgg cgaacagttc atacagagtc ttttacgact caatgacaag   12480
aagaaaatct tcgtcaacat ggtggagcac gacactctgg tctactccaa aaatgtcaaa   12540
gatacagtct cagaagacca aagggctatt gagacttttc aacaaggat aatttcggga   12600 aacctcctcg gattccattg cccagctatc tgtcacttca tcgaaaggac agtagaaaag   12660
gaaggtggct cctacaaatg ccatcattgc gataaaggaa aggctatcat tcaagatgcc   12720
tctgccgaca gtggtcccaa agatggaccc ccacccacga ggagcatcgt ggaaaaagaa   12780
gacgttccaa ccacgtcttc aaagcaagtg gattgatgtg acatctccac tgacgtaagg   12840
gatgacgcac aatcccacta tccttcgcaa gaccctTcct ctatataagg aagttcattt   12900
catttggaga ggacacgctg aaatcaccag tctctctcta taaatctatc tctctctcta   12960
taacaatgga cccagaacga cgcccggccg acatccgccg tgccaccgag gcggacatgc   13020
cggcggtctg caccatcgtc aaccactaca tcgagacaag cacggtcaac ttccgtaccg   13080
agccgcagga accgcaggag tggacggacg acctcgtccg tctgcgggag cgctatccct   13140
ggctcgtcgc cgaggtggac ggcgaggtcg ccggcatcgc ctacgcgggc ccctggaagg   13200
cacgcaacgc ctacgactgg acggccgagt cgaccgtgta cgtctccccc cgccaccagc   13260
ggacgggact gggctccacg ctctacaccc acctgctgaa gtccctggag gcacagggct   13320
```

```
tcaagagcgt ggtcgctgtc atcgggctgc ccaacgaccc gagcgtgcgc atgcacgagg    13380
cgctcggata tgccccccgc ggcatgctgc gggcggccgg cttcaagcac gggaactggc    13440
atgacgtggg tttctggcag ctggacttca gcctgccggt accgcccgt ccggtcctgc    13500 ccgtcaccga gatctgagat cacccgttct aggatccgaa gcagatcgtt caaacatttg    13560
gcaataaagt ttcttaagat tgaatcctgt tgccggtctt gcgatgatta tcatataatt    13620
tctgttgaat tacgttaagc atgtaataat taacatgtaa tgcatgacgt tatttatgag    13680
atgggttttt atgattagag tcccgcaatt atacatttaa tacgcgatag aaaacaaaat    13740
atagcgcgca aactaggata aattatcgcg cgcggtgtca tctatgttac tagatcgaaa    13800
cataacttcg tatagcatac attatacgaa gttatatgga tctcgaggca ttacggcatt    13860
acggcactcg cgagggtccc aattcgagca tggagccatt tacaattgaa tatatcctgc    13920
cg                                                                   13922
```

PLANTS WITH IMPROVED PHOTOSYNTHETIC CARBON FIXATION CAPACITY

CROSS REFERENCE TO RELATED APPLICATIONS

This application is a national stage application under 35 U.S.C. § 371 of PCT Application No. PCT/EP15/079649, filed Dec. 14, 2015, which claims the benefit of European Patent Application Serial No. 14198663.8, filed Dec. 17, 2014, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS14-2011-WO1_ST25.txt," created on Dec. 10, 2015, and having a size of 78 kilobytes and is filed concurrently with the specification. The sequence listing contained in this ASCII formatted document is part of the specification and is herein incorporated by reference in its entirety.

FIELD OF THE INVENTION

The inventions herein described relate to the agricultural field, more specifically to methods of improving photosynthesis in plants, including crop plants as well as plants obtained by such methods. Specifically, the invention relates to plants with increased ribulose-1,5-bisphosphate (RuBP) regeneration capacity during the Calvin cycle through increased expression of sedoheptulose 1,7 biosphosphatase, in combination with reduced photo-respiratory losses through expression of glycolate catabolizing enzymes. Such plants have a greater growth rate and/or improved biomass and/or increased carbon fixation compared to untreated plants, or plants comprising only one of the characteristics above described.

BACKGROUND ART

Crop productivity is influenced by many factors, among which are, on the one hand factors influencing the capacity of the plant to produce biomass (photosynthesis, nutrient and water uptake), and on the other hand factors influencing the capacity of the plant to resist certain stresses, like biotic stresses (insects, fungi, viruses . . . ) or abiotic stresses (drought, salinity . . . ).

One important factor influencing the production of biomass is photosynthesis. Photosynthesis is the mechanism through which plants capture atmospheric carbon dioxide and fix it into carbon skeletons that are used for biosynthesis. The vast majority of plant species fix atmospheric $CO_2$ using the enzyme ribulose bisphosphate carboxylase/oxygenase (Rubisco) in the Calvin-Benson cycle. The first stable product of this cycle is a three-carbon compound, phosphoglycerate (3-PGA), and thus, this process is referred to as the C3-cycle. Regeneration of the RuBP involves eight enzymes including sedoheptulose 1,7-bisphosphatase (SBPase). Small reductions in the SBPase resulted in a decrease in $CO_2$ fixation and growth, identifying this enzyme as a control point in the C3 cycle. A major problem with the C3 cycle is the enzyme Rubisco. Rubisco is not only an inefficient enzyme with a low turnover number, but it also catalyses two competing reactions: carboxylation and oxygenation of RuBP. The oxygenation reaction directs the flow of carbon through the photorespiratory pathway and can result in losses of between 25-30% of the carbon fixed. Environmental variables, such as high temperature and drought, can result in an increase in the oxygenase reaction. (for a review see Raines 2011 Plant Physiology vol 155, pp 36-42).

To improve crop photosynthesis, one strategy is to overcome the oxygenase reaction of Rubisco by creating a photorespiratory bypass in the chloroplast through expression of glycolate catabolizing enzymes.

WO2003/100066 relates to a method for the production of plants with suppressed photorespiration and improved $CO_2$ fixation. In particular, the invention relates to a re-use of phosphoglycolate produced in photorespiration. The reaction product will be converted to a component that may be reintegrated into the plant assimilatory metabolism inside the chloroplast. This is accomplished by the transfer of genes derived from glycolate-utilizing pathways from bacteria, algae, plants and/or animals including humans into the plant nuclear and/or plastidial genome. The method leads to a reduction of photorespiration in C3 plants and by this will be of great benefit for food production especially but not exclusively under non-favourable growth conditions.

WO2010/012796 relates to a method for stimulating the growth of the plants and/or improving the biomass production and/or increasing the carbon fixation by the plant comprising introducing into a rice plant cell, rice plant tissue or rice plant one or more nucleic acids, wherein the introduction of the nucleic acid(s) results inside the chloroplast of a de novo expression of one or more polypeptides having the enzymatic activity of a glycolate dehydrogenase.

WO2011/095528 relates to a method for stimulating the growth of the plants and/or improving the biomass production and/or increasing the carbon fixation by the plant comprising introducing into a plant cell, plant tissue or plant one or more nucleic acids, wherein the introduction of the nucleic acid(s) results inside the chloroplast of a de novo expression of one or more polypeptides having the enzymatic activity of a glycolate dehydrogenase made up from translationally fused subunits of bacterial multi-subunit glycolate dehydrogenase enzymes.

Kebeish et al. (2007 Nature Biotechnology Vol 25, pp 593-599) reported that the photorespiratory losses in *Arabidopsis thaliana* can be alleviated by introducing into chloroplasts a bacterial pathway for the catabolism of the photorespiratory substrate, glycolate. The authors first targeted the three subunits of *Escherichia coli* glycolate dehydrogenase to *Arabidopsis thaliana* chloroplasts and then introduced the *Escherichia coli* glyoxylate carboligase and *Escherichia coli* tartronic semialdehyde reductase to complete the pathway that converts glycolate to glycerate in parallel with the endogenous photorespiratory pathway. This step-wise nuclear transformation with the five *Escherichia coli* genes leads to *Arabidopsis* plants in which chloroplastic glycolate is converted directly to glycerate. These transgenic plants grew faster, produced more shoot and root biomass, and contained more soluble sugars. An effect was also visible but to a lesser extent in *Arabidopsis* plants that overexpressed only the three subunits of the glycolate dehydrogenase.

Nölke et al. (2014 Plant biotechnology Journal, Vol 12, pp 734-742) described the expression of a recombinant glycolate dehydrogenase polyprotein in potato (*Solanum tuberosum*) plastids which strongly enhances photosynthesis and tuber yield.

Another strategy to try to improve crop photosynthesis could be the overexpression of sedoheptulose 1,7-bisphosphatase to increase the RuBP regenerative capacity of the Calvin cycle.

WO00/70062 describes expression of sedoheptulose 1,7-bisphosphatase in transgenic plants. Sedoheptulose 1,7-bisphosphatase (SBPase) is an enzyme catalyzing the reaction converting sedoheptulose 1,7-bisphosphate into sedoheptulose 7-phosphate. This enzyme is located in the chloroplast in leaves and stems. Overexpression of SBPase in transgenic plants is provided to improve plant yield by increasing leaf starch biosynthetic ability and sucrose production. Deregulated variants of the enzymes are also provided.

Miyagawa et al. (2001 Nature Biotechnology Vol 19 pp 965-969) reported that overexpression of cyanobacterial fructose 1,6-/sedoheptulose 1,7-bisphosphatase in tobacco enhances photosynthesis and growth.

Lefebvre et al. (2005 Plant Physiology Vol. 138 pp 451-460) reported that increased sedoheptulose 1,7-bisphosphatase activity in transgenic tobacco plants stimulates photosynthesis and growth at an early stage in development.

Lawson et al. (2006 Plant, Cell and Environment Vol 29, pp 48-58) described that decreasing SBPase alters growth and development in transgenic tobacco plants.

Tamoi et al (2006 Plant Cell Physiol, 47: 380-390) described the contribution of Fructose-1,6-bisphosphatase and Sedoheptulose-1,7-bisphosphatase to the photosynthetic rate and carbon flow in the calvin cycle in transgenic plants.

Feng et al. (2007 Plant Cell Reporter Vol 26, pp 1635-1646) reported overexpression of SBPase enhancing photosynthesis under high temperature stress in transgenic rice plants. In contrast to the results with tobacco, increasing SBPase activity in rice did not lead to increasing photosynthesis or growth. However, when the plants were subjected to heat or salt stress, higher photosynthesis rates were found in the transgenic plants, compared to wild-type controls under similar conditions.

There is therefore still a need for an efficient method for increasing the carbon fixation in plants, particularly crop plants, which increases the photosynthetic carbon assimilation and stimulates the growth of the plant and/or improves biomass and/or seed production.

SUMMARY OF THE INVENTION

In one embodiment of the invention, a method is provided for improving the assimilation of carbon in a plant comprising the steps of providing cells of the plant with increased RuBP regeneration capacity; and providing cells of the plant with glycolate catabolizing enzymes. Conveniently this may be achieved by inserting into the genome of a plant a nucleic acid encoding an enzyme comprising sedoheptulose 1,7-bisphosphatase activity, from a source heterologous with respect to the plant into which the nucleic acid is inserted, such as a plant species heterologous with respect to the plant into which the structural nucleic acid is inserted, and inserting into the genome of a plant one or more nucleic acids encoding one or more polypeptides having the enzymatic activity of glycolate dehydrogenase, wherein the one or more polypeptides are located in chloroplasts of the plants.

The nucleic acid encoding an enzyme comprising sedoheptulose 1,7-bisphosphatase activity may be operably linked to a plant-expressible promoter, such as the promoter region of the ribulose-bisphosphate carboxylase small subunit gene of *Oryza sativa*, and optionally to a 3' end region involved in transcription termination and/or polyadenylation. The enzyme comprising sedoheptulose 1,7-bisphosphatase activity may further comprise an amino acid sequence targeting the enzyme comprising sedoheptulose 1,7-bisphosphatase activity to the chloroplast or the chloroplast membrane or the nucleic acid encoding an enzyme comprising sedoheptulose 1,7-bisphosphatase activity may be integrated in the chloroplast genome of cells of the plant.

The one or more nucleic acids encoding one or more polypeptides having the enzymatic activity of glycolate dehydrogenase may be derived from the *E. coli* glc operon, such as polypeptides comprising an amino acid sequence having at least 60% sequence identity to the amino acid sequence of SEQ ID No 3, SEQ ID No 4 and SEQ ID No 5, optionally forming a multi-subunit fusion protein. The polypeptide may also be a polypeptide having the enzymatic activity of a glycolate dehydrogenase derived from *Chlamydomonas* or *Synechocystis*, including a polypeptide having at least 60% sequence identity to the amino acid sequence of SEQ ID NO 6, SEQ ID No 7 or SEQ ID No 8. In another embodiment, the polypeptide may be an *Arabidopsis* glycolate dehydrogenase, including a polypeptide comprising an amino acid sequence having at least 60% sequence identity to the amino acid sequence of SEQ ID NO 9. Glycolate dehydrogenase peptides may further comprise an amino acid sequence targeting the enzyme or subunits to the chloroplast or the chloroplast membrane or the nucleic acids encoding one or more polypeptides having glycolate dehydrogenase activity are integrated in the chloroplast genome of cells of the plant. Again, the one or more nucleic acid encoding one or more polypeptides having glycolate dehydrogenase activity may be operably linked to a plant-expressible promoter, such as the promoter region of the ribulose-bisphosphate carboxylase small subunit gene of *Oryza sativa* or the promoter region of the cytosolic fructose 1,6 bisphosphatase gene of *Oryza sativa* and optionally to a 3' end region involved in transcription termination and/or polyadenylation. The plant may be a monocotyledonous plant, a dicotyledonous plant or a gymnosperm, including wheat, rice, maize, *sorghum*, millet, rye, oats, sugarcane, cotton, sugarbeet, *Brassica* plants, including *B. napus, B. oleracea, B. juncea, B. rapa* or *B. carinata*.

In another embodiment, the invention provides plant cell, plant parts, plants or seed comprising nucleic acid encoding an enzyme comprising sedoheptulose 1,7-bisphosphatase activity; and one or more nucleic acids encoding one or more polypeptides having the enzymatic activity of glycolate dehydrogenase, wherein the one or more polypeptides are located in chloroplasts of the plants, as herein described.

In yet another embodiment, the invention relates to a food product obtained from a plant or plant part or seed a herein described.

The invention also provides the simultaneous use of a nucleic acid encoding an enzyme comprising sedoheptulose 1,7-bisphosphatase activity as herein described and one or more nucleic acids encoding one or more polypeptides having the enzymatic activity of glycolate dehydrogenase, as herein described, for improving the assimilation of carbon in a plant, or for increasing the growth rate or for improving biomass production of a plant.

DETAILED DESCRIPTION OF DIFFERENT EMBODIMENTS

As used herein "biomass" is the quantity of matter produced by individual plants, or by surface area on which the plants are grown. Several parameters may be measured in order to determine the increase of biomass production. Examples of such parameters are the height of the plant, surface of the leaf blade, shoot dry weight, root dry weight, seed number, seed weight, seed size, . . . . In that respect, seed production, or seed yield, is one specific indicator of biomass. Seed production or seed yield can be measured per individual plant or per surface area where the plants are grown. These parameters are generally measured after a determined period of growth in soil or at a specific step of growth, for example at the end of the vegetative period, and compared between plants transformed with one or more nucleic acids according to the invention and plants not transformed with such one or more nucleic acids.

The increase of carbon fixation by the plant can be determined by measuring gas exchange and chlorophyll fluorescence parameters. A convenient methodology, using the LI-6400 system (Li-Cor) and the software supplied by the manufacturer, is described in R. Kebeish et al., 2007, and is incorporated herein by reference.

The current invention is based on the observation that photosynthetic assimilation of carbon in plants can be further increased by simultaneously providing cells of such plants with increased RuBP regeneration capacity and providing the chloroplasts of such cells with glycolate catabolizing enzymes to bypass photorespiration.

Increasing the RuBP regeneration capacity can be conveniently achieved by inserting into the genome of a plant cell a nucleic acid encoding an enzyme comprising sedulose 1,7-bisphosphatase activity. Methods for expressing SBPase encoding enzymes in plants have been described e.g. in WO 00/70062 (herein incorporated by reference).

As used herein, "inserting" or "introducing" a nucleic acid into the plant genome or "providing" a nucleic acid to a plant cell should be understood as encompassing all methods available in the art to provide a plant cell comprising the nucleic acid, whether such introduction is achieved by plant transformation methods or by crossing the recipient plant with a donor plant into which the nucleic acid of interest was previously introduced. Other methods of transferring a nucleic acid from a donor plant to a recipient plants include e.g. protoplast fusion followed by regeneration of the fused protoplasts.

In the context of the present invention the term "genome" includes bot the nuclear genome as well as the plastid genome. It will be clear that the methods of transformation used are of minor relevance to the current invention. Transformation of plants is now a routine technique. Advantageously, any of several transformation methods may be used to introduce the nucleic acid/gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens et al. (1982) Nature 296: 72-74; Negrutiu et al. (1987) Plant. Mol. Biol. 8: 363-373); electroporation of protoplasts (Shillito et al. (1985) Bio/Technol. 3: 1099-1102); microinjection into plant material (Crossway et al. (1986) Mol. Gen. Genet. 202: 179-185); DNA or RNA-coated particle bombardment (Klein et al. (1987) Nature 327: 70) infection with (non-integrative) viruses and the like. Transgenic plants can also be produced by using needle-like crystals ("whiskers") of silicon carbide; viral-mediated transformation; *Agrobacterium*-, *Rhizobium*-, *Mesorhizobium*- and *Sinorizobium*-mediated transformation. See, for example, U.S. Pat. Nos. 5,405,765; 5,472,869; 5,538,877; 5,538,880; 5,550,318; 5,641,664; 5,736,369; 5,736369; and US patent applications 2005/0289672 and 2005/0289667.

In the case of canola or other *Brassica* oilseed rape plants, a suitable transformation method is that disclosed in De Block et al. (Plant Physiol. (1989) 91: 694-701).

Two major methods are currently used in soybean transformation. The first method utilizes particle bombardment, advantageously of embryogenic calluses, cell cultures on a solid or in suspension, or other proliferative embryogenic tissues (Trick & Finer, 1998; Maughan et al, 1999; Santarem & Finer, 1999; Droste et al, 2002), while the second method involves *Agrobacterium*-mediated transformation of organogenic tissue, such as cotyledonary node tissues (Zhang et al, 1999; Clemente et al, 2000; Olhoft & Somers, 2001; Olhoft et al, 2001), or tissue derived from mature soybean seeds (U.S. Pat. No. 7,473,822; EP10356036.3). WO2011/095460 also describes soybean transformation methods, using HPPD inhibitors as selective agents.

*Agrobacterium*-mediated transformation of cotton has been described e.g. in U.S. Pat. No. 5,004,863 or in U.S. Pat. No. 6,483,013 and cotton transformation by particle bombardment is reported e.g. in WO 92/15675. Other suitable cotton transformation methods are disclosed e.g. in WO 00071733 and U.S. Pat. No. 5,159,135, which disclosures are incorporated by reference herein.

*Agrobacterium* mediated transformation of *Triticum* plants, including wheat has been described e.g. in WO2011/013764.

An efficient *Agrobacterium*-mediated transformation method for corn (maize), using pre-incubation of compact embryogenic calli in plant phenolic compounds has been described in WO 98/37212.

For rice, *Agrobacterium*-mediated transformation (Hiei et al., 1994, and Hiei et al., 1997, incorporated herein by reference), electroporation (U.S. Pat. No. 5,641,664 and U.S. Pat. No. 5,679,558, incorporated herein by reference), or bombardment (Christou et al., 1991, incorporated herein by reference) could be advantageously performed. A suitable technology for transformation of monocotyledonous plants, and particularly rice, is described in WO 92/09696.

Methods for chloroplast transformation are also well known in the art, including those described in WO02/055651, WO01/42441, WO02/057466, WO2004/015115, WO2004/016793, WO01/64023, WO01/81605, WO2004/005480, WO2004/035734, WO97/32977, WO00/39313, WO2010/061186, WO2006/072607, WO2007/031547, WO2008/003666, WO06/108830 or WO2010/079117.

Each of referenced transformation methods (nuclear or chloroplastic) is expressly incorporated herein by reference in entirety.

To achieve localization of nuclearly expressed polypeptides, such as SBPase polypeptide(s) and/or glycolate dehydrogenase polypeptide(s) in plastids of cells, particularly in chloroplasts of the plant cells, the coding region of the SBPase polypeptide(s) may be operably linked to a plastid targeting signal, particularly a chloroplast targeting signal. Thus, a nucleic acid which encodes a chloroplast transit peptide, such as a heterologous chloroplast transit peptide may be introduced at the 5' end of the nucleic acid sequence encoding an SBPase or glycolate dehydrogenase polypeptide(s), with this transit peptide sequence being arranged between the promoter region and the nucleic acid encoding the SBPase or glycolate dehydrogenase polypeptide so as to permit expression of a transit peptide/SBPase or transit peptide/glycolate dehydrogenase fusion protein. The transit peptide allows to direct the fused protein into the plastids, more especially the chloroplasts, with the fusion protein being cleaved between the transit peptide and the polypeptide of interest when the latter enters the plastid. The transit peptide may be a single peptide, such as an EPSPS transit peptide (described in U.S. Pat. No. 5,188,642) or a transit peptide of the plant ribulose bisphosphate carboxylase/oxygenase small subunit (RuBisCO ssu), for example the chloroplast transit peptide derived from the ribulose-1,5-bisphosphate carboxylase small subunit gene from *Solanum tuberosum* (GenBank: G68077, amino acids 1-58), where appropriate including a few amino acids of the N-terminal part of the mature RuBisCO ssu (see e.g. EP 189 707), or the chloroplast targeting peptide derived from the potato rbcS1 gene (gi21562). A transit peptide may be the whole naturally occurring (wild-type) transit peptide, a functional fragment thereof, or a functional mutant thereof. It can also be a chimeric transit peptide wherein at least two transit peptides are associated to each other or wherein parts of different transit peptides are associated to each other in a functional manner. One example of such chimeric transit peptide comprises a transit peptide of the sunflower RuBisCO ssu fused to the N-terminal part of the maize RuBisCO ssu, fused to the transit peptide of the maize RuBisCO ssu, as described in patent EP 508 909. The person skilled in the art will be able to construct nucleic acid suitable for performing the invention comprising a nucleic acid encoding a mature (i.e. without transit peptide) SBPase or glycolate dehydrogenase polypeptide, which may be optionally optimized for expression in particular crop plants, such as for expression in wheat, and wherein the first ATG codon, if any, may or may not be deleted, operably-linked to a chloroplast transit peptide.

For the purpose of expressing the nucleic acid(s) which encode the polypeptide(s) having the enzymatic activity as required for the present invention in plant cells, any convenient regulatory sequences can be used. The regulatory sequences will provide transcriptional and translational initiation as well as termination regions, where the transcriptional initiation may be constitutive or inducible. The coding region can be operably linked to such regulatory sequences. Suitable regulatory sequences are represented by the constitutive CaMV 35S promoter. Alternatively, the constitutive ubiquitin promoter can be used, in particular the maize ubiquitin promoter (GenBank: gi19700915). Examples for inducible promoters represent the light inducible promoters of the small subunit of RuBisCO and the promoters of the "light harvesting complex binding protein (lhcb)". Advantageously, the promoter region of the Gos2 gene of *Oryza sativa* including the 5' UTR of the GOS2 gene with intron (de Pater et al., 1992), the promoter region of the RuBisCO small subunit gene of *Oryza sativa* (Kyozuka J. et al., 1993), or the promoter region of the actin 1 gene of *Oryza sativa* (McElroy D. et al., 1990) may be used. Other promoters which may be used include the promoter region of the RuBisCO small subunit gene of *Oryza sativa* as described by Nomura et al. 2000, Plant Molecular Biology 44(1) 99-106 or as represented in SEQ ID No 12 from nucleotide 2010-4759 (counter clockwise). Another suitable promoter is the promoter region of the cytolsolic fructose 1,6-bisphosphatase gene of *Oryza sativa* as described by Si et al. 2003 (Acta Botanica Sinica 45, 359-364) or as described in SEQ ID No 11 from nucleotide 75 to nucleotide 1272.

According to the invention, use may also be made, in combination with the promoter, of other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed 1990, for example, or introns such as the adh1 intron of maize or intron 1 of rice actin.

As a regulatory terminator or polyadenylation sequence, use may be made of any 3' end region function in plant cells, such as for example the nos terminator of *Agrobacterium tumefaciens*, of viral origin, such as for example the CaMV 35S terminator, or of plant origin, such as for example a histone terminator as described in Application EP 0 633 317.

Sedoheptulose-bisphosphatase (also sedoheptulose-1,7-bisphosphatase or SBPase) (EC 3.1.3.37) is an enzyme that catalyzes the removal of a phosphate group from sedoheptulose 1,7-bisphosphate to produce sedoheptulose 7-phosphate. This enzyme is involved in the regeneration of 5-carbon sugars during the Calvin cycle. SBPase is activated in the presence of light through a ferredoxin/thioredoxin system. The reduced thioredoxin is used to reduced a cysteine-cysteine disulfide bond in SBPase to a dithiol, which converts the SBPase into its active form. $Mg2+$ concentration has a significant impact on the activity of SBPase and the rate of the reactions it catalyzes. SBPase is subject to negative feedback regulation by sedoheptulose-7-phosphate and inorganic phosphate, the products of the reaction it catalyzes. SBPase is found across many species, in addition to being universally present in photosynthetic organism.

SBPase activity can be determined by a phosphate release assay as described by Lefebvre et al. 2005 or as described with modifications by Liu et al. 2012 (Molecular Plant Advance pages 1-18).

A suitable SBPase coding region could be the coding sequence of the sedoheptulose 1,7—gene of *Oryza sativa* as described by Feng et al. 2007 (Plant Cell Reporter 26, 1635-1646) or as described in SEQ ID No 12 from nucleotide position 362 to 1540 (counterclock wise). Of course, any nucleotide sequence encoding a polypeptide having the amino acid sequence of SEQ ID No 2 can equally be used.

The nucleic acid molecules encoding SBPases as described herein may be modified, for example, by codon optimization to facilitate expression in heterologous cells. This type of modification changes or alters the nucleotide sequence that encodes a protein of interest to use, throughout the sequence, codons that are more-commonly used in the transgenic expression host cell. In addition, changes may be made to the nucleotide sequence that encodes the protein to adjust the relative concentration of A/T and G/C base pairs to ratios that are more similar to those of the expression host.

Moreover, numerous other SBPase polypeptide(s) are known in the art, and nucleic acid molecules encoding such other SBPase polypeptide(s) may also be used in the context of the current invention. The amino acid sequences of these SBPase polypeptide(s) can be found in publicly available databases and include the following: (*Zea mays*) Accession: NP_001148402.1/GI: 226506366; (*Triticum aestivum*) Accession: P46285.1/GI: 1173347; (*Arabidopsis thaliana*) Accession: P46283.1/GI: 1173345; (*Spinacia oleracea*) Accession: 020252.1/GI: 3914940; (*Arabidopsis thaliana*) Accession: AEE79443.1/GI: 332645922; (*Arabidopsis thaliana*) Accession: NP_191139.1/GI: 15228194; (chloroplast/*Arabidopsis thaliana*) Accession: AAB33001.1/GI: 786466; (*Arabis alpina*) Accession: KFK34828.1/GI: 674242063 (*Oryza sativa Japonica* Group) Accession: BAF14207.1/GI: 113563864; (*Sorghum bicolor*) Accession: EES01767.1/GI: 241928622; (*Cucumis sativus*) Accession: ACQ82818.1/GI: 229597543; (*Oryza sativa Japonica* Group) Accession: NP_001052293.1/GI: 115457386; (*Sor-

*ghum bicolor*) Accession: XP_002456647.1/GI: 242055003; (*Solanum lycopersicum*) Accession: NP_001234585.1/GI: 350538149; (*Triticum aestivum*) Accession: CDM85031.1/GI: 669030491; (*Cucumis sativus*) Accession: NP_001267658.1/GI: 525507240; (*Morus alba* var. *multicaulis*) Accession: ABK76304.1/GI: 118175929; (*Solanum lycopersicum*) Accession: ACR46521.1/GI: 238563983; (*Marchantia polymorpha*) Accession: ABF68592.1/GI: 99903817; (*Triticum aestivum*) Accession: CAA46507.1/GI: 14265; (*Gossypium arboreum*) Accession: KHG28838.1/GI: 728849395; (*Brachypodium distachyon*) Accession: XP_003564625.1/GI: 357125896; (*Nelumbo nucifera*) Accession: XP_010256671.1/GI: 720002409; (*Morus notabilis*) Accession: XP_010093027.1/GI: 703086526 (*Eucalyptus grandis*) Accession: XP_010031259.1/GI: 702473166; (*Nicotiana sylvestris*) Accession: XP_009776701.1 GI: 698578260; (*Nicotiana sylvestris*) Accession: XP_009780073.1/GI: 698454000; (*Nicotiana tomentosiformis*) Accession: XP_009622770.1/GI: 697137344; (*Nicotiana tomentosiformis*) Accession: XP_009590435.1/GI: 697100291; (*Musa acuminata* subsp. *malaccensis*) Accession: XP_009398831.1/GI: 694997329; (*Pyrus×bretschneideri*) Accession: XP_009341715.1/GI: 694428277; (*Pyrus×bretschneideri*) Accession: XP_009361829.1/GI: 694366289; (*Pyrus×bretschneideri*) Accession: XP_009351012.1/GI: 694320367; (*Pyrus× bretschneideri*) Accession: XP_009351006.1/GI: 694320364; (*Pyrus×bretschneideri*) Accession: XP_009344459.1 GI: 694318830; (*Brassica rapa*) Accession: XP_009116278.1/GI: 685364140; (*Brassica rapa*) Accession: XP_009103972.1/GI: 685332510; (*Brassica rapa*) Accession: XP_009103971.1/GI: 685332508; (*Brassica rapa*) Accession: XP_009139137.1/GI: 685296600; (*Brassica rapa*) Accession: XP_009139136.1/GI: 685296598; (*Brassica rapa*) Accession: XP_009139135.1/GI: 685296596; (*Nicotiana tabacum*) Accession: AI199841.1/GI: 671775216; (*Phoenix dactylifera*) Accession: XP_008775070.1/GI: 672189771; (*Phoenix dactylifera*) Accession: XP_008785431.1/GI: 672124109; (*Theobroma cacao*) Accession: XP_007009096.1/GI: 590562472; (*Cucumis melo*) Accession: XP_008463213.1/GI: 659126497; (*Malus domestica*) Accession: XP_008383089.1/GI: 657982110; (*Malus domestica*) Accession: XP_008372025.1/GI: 657960888; (*Malus domestica*) Accession: XP_008381958.1/GI: 657945883; (*Medicago truncatula*) Accession: AES71104.1/GI: 355489901; (*Prunus mume*) Accession: XP_008234053.1/GI: 645256667; (*Prunus mume*) Accession: XP_008226111.1/GI: 645239407; (*Theobroma cacao*) Accession: EOY17906.1/GI: 508726009; (*Brassica rapa* subsp. *chinensis*) Accession: AHY18974.1/GI: 619835283; (*Morus notabilis*) Accession: EXB53355.1/GI: 587863593; (*Oryza brachyantha*) Accession: XP_006664812.1/GI: 573965402; (*Glycine max*) Accession: XP_003552524.1/GI: 356568652; (*Glycine max*) Accession: XP_003538446.1/GI: 356539931; (*Populus trichocarpa*) Accession: XP_002316235.1/GI: 224112589; (*Citrus sinensis*) Accession: XP_006486375.1/GI: 568866045; (*Solanum tuberosum*) Accession: XP_006355654.1/GI: 565378420; (*Populus trichocarpa*) Accession: EEF02406.1/GI: 222865275; (*Genlisea aurea*) Accession: EPS64973.1/GI: 527195911; (*Setaria italica*) Accession: XP_004970606.1/GI: 514784500; (*Cicer arietinum*) Accession: XP_004503228.1/GI: 502137914; (*Aegilops tauschii*) Accession: EMT17623.1/GI: 475576723; (*Triticum urartu*) Accession: EMS67709.1/GI: 474425491; (*Fragaria vesca* subsp. *vesca*) Accession: XP_004307611.1/GI: 470143913; (*Fragaria vesca* subsp. *vesca*) Accession: XP_004294065.1/GI: 470115771; (*Arabidopsis lyrata* subsp. *lyrata*) Accession: EFH52595.1/GI: 297322174; (*Ricinus communis*) Accession: EEF31985.1/GI: 223530064; (*Vitis vinifera*) Accession: XP_002263049.1/GI: 225466690; (*Medicago truncatula*) Accession: XP_003600853.1/GI: 357461143; (*Arabidopsis thaliana*) Accession: AAM91137.1/GI: 22136118; (*Triticum aestivum*) Accession: CBH32512.1/GI: 300681420; (*Spinacia oleracea*) Accession: AAB81104.1/GI: 2529376; (*Arabidopsis lyrata* subsp. *lyrata*) Accession: XP_002876336.1/GI: 297816906; (*Oryza sativa* Indica Group) Accession: AAO22559.1/GI: 27804772 (*Oryza sativa* Indica Group) Accession: AAO22558.1/GI: 27804768 (*Arabidopsis thaliana*) Accession: AAK96860.1/GI: 15451178 (*Ricinus communis*) Accession: XP_002530415.1/GI: 255579134 (*Zea mays*) Accession: ACG31345.1/GI: 195619030 (*Marchantia polymorpha*) Accession: ABK00060.1/GI: 116582760 (*Arabidopsis thaliana*) Accession: CAB81605.1/GI: 7263568.

SBPases from green algae may also be used and include amino acid sequences as represented by (*Chlamydomonas reinhardtii*) Accession: P46284.1/GI: 1173346; (*Chlorella variabilis*) Accession: XP_005850770.1/GI: 552843189; (*Chlamydomonas reinhardtii*) Accession: CAA52439.1/GI: 515618; (*Chlamydomonas reinhardtii*) Accession: EDP04487.1/GI: 158278724; (*Chlamydomonas reinhardtii*) Accession: XP_001691997.1/GI: 159467635; (*Micromonas* sp. RCC299) Accession: ACO64947.1/GI: 226518956; (*Auxenochlorella protothecoides*) Accession: KFM29064.1/GI: 675356624; (*Bathycoccus prasinos*); Accession: XP_007512235.1/GI: 612393430; (*Coccomyxa subellipsoidea* C-169) Accession: XP_005642742.1/GI: 545353814; (*Ostreococcus tauri*) Accession: XP_003078456.1/GI: 308802285; (*Bathycoccus prasinos*) Accession: CC066323.1/GI: 424513701; (*Volvox carteri* f. *nagariensis*) Accession: EFJ52154.1/GI: 300267972; (*Volvox carteri* f. *nagariensis*) Accession: XP_002946928.1/GI: 302830724; (*Micromonas* sp. RCC299) Accession: XP_002503689.1/GI: 255080218; (*Chlamydomonas reinhardtii*) Accession: CAA74960.1/GI: 2342564; (*Chlamydomonas* sp. W80) Accession: BAA94305.1/GI: 7544134.

It could also be advantageous to use SBPases comprised in a polypeptide having multiple enzymatic activities such as Fructose-1,6-bisphosphatase class 1/Sedoheputulose-1,7-bisphosphatase (*Ostreococcus tauri*) Accession: CEF97347.1/GI: 693500974 Fructose-1,6-bisphosphatase class 1/Sedoheputulose-1,7-bisphosphatase (*Ostreococcus tauri*) Accession: CEF97908.1/GI: 693499856 Fructose-1,6-bisphosphatase class 1/Sedoheputulose-1,7-bisphosphatase (*Ostreococcus tauri*) Accession: CEF98908.1/GI: 693498312 Fructose-1,6-bisphosphatase class 1/Sedoheputulose-1,7-bisphosphatase (*Ostreococcus tauri*) Accession: CEG02024.1/GI: 693497067 Fructose-1,6-bisphosphatase class 1/Sedoheputulose-1,7-bisphosphatase (*Ostreococcus tauri*) Accession: CAL52685.1/GI: 116056396.

The invention may also use variants of the SBPase polypeptide(s) herein described. Variants include, but are not limited to, deletions, additions, substitutions, insertions of e.g. 1 to 20 amino acids, such as 1 to 10, or 1 to 5). The term "variant" is intended to mean substantially similar sequences. Naturally occurring allelic variants can be identified with the use of well-known molecular biology techniques, as, for example, with polymerase chain reaction (PCR) and hybridization techniques as herein outlined. Variant (nucleotide) sequences also include synthetically derived (nucleotide) sequences, such as those generated, for example, by using site-directed mutagenesis. Generally, amino acid sequence variants of SBPase polypeptide(s) described herein will have at least 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% sequence identity to the amino acid sequences of the SBPases explicitly described herein, and will retain SBPase activity. Variant SBPase polypeptide(s) may have at least 60% sequence identity to the amino acid sequence of SEQ ID No 2. Variant SBPase polypeptide(s) may have at least 95% sequence identity to the amino acid sequence of SEQ ID No 2. Generally, nucleotide sequence variants have at least 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% sequence identity to the nucleotide sequences encoding the SBPases described herein, and the encoded products retain SBPase activity. Variant nucleic acids encoding SBPase polypeptide(s) may have at least 60% sequence identity to the nucleotide sequence of SEQ ID No 1. Variant nucleic acids encoding SBPases may have at least 95% sequence identity to the nucleotide sequence of SEQ ID No 1.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. on the world wide web at ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

Variant SBPase encoding nucleic acids may be identified by hybridization. "Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions. "High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS. "Moderate stringency conditions" refers to conditions equivalent to hybridization in the above described solution but at about 60-62° C. Moderate stringency washing may be done at the hybridization temperature in 1×SSC, 0.1% SDS. "Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

The invention also requires the presence of one or more peptides having glycolate dehydrogenase activity, within the chloroplasts of the plant cells, in addition to increased SBPase activity.

glycolate dehydrogenase (EC 1.1.99.14) is an enzyme that catalyzes the chemical reaction:

glycolate+acceptor 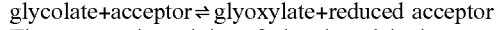 glyoxylate+reduced acceptor

The enzymatic activity of glycolate dehydrogenases can be defined by the oxidation of glycolate to form glyoxylate using organic cofactors, whereas glycolate oxidases, present for example in plant peroxisomes, use molecular oxygen as a cofactor and release hydrogen peroxide. Such clear distinction between glycolate dehydrogenases and glycolate oxidases based on the nature of the cofactors has not always been done, and as an example the *E. coli* glycolate dehydrogenase encoded by the glc operon was previously named glycolate oxidase (Bari et al., 2004, J. of Experimental Botany, Vol 55, No 397, 623-630). The glycolate dehydrogenase activity can be assayed according to Lord J. M. 1972 Biochim. Biophys. Acta 267, 227-237. Alternatively, complementation analysis with mutants of *E. coli* deficient in the three subunits forming active endogenous glycolate dehydrogenase may be performed. These mutants of *E. coli* are incapable of growing on glycolate as the sole carbon source. When the overexpression of an enzyme in these deficient mutants restores the growth of the bacteria on the medium containing glycolate as the sole carbon source, it means that this enzyme encodes a functional equivalent to the *E. coli* glycolate dehydrogenase. The method and means for the complementation analysis is described in Bari et al, 2004, and incorporated herein by reference. Polypeptides having the enzymatic activity of a glycolate dehydrogenase, and nucleic acids encoding them, have been identified from various sources, including bacteria, algae, and plants.

A suitable glycolate dehydrogenase coding region could be the glycolate dehydrogenase coding region of *Chlamydomonas* as described e.g. in SEQ ID No 10 from nucleotide 3666 to 6485. Again, any nucleotide sequence encoding a polypeptide comprising the amino acid sequence of SEQ ID No 6, or a truncated form thereof comprising the amino acid sequence of SEQ ID No 7, could be equally used.

Other suitable polypeptides having the enzymatic activity of a glycolate dehydrogenase are those encoded by the *E. coli* glc operon such as polypeptides which comprise the amino acid sequences of SEQ ID NOs: 3 (GlcD), 4 (GlcE) and 5 (GlcF).

Polypeptide(s) having the enzymatic activity of a glycolate dehydrogenase and derived from *Arabidopsis thaliana* or other higher plant sources may also be used.

The glycolate dehydrogenase activity involved in the method of the invention may be obtained by one or more polypeptides. When said activity is obtained through more than one polypeptides, the nucleic acids encoding the polypeptides may be transferred to plant cells in a single plasmid construct or independently in several constructs. The polypeptides corresponding to GlcD, E and F of the glc operon may also be provided as a fusion protein, as described in WO2011/095528.

The glycolate dehydrogenase may also be a chimeric glycolate dehydrogenase. The term "chimeric glycolate dehydrogenase" is intended to mean a glycolate dehydrogenase which is obtained by combining portions of enzymes from various origins, such as example the N-terminal portion of a first enzyme with the C-terminal portion of a second enzyme, so as to obtain a novel functional chimeric glycolate dehydrogenase, with each portion selected for its particular properties.

Numerous glycolate dehydrogenase polypeptides are known in the art from green plants including algae and may also be used in the context of the invention. The amino acid sequences of these glycolate dehydrogenase polypeptide(s) can be found in publicly available databases and include the following: (*Chlamydomonas reinhardtii*) Accession: EDP01639.1/GI: 158275864; (*Chlamydomonas reinhardtii*) Accession: XP_001695381.1/GI: 159474536; (*Chlamydomonas reinhardtii*) Accession: ABG36932.1/GI: 109659947; (*Micromonas* sp. RCC299) Accession: ACO67704.1/GI: 226521718; (*Micromonas* sp. RCC299) Accession: XP_002506446.1/GI: 255089048 (*Tetraselmis* sp. GSL018) Accession: JAC82740.1/GI: 654187807; (*Tetraselmis* sp. GSL018) Accession: JAC77648.1/GI: 654171420; (*Tetraselmis* sp. GSL018) Accession: JAC73922.1/GI: 654156881; (*Tetraselmis* sp. GSL018) Accession: JAC70698.1/GI: 654143314; (*Tetraselmis* sp. GSL018) Accession: JAC65595.1/GI: 654119087; (*Tetraselmis* sp. GSL018) Accession: JAC65376.1/GI: 654117941; (*Coccomyxa subellipsoidea* C-169) Accession: XP_005648725.1/GI: 545367841; (*Coccomyxa subellipsoidea* C-169) Accession: EIE24181.1/GI: 384250702; (*Arabidopsis thaliana*) Accession: Q9LSV0.1/GI: 75274028; (*Arabidopsis thaliana*) Accession: Q94AX4.1/GI: 75165032; (*Arabidopsis thaliana*) Accession: AEE84032.1/GI: 332658632; (*Arabidopsis thaliana*) Accession: AEE84031.1/GI: 332658631; (*Arabidopsis thaliana*) Accession: NP_001078406.1/GI: 145333373; (*Arabidopsis thaliana*) Accession: NP_193570.1/GI: 15236857; (*Micromonas* sp. RCC299) Accession: ACO66182.1/GI: 226520193; (*Genlisea aurea*) Accession: EPS70695.1/GI: 527204561; (*Chlamydomonas reinhardtii*) Accession: EDP06163.1/GI: 158280405; (*Micromonas* sp. RCC299) Accession: XP_002504924.1/GI: 255084986; (*Chlamydomonas reinhardtii*) Accession: XP_001703481.1/GI: 159491040; (*Micromonas* sp. RCC299) Accession: ACO61928.1/GI: 226515933; (*Chlamydomonas reinhardtii*) Accession: BAK61668.1/GI: 343403745; (*Micromonas pusilla* CCMP1545) Accession: EEH55456.1/GI: 226458158; (*Micromonas pusilla* CCMP1545) Accession: EEH51246.1/GI: 226453939; (*Micromonas pusilla* CCMP1545) Accession: XP_003064341.1/GI: 303290108; (*Micromonas pusilla* CCMP1545) Accession: XP_003060687.1/GI: 303282791; (*Micromonas* sp. RCC299) Accession: XP_002500670.1/GI: 255073991; (*Coccomyxa subellipsoidea* C-169) Accession: XP_005649475.1/GI: 545369460; (*Spinacia oleracea*) Accession: P05414.1/GI: 121530; (*Oryza sativa* Japonica Group) Accession: Q10CE4.1/GI: 122246745; (*Arabidopsis thaliana*) Accession: Q24JJ8.1/GI: 122195548; (*Arabidopsis thaliana*) Accession: Q9LJH5.1/GI: 75335069; (*Oryza sativa* Japonica Group) Accession: Q8H3I4.2/GI: 75329161; (*Oryza sativa* Japonica Group); Accession: Q7XPR4.3/GI: 317376216; (*Oryza sativa* Indica Group) Accession: B8B8K5.2/GI: 317376202; (*Oryza sativa* Japonica Group) Accession: Q7FAS1.1/GI: 75326731; (*Oryza sativa* Japonica Group) Accession: Q6YT73.1/GI: 75325236; (*Arabidopsis thaliana*) Accession: O49506.1/GI: 75318383; (*Arabidopsis thaliana*) Accession: Q9LRS0.1/GI: 13124263; (*Arabidopsis thaliana*) Accession: Q9LRR9.1/GI: 13124262; (*Arabidopsis thaliana*) Accession: F4I907.1/GI: 449061823; (*Oryza sativa* Indica Group) Accession: Q01KC2.2/GI: 317376213; (*Oryza sativa* Indica Group) Accession: B8AUI3.1/GI: 317376201; (*Oryza sativa* Indica Group) Accession: B8B7C5.1/GI: 317376200; (*Oryza sativa* Indica Group) Accession: B8AKX6.1/GI: 317376187; (*Arabidopsis thaliana*) Accession: AEE75523.1/GI: 332642002; (*Arabidopsis thaliana*) Accession: AEE75522.1/GI: 332642001; (*Arabidopsis thaliana*) Accession: NP_001078155.1/GI: 145332397; (*Arabidopsis thaliana*) Accession: NP_001078154.1/GI: 145332395; (*Arabidopsis thaliana*) Accession: Q9CA90.1/GI: 75308938; (*Arabidopsis thaliana*) Accession: Q9LE33.1/GI: 75311082; (*Arabidopsis thaliana*) Accession: AEE75521.1/GI: 332642000; (*Arabidopsis thaliana*) Accession: AEE75520.1/GI: 332641999; (*Arabidopsis thaliana*) Accession: AEE75519.1/GI: 332641998; (*Arabidopsis thaliana*) Accession: AEE75518.1/GI: 332641997; (*Arabidopsis thaliana*) Accession: AEE75517.1/GI: 332641996.

Glycolate dehydrogenase polypeptide(s) from bacterial origin suitable for the invention include: (*Vibrio ponticus*) Accession: GAK83771.1/GI: 678239733; (*Vibrio ponticus*) Accession: GAK83770.1/GI: 678239732; (*Vibrio ponticus*) Accession: GAK83769.1/GI: 678239731; (*Collimonas arenae*) Accession: AIY39978.1/GI: 725876232; (*Collimonas arenae*) Accession: AIY39977.1/GI: 725876231; (*Collimonas arenae*) Accession: AIY39976.1/GI: 725876230; (*Collimonas arenae*) Accession: AIY39211.1/GI: 725875465; (*Microcystis aeruginosa* NIES-44) Accession: GAL92683.1/GI: 718250409; (*Microcystis aeruginosa* NIES-44) Accession: GAL93127.1/GI: 718250015; (*Microcystis aeruginosa* NIES-44) Accession: GAL93126.1/GI: 718250014; (*Thermus filiformis*) Accession: KGQ21896.1/GI: 702223516; (*Thermus filiformis*) Accession: KGQ21895.1/GI: 702223515; (*Thermus filiformis*) Accession: KGQ20890.1/GI: 702221593; (*Escherichia coli*) Accession: KGI49957.1/GI: 693353475; (*Escherichia coli*) Accession: KGI48634.1/GI: 693352107; (*Escherichia coli*) Accession: KGI48633.1/GI: 693352106; (*Escherichia coli*) Accession: KGI48632.1/GI: 693352105; (*Agrobacterium tumefaciens* LBA4213 (Ach5)) Accession: AHK00528.1/GI: 586948739; (*Agrobacterium tumefaciens* LBA4213 (Ach5)) Accession: AHK00527.1/GI: 586948738; (*Agrobacterium tumefaciens* LBA4213 (Ach5)) Accession: AHK00526.1/GI: 586948737; (*Prochlorococcus* sp. MIT 0703) Accession: KGG35322.1/GI: 691712480; (*Prochlorococcus* sp. MIT 0703) Accession: KGG34948.1/GI: 691712100; (*Prochlorococcus* sp. MIT 0702) Accession: KGG30233.1/GI: 691707154; (*Prochlorococcus* sp. MIT 0702) Accession: KGG29260.1/GI: 691706122; (*Prochlorococcus* sp. MIT 0701) Accession: KGG26677.1/GI: 691703415; (*Prochlorococcus* sp. MIT 0701) Accession: KGG25239.1/GI: 691701913; (*Fimbriimonas ginsengisoli* Gsoil 348) Accession: AIE85110.1/GI: 663072955; (*Enhygromyxa salina*) Accession: KFE73152.1/GI: 670626816; (*Hyalangium minutum*) Accession: KFE66519.1/GI: 670619991; (*Bacillus clausii*) Accession: KFE65667.1/GI: 670619134; (*Bacillus clausii*) Accession: KFE65666.1/GI: 670619133; (*Bacillus clausii*) Accession: KFE65665.1/GI:

670619132; (*Bacillus clausii*) Accession: KFE61464.1/GI: 670614876; (*Streptomyces*) Accession: WP_015578691.1/GI: 505391589; (*Paenibacillus pini* JCM 16418) Accession: GAF08561.1/GI: 585396797; (*Paenibacillus pini* JCM 16418) Accession: GAF08560.1/GI: 585396796; (*Chondromyces apiculatus* DSM 436) Accession: EYF06953.1/GI: 599568966; (*Bacillus wakoensis* JCM 9140) Accession: GAE27103.1/GI: 568807375; (*Bacillus wakoensis* JCM 9140) Accession: GAE27102.1/GI: 568807374; (*Collimonas fungivorans* Ter331) Accession: AEK60573.1/GI: 340551198; (*Pseudomonas aeruginosa* PA1R) Accession: AHA25009.1/GI: 557712983; (*Pseudomonas aeruginosa* PA1R) Accession: AHA25008.1/GI: 557712982; (*Pseudomonas aeruginosa* PA1R) Accession: AHA25007.1/GI: 557712981; (*Pseudomonas aeruginosa* PA1) Accession: AHA19210.1/GI: 557707183; (*Pseudomonas aeruginosa* PA1) Accession: AHA19209.1/GI: 557707182; (*Pseudomonas aeruginosa* PA1) Accession: AHA19208.1/GI: 557707181; (*Ralstonia solanacearum* FQY_4) Accession: AGH85082.1/GI: 469774892; (*Ralstonia solanacearum* FQY_4) Accession: AGH85081.1/GI: 469774891; (*Ralstonia solanacearum* FQY_4) Accession: AGH85080.1/GI: 469774890; (*Bacillus cereus* F837/76) Accession: AEW54435.1/GI: 364511036; (*Streptomyces* sp. PAMC26508) Accession: AGJ57220.1/GI: 478748640; (*Ralstonia solanacearum* FQY_4) Accession: YP_007633582.1/GI: 525970908; (*Ralstonia solanacearum* FQY_4) Accession: YP_007633581.1/GI: 525970907; (*Ralstonia solanacearum* FQY_4) Accession: YP_007633580.1/GI: 525970906; (*Pseudomonas aeruginosa* PA1) Accession: YP_008812253.1/GI: 558675545; (*Pseudomonas aeruginosa* PA1) Accession: YP_008812252.1/GI: 558675544; (*Pseudomonas aeruginosa* PA1) Accession: YP_008812251.1/GI: 558675543; (*Pseudomonas aeruginosa* PA1R) Accession: YP_008805904.1/GI: 558669194; (*Pseudomonas aeruginosa* PA1R) Accession: YP_008805903.1/GI: 558669193; (*Pseudomonas aeruginosa* PA1R) Accession: YP_008805902.1/GI: 558669192; (*Achromobacter xylosoxidans* NH44784-1996) Accession: YP_008027298.1/GI: 528981981; (*Achromobacter xylosoxidans* NH44784-1996) Accession: YP_008027297.1/GI: 528981980; (*Achromobacter xylosoxidans* NH44784-1996) Accession: YP_008027296.1/GI: 528981979; (*Achromobacter xylosoxidans*) Accession: WP_020924479.1/GI: 529016433; (*Achromobacter xylosoxidans*) Accession: WP_020924478.1/GI: 529016432; (*Cystobacter fuscus* DSM 2262) Accession: EPX58458.1/GI: 528053654; (*Achromobacter xylosoxidans* NH44784-1996) Accession: CCH04176.1/GI: 507098589; (*Achromobacter xylosoxidans* NH44784-1996) Accession: CCH04175.1/GI: 507098588; (*Achromobacter xylosoxidans* NH44784-1996) Accession: CCH04174.1/GI: 507098587; (*Ralstonia solanacearum*) Accession: WP_020832615.1/GI: 525966975; (*Bacillus cereus* F837/76) Accession: YP_005117948.1/GI: 376265236; (*Streptomyces* sp. PAMC26508) Accession: YP_007861704.1/GI: 479321653; (*Collimonas fungivorans* Ter331) Accession: YP_004751396.1/GI: 340785931; (*Methylacidiphilum fumariolicum*) Accession: WP_009058940.1/GI: 496349762; (*Methylacidiphilum fumariolicum*) Accession: WP_009058939.1/GI: 496349761; (*Methylacidiphilum infernorum*) Accession: WP_012463234.1/GI: 501439785; (*Methylacidiphilum infernorum*) Accession: WP_012463233.1/GI: 501439784; (*Escherichia coli*) Accession: WP_001703443.1/GI: 487497857; (*Escherichia coli* Nissle 1917) Accession: CCQ05977.1/GI: 441713650; Glycolate dehydrogenasE—*Escherichia coli* Nissle 1917) Accession: CCQ05976.1/GI: 441713649; (*Escherichia coli* Nissle 1917) Accession: CCQ05975.1/GI: 441713648; (*Escherichia coli* O10:K5(L):H4 str. ATCC 23506) Accession: CCP96322.1/GI: 441607314; (*Escherichia coli* O10:K5(L):H4 str. ATCC 23506) Accession: CCP96321.1/GI: 441607313; (*Escherichia coli* O10:K5(L):H4 str. ATCC 23506) Accession: CCP96320.1/GI: 441607312; (*Escherichia coli* O5:K4(L):H4 str. ATCC 23502) Accession: CCQ00751.1/GI: 441654202; (*Escherichia coli* O5:K4(L):H4 str. ATCC 23502) Accession: CCQ00750.1/GI: 441654201; (*Escherichia coli* O5:K4(L):H4 str. ATCC 23502) Accession: CCQ00749.1/GI: 441654200; (Bradyrhizobiaceae bacterium SG-6C) Accession: EGP10038.1/GI: 338234927; (Bradyrhizobiaceae bacterium SG-6C) Accession: EGP10037.1/GI: 338234926; (Bradyrhizobiaceae bacterium SG-6C) Accession: EGP10036.1/GI: 338234925; (Bradyrhizobiaceae bacterium SG-6C) Accession: EGP06191.1/GI: 338231050; (Oxalobacteraceae bacterium IMCC9480) Accession: EGF33327.1/GI: 327548681; (Oxalobacteraceae bacterium IMCC9480) Accession: EGF33326.1/GI: 327548680; (subunit GlcD—*Yersinia ruckeri*) Accession: CEK27678.1/GI: 731155805; (subunit GlcD—*Photobacterium aphoticum*) Accession: GAL06589.1/GI: 684144303; subunit GlcD—*Citrobacter* sp. CIP 55.13) Accession: CEJ67199.1/GI: 729037724; (subunit GlcD—*Pseudomonas* sp. SHC52) Accession: CDF93952.1/GI: 727047302; (subunit GlcE—*Pseudomonas* sp. SHC52) Accession: CDF93951.1/GI: 727047301; (subunit GlcF—*Pseudomonas* sp. SHC52) Accession: CDF93950.1/GI: 727047300; (subunit GlcD—*Sulfitobacter* sp. MM-124) Accession: KHA53862.1/GI: 722017351; (subunit GlcE—*Sulfitobacter* sp. MM-124) Accession: KHA53861.1/GI: 722017350; (subunit GlcF—*Sulfitobacter* sp. MM-124) Accession: KHA53859.1/GI: 722017348; (subunit GlcF—*Bacillus weihenstephanensis*) Accession: AIW86323.1/GI: 719645909; (subunit GlcD—*Vibrio variabilis*) Accession: GAL28777.1/GI: 684619748; (subunit GlcD—*Vibrio variabilis*) Accession: GAL28776.1/GI: 684619747; (subunit GlcD—*Vibrio maritimus*) Accession: GAL21031.1/GI: 684612272; (subunit GlcD—*Vibrio maritimus*) Accession: GAL21030.1/GI: 684612271; (subunit GlcD—*Vibrio maritimus*) Accession: GAL34207.1/GI: 684599410; (subunit GlcD—*Vibrio maritimus*) Accession: GAL34206.1/GI: 684599409; (subunit GlcD—*Bacillus anthracis*) Accession: AIK07381.1/GI: 672925963; (subunit GlcF—*Bacillus anthracis*) Accession: AIK07380.1/GI: 672925962; (subunit GlcE—*Polaromonas* sp. CG9_12) Accession: CDS52647.1/GI: 669784830; GlcF—*Polaromonas* sp. CG9_12) Accession: CDS52645.1/GI: 669784828; (subunit GlcD—*Polaromonas* sp. CG9_12) Accession: CDS52225.1/GI: 669784599; (subunit GlcD—*Jejuia pallidilutea*) Accession: GAL90108.1/GI: 697984292; (subunit GlcD—*Bacillus cereus*) Accession: AIE78640.1/GI: 663078473; (subunit GlcF—*Bacillus cereus*) Accession: AIE78639.1/GI: 663078472; (subunit GlcD—*Algibacter lectus*) Accession: GAL77539.1/GI: 693575543; (subunit GlcD—*Algibacter lectus*) Accession: GAL64672.1/GI: 693566108; (subunit GlcD—*Jejuia pallidilutea*) Accession: GAL70943.1/GI: 693563750; (subunit GlcD—*Jejuia pallidilutea*) Accession: GAL70942.1/GI: 693563749; (subunit GlcD—*Jejuia pallidilutea*) Accession: GAL67396.1/GI: 693559113; (subunit GlcD—*Jejuia pallidilutea*) Accession: GAL67395.1/GI: 693559112; (subunit GlcD—*Lactobacillus plantarum* CMPG5300) Accession: KGH44264.1/GI: 692529015; (subunit GlcD—*Escherichia coli* O145:H28 str. RM12581) Accession: AHY72347.1/GI: 628078821; GlcE—*Escherichia coli* O145:H28 str. RM12581) Accession: AHY72346.1/GI: 628078820; (subunit GlcF—*Escherichia coli* O145:H28 str. RM12581) Accession: AHY72345.1/GI: 628078819; (subunit GlcD—*Escherichia coli* O145:H28 str. RM12761) Accession: AHY66695.1/GI: 628030228; (subunit GlcE—*Escherichia coli* O145:H28 str. RM12761) Accession: AHY66694.1/GI: 628030227; (subunit GlcF—*Escherichia coli* O145:H28 str. RM12761) Accession: AHY66693.1/GI: 628030226; (subunit GlcD—*Gilliamella apicola*) Accession: AHN26357.1/GI: 597811526; (subunit GlcF—*Roseibacterium elongatum* DSM 19469) Accession: AHM04004.1/GI: 594548985; (subunit GlcE—*Roseibacterium elongatum* DSM 19469) Accession: AHM04003.1/GI: 594548984; (subunit GlcD—*Roseibacterium elongatum* DSM 19469) Accession: AHM04002.1/GI: 594548983; (subunit GlcF—*Castellaniella defragrans* 65Phen) Accession: CDM23960.1/GI: 589266024; (subunit GlcE—*Castellaniella defragrans* 65Phen) Accession: CDM23959.1/GI: 589266023; (subunit GlcD—*Castellaniella defragrans* 65Phen) Accession: CDM23958.1/GI: 589266022; (subunit GlcD—*Bacillus subtilis* E1) Accession: CCU59369.1/GI: 659925034; (subunit GlcF—*Methylobacterium oryzae* CBMB20) Accession: AIQ93092.1/GI: 689277013; (subunit GlcD—*Burkholderia glathei*) Accession: CDY76859.1/GI: 678299913; (subunit GlcD—*Burkholderia glathei*) Accession: CDY77463.1/GI: 678299256; (subunit GlcE—*Burkholderia glathei*) Accession: CDY77462.1/GI: 678299255; (subunit GlcF—*Burkholderia glathei*) Accession: CDY77461.1/GI: 678299254; (subunit GlcF—*Paenibacillus* sp. JCM 10914) Accession: GAE09049.1/GI: 560941948; (subunit GlcF—*Paenibacillus* sp. JCM 10914) Accession: GAE09047.1/GI: 560941946; (subunit GlcD—*Paenibacillus* sp. JCM 10914) Accession: GAE09046.1/GI: 560941945; (subunit GlcD—*Paenibacillus* sp. JCM 10914) Accession: GAE09045.1/GI: 560941944; (subunit GlcE—*Synechocystis* sp. PCC 6714) Accession: AIE75713.1/GI: 662705738; (subunit GlcF—*Synechocystis* sp. PCC 6714) Accession: AIE75280.1/GI: 662705305; (subunit GlcD—*Synechocystis* sp. PCC 6714) Accession: AIE74016.1/GI: 662704041; (*Bacillus clausii*) Accession: KFE61465.1/GI: 670614877; (subunit GlcE—*Thioclava* sp. 13D2W-2) Accession: KFE36767.1/GI: 669601292; (subunit GlcD—*Thioclava* sp. 13D2W-2) Accession: KFE36766.1/GI: 669601291; (subunit GlcF—*Escherichia coli* DSM 30083=JCM 1649=ATCC 11775) Accession: KFB96207.1/GI: 668710444; (subunit GlcE—*Escherichia coli* DSM 30083=JCM 1649=ATCC 11775) Accession: KFB96206.1/GI: 668710443; (subunit GlcD—*Escherichia coli* DSM 30083=JCM 1649=ATCC 11775) Accession: KFB96205.1/GI: 668710442; (subunit GlcF—*Brucella suis* bv. 2) Accession: AIB28969.1/GI: 648132977; (subunit GlcE—*Brucella suis* bv. 2) Accession: AIB28968.1/GI: 648132976; (subunit GlcD—*Brucella suis* bv. 2) Accession: AIB28967.1/GI: 648132975; (subunit GlcF—*Brucella suis* bv. 2) Accession: AIB25578.1/GI: 646251316; (subunit GlcE—*Brucella suis* bv. 2) Accession: AIB25577.1/GI: 646251315; (subunit GlcD—*Brucella suis* bv. 2) Accession: AIB25576.1/GI: 646251314; (subunit GlcF—*Brucella suis* bv. 2) Accession: AIB22223.1/GI: 646247957; (subunit GlcE—*Brucella suis* bv. 2) Accession: AIB22222.1/GI: 646247956; (subunit GlcD—*Brucella suis* bv. 2) Accession: AIB22221.1/GI: 646247955; (subunit GlcE—*Geomicrobium* sp. JCM 19037) Accession: GAK04918.1/GI: 636730043; (subunit GlcF—*Geomicrobium* sp. JCM 19037) Accession: GAK04917.1/GI: 636730042; (subunit GlcD—*Geomicrobium* sp. JCM 19037) Accession: GAK04916.1/GI: 636730041; (subunit GlcE—*Geomicrobium* sp. JCM 19039) Accession: GAK13247.1/GI: 636725850; (subunit GlcE—*Geomicrobium* sp. JCM 19039) Accession: GAK13246.1/GI: 636725849; (subunit GlcE—*Geomicrobium* sp. JCM 19039) Accession: GAK13245.1/GI: 636725848; GlcF—*Geomicrobium* sp. JCM 19039) Accession: GAK13244.1/GI: 636725847; (subunit GlcD—*Geomicrobium* sp. JCM 19039) Accession: GAK13243.1/GI: 636725846; (subunit GlcD—*Bacillus thuringiensis* serovar kurstaki str. HD-1) Accession: KEH48238.1/GI: 657515466; (subunit GlcF—*Bacillus thuringiensis* serovar kurstaki str. HD-1) Accession: KEH48237.1/GI: 657515465; (subunit GlcD—*Marinobacter* sp. AK21) Accession: KEF30543.1/GI: 656104851; (subunit GlcE—*Marinobacter* sp. AK21) Accession: KEF30542.1/GI: 656104850; (subunit GlcF—*Marinobacter* sp. AK21) Accession: KEF30541.1/GI: 656104849; (subunit GlcF—*Burkholderia cepacia* complex) Accession: WP_021163859.1/GI: 544734260; (subunit GlcF—*Sinorhizobium americanum* CCGM7) Accession: KEC71436.1/GI: 654362296; (subunit GlcD—*Marinobacterium* sp. AK27) Accession: KEA65018.1/GI: 653658306; (subunit GlcE—*Marinobacterium* sp. AK27) Accession: KEA65017.1/GI: 653658305; (subunit GlcF—*Marinobacterium* sp. AK27) Accession: KEA65016.1/GI: 653658304; (subunit GlcD—*Marinobacterium* sp. AK27) Accession: KEA61950.1/GI: 653654869; (subunit GlcD—*Marinobacterium* sp. AK27) Accession: KEA61904.1/GI: 653654823; (subunit GlcF—*Brucella suis* bv. 2) Accession: AIB32340.1/GI: 646254683; (subunit GlcE—*Brucella suis* bv. 2) Accession: AIB32339.1/GI: 646254682; (subunit GlcD—*Brucella suis* bv. 2) Accession: AIB32338.1/GI: 646254681; (subunit GlcF—*Brucella suis* bv. 2) Accession: AIB18839.1/GI: 646244569; (subunit GlcE—*Brucella suis* bv. 2) Accession: AIB18838.1/GI: 646244568; subunit GlcD—*Brucella suis* bv. 2) Accession: AIB18837.1/GI: 646244567; (subunit GlcF—*Richelia intracellularis*) Accession: CDN13559.1/GI: 605043415; (subunit GlcE—*Richelia intracellularis*) Accession: CDN13558.1/GI: 605043414; (subunit GlcD—*Richelia intracellularis*) Accession: CDN17153.1/GI: 605039408; (subunit GlcD—*Acidithiobacillus caldus* ATCC 51756) Accession: AIA56107.1/GI: 640842222; (subunit GlcE—*Acidithiobacillus caldus* ATCC 51756) Accession: AIA56106.1/GI: 640842221; (subunit GlcF—*Acidithiobacillus caldus* ATCC 51756) Accession: AIA56105.1/GI: 640842220; (subunit GlcF—*Escherichia coli*) Accession: KDN06031.1/GI: 636872977; (subunit GlcE—*Escherichia coli*) Accession: KDN06030.1/GI: 636872976; (subunit GlcD—*Escherichia coli*) Accession: KDN06029.1/GI: 636872975; (subunit GlcE—*Burkholderia* sp. AU4i) Accession: WP_021163858.1/GI: 544734259; (subunit GlcD—*Burkholderia* sp. AU4i) Accession: WP_021163857.1/GI: 544734258; (subunit GlcF—*Burkholderia* sp. AU4i) Accession: WP_021163546.1/GI: 544733909; (subunit GlcD—*Burkholderia* sp. AU4i) Accession: WP_021163545.1/GI: 544733908; (subunit GlcF—*Burkholderia* sp. AU4i) Accession: WP_021161413.1/GI: 544731662; (subunit GlcD—*Lactobacillus plantarum* WCFS1) Accession: YP_004888330.1/GI: 380031339; (subunit GlcD—*Nitrincola lacisaponensis*) Accession: KDE40915.1/GI: 635199988; (subunit GleE—*Nitrincola lacisaponensis*) Accession: KDE40914.1/GI: 635199987; (subunit GlcF—*Nitrincola lacisaponensis*) Accession: KDE40913.1/GI: 635199986; (subunit GlcD—*Nitrincola lacisaponensis*) Accession: KDE40017.1/GI: 635199084; (subunit GlcD—*Lactobacillus casei* 12A) Accession: EKP96625.1/GI: 410521667; (subunit GlcD—*Burkholderia cenocepacia* H111) Accession: CDN64533.1/GI: 590120476; (subunit GlcD—*Lactobacillus farraginis* DSM 18382=JCM 14108)

Accession: GAF36870.1/GI: 588485933; (subunit GlcD—*Lactobacillus composti* DSM 18527=JCM 14202) Accession: GAF40649.1/GI: 588475006; (subunit GlcD—*Lactobacillus composti* DSM 18527=JCM 14202) Accession: GAF40969.1/GI: 588474669; (subunit GlcD—*Lactobacillus composti* DSM 18527=JCM 14202) Accession: GAF41605.1/GI: 588473973; (subunit GlcF—*Lactobacillus composti* DSM 18527=JCM 14202) Accession: GAF41604.1/GI: 588473972; (subunit GlcD—*Burkholderia cenocepacia* H111) Accession: CDN59109.1/GI: 590115052; (subunit GlcE—*Burkholderia cenocepacia* H111) Accession: CDN59108.1/GI: 590115051; (subunit GlcF—*Burkholderia cenocepacia* H111) Accession: CDN59107.1/GI: 590115050; (subunit GlcD—*Burkholderia caribensis* MBA4) Accession: EZP25123.1/GI: 612063862; (subunit GlcF—*Burkholderia caribensis* MBA4) Accession: ETY84259.1/GI: 575865073; (subunit GlcE—*Burkholderia caribensis* MBA4) Accession: ETY84258.1/GI: 575865072; (subunit GlcE—*Burkholderia caribensis* MBA4) Accession: ETY80272.1/GI: 575861062; (subunit GlcF—*Burkholderia caribensis* MBA4) Accession: ETY80271.1/GI: 575861061; (subunit GlcD—*Burkholderia caribensis* MBA4) Accession: ETY79681.1/GI: 575860465; (subunit GlcE—*Burkholderia caribensis* MBA4) Accession: ETY79680.1/GI: 575860464; (subunit GlcD—*Nodularia spumigena* CCY9414) Accession: AHJ31191.1/GI: 585124249; (subunit GlcE—*Nodularia spumigena* CCY9414) Accession: AHJ28233.1/GI: 585121291; (subunit GlcF—*Nodularia spumigena* CCY9414) Accession: AHJ28231.1/GI: 585121289; (subunit GlcF—*Pseudomonas aeruginosa* PA103) Accession: EYU08360.1/GI: 602747861; (subunit GlcD—*Pseudomonas aeruginosa* PA99) Accession: EYU03926.1/GI: 602743266; (subunit GlcE—*Pseudomonas aeruginosa* PA99) Accession: EYU03925.1/GI: 602743265; (subunit GlcF—*Pseudomonas aeruginosa* PA99) Accession: EYU03888.1/GI: 602743226; (subunit GlcE—*Pseudomonas aeruginosa* PA103) Accession: EYU00813.1/GI: 602740013; (subunit GlcD—*Pseudomonas aeruginosa* PA103) Accession: EYU00812.1/GI: 602740012; (subunit GlcD—*Rubellimicrobium mesophilum* DSM 19309) Accession: EYD77315.1/GI: 598664788; (subunit GleE—*Rubellimicrobium mesophilum* DSM 19309) Accession: EYD77314.1/GI: 598664787; (subunit GlcF—*Rubellimicrobium mesophilum* DSM 19309) Accession: EYD77313.1/GI: 598664786; (subunit GlcD—*Loktanella hongkongensis* DSM 17492) Accession: EYD70622.1/GI: 598657251; (subunit GlcE—*Loktanella hongkongensis* DSM 17492) Accession: EYD70621.1/GI: 598657250; (subunit GlcF—*Loktanella hongkongensis* DSM 17492) Accession: EYD70620.1/GI: 598657249; (subunit GlcD—*Bacillus anthracis* CZC5) Accession: GAE96759.1/GI: 576742197; (subunit GlcF—*Bacillus anthracis* CZC5) Accession: GAE96758.1/GI: 576742196; (subunit GlcD—*Escherichia coli* O145:H28 str. RM13514) Accession: AHG10530.1/GI: 573970265; (subunit GlcE—*Escherichia coli* O145:H28 str. RM13514) Accession: AHG10529.1/GI: 573970264; (subunit GlcF—*Escherichia coli* O145:H28 str. RM13514) Accession: AHG10528.1/GI: 573970263; (subunit GlcD—*Escherichia coli* O145:H28 str. RM13516) Accession: AHG16372.1/GI: 573936567; (subunit GlcE—*Escherichia coli* O145:H28 str. RM13516) AHG16371.1/GI: 573936566; (subunit GlcF—*Escherichia coli* O145:H28 str. RM13516) Accession: AHG16370.1/GI: 573936565; (subunit GlcD—*Lactobacillus rhamnosus* LOCK908) Accession: AGP75006.1/GI: 521380148; (subunit GlcD—*Alkalibacterium* sp. AK22) Accession: EXJ24332.1/GI: 589844094; (subunit GlcF—*Thiorhodococcus* sp. AK35) Accession: EXJ15514.1/GI: 589833154; (subunit GlcE—*Thiorhodococcus* sp. AK35) Accession: EXJ15513.1/GI: 589833153; (subunit GlcD—*Thiorhodococcus* sp. AK35) Accession: EXJ14044.1/GI: 589831660; (subunit GlcD—*Pseudomonas aeruginosa* SCV20265) Accession: AHC80185.1/GI: 567369240; (subunit GlcE—*Pseudomonas aeruginosa* SCV20265) Accession: AHC80184.1/GI: 567369239; (subunit GlcF—*Pseudomonas aeruginosa* SCV20265) Accession: AHC80183.1/GI: 567369238; (subunit GlcD—*Clostridium tyrobutyricum* DIVETGP) Accession: CDL90464.1/GI: 587651050; (subunit GlcD—*Clostridium tyrobutyricum* DIVETGP) Accession: CDL92712.1/GI: 587648629; (subunit GlcE—*Escherichia albertii* KF1) Accession: AHE60838.1/GI: 569538531; (subunit GlcD—*Escherichia coli* NA114) Accession: AEG37894.1/GI: 333971089; (subunit GlcF—*Achromobacter xylosoxidans* NBRC 15126=ATCC 27061) Accession: AHC46259.1/GI: 566050586; (subunit GlcE—*Achromobacter xylosoxidans* NBRC 15126=ATCC 27061) Accession: AHC46258.1/GI: 566050585; (subunit GlcD—*Achromobacter xylosoxidans* NBRC 15126=ATCC 27061) Accession: AHC46257.1/GI: 566050584; (*Bacillus thuringiensis* YBT-1518) Accession: AHA70700.1/GI: 558578565; (subunit GlcF—*Bacillus thuringiensis* YBT-1518) Accession: AHA70699.1/GI: 558578564; (subunit GlcD—*Actinokineospora* sp. EG49) Accession: EWC64120.1/GI: 583004694; (subunit GlcD—*Actinokineospora* sp. EG49]; Accession: EWC63240.1/GI: 583003784; (subunit GlcD—*Actinokineospora* sp. EG49) Accession: EWC61535.1/GI: 583002023; (subunit GlcD—*Actinokineospora* sp. EG49) Accession: EWC58823.1/GI: 582998387; (subunit GlcD—*Actinokineospora* sp. EG49) Accession: EWC58610.1/GI: 582998155; (subunit GlcD—*Lactobacillus plantarum* 16) Accession: AGO06960.1/GI: 513034564; (*Bacillus thuringiensis* serovar *thuringiensis* str. IS5056) Accession: AGF99954.1/GI: 452103015; (subunit GlcF—*Bacillus thuringiensis* serovar *thuringiensis* str. IS5056) Accession: AGF99953.1/GI: 452103014; (subunit GlcD—*Lactobacillus plantarum* ZJ316) Accession: AGE38026.1/GI: 448273507; (subunit GlcD—*Burkholderia cepacia* GG4) Accession: AFQ51978.1/GI: 402251525; (subunit GlcD—*Burkholderia* sp. KJ006) Accession: AFJ85008.1/GI: 387576292; (subunit GlcE—*Burkholderia* sp. KJ006) Accession: AFJ85007.1/GI: 387576291; (subunit GlcD—*Collimonas fungivorans* Ter331) Accession: AEK60575.1/GI: 340551200; (subunit GlcE—*Collimonas fungivorans* Ter331) Accession: AEK60574.1/GI: 340551199; (subunit GlcD—*Rhodobacter capsulatus* SB 1003) Accession: ADE86600.1/GI: 294477212; (subunit GlcE—*Rhodobacter capsulatus* SB 1003) Accession: ADE86599.1/GI: 294477211; (subunit GlcF—*Rhodobacter capsulatus* SB 1003) Accession: ADE86598.1/GI: 294477210; (subunit GlcF—*Methylacidiphilum infernorum* V4) Accession: ACD83652.1/GI: 189186467; (subunit GlcD—*Methylacidiphilum infernorum* V4) Accession: ACD83650.1/GI: 189186465; (subunit GlcF—*Methylacidiphilum infernorum* V4) Accession: ACD82952.1/GI: 189185767; (subunit GlcE—*Methylacidiphilum infernorum* V4) Accession: ACD82951.1/GI: 189185766; (subunit GlcD—*Lactobacillus rhamnosus* LOCK900) Accession: AGP72079.1/GI: 521376527; (subunit GlcD—*Lactobacillus casei* LOCK919) Accession: AGP69226.1/GI: 521372145; (subunit GlcF—*Thioalkalivibrio nitratireducens* DSM 14787) Accession: AGA33895.1/GI: 430011143; (subunit GlcE—*Thioalkalivibrio nitratireducens* DSM 14787) Accession: AGA33894.1/GI:

430011142; (subunit GlcD—*Thioalkalivibrio nitratireducens* DSM 14787) Accession: AGA33893.1/GI: 430011141; (subunit GlcD—*Acidithiobacillus caldus* SM-1) Accession: AEK59062.1/GI: 340557308; (subunit GlcE—*Acidithiobacillus caldus* SM-1) Accession: AEK59061.1/GI: 340557307; (subunit GlcF—*Acidithiobacillus caldus* SM-1) Accession: AEK59060.1/GI: 340557306; (subunit GlcF—*Candidatus Pelagibacter* sp. IMCC9063) Accession: AEA80927.1/GI: 327486522; (subunit GlcE—*Candidatus Pelagibacter* sp. IMCC9063) Accession: AEA80926.1/GI: 327486521; (subunit GlcD—*Candidatus Pelagibacter* sp. IMCC9063) Accession: AEA80925.1/GI: 327486520; (subunit GlcF—*Escherichia coli* ISC41) Accession: CDL45957.1/GI: 576029023; (subunit GlcD—*Escherichia coli* ISC41) Accession: CDL48739.1/GI: 576026958; (subunit GlcD—*Escherichia coli* IS29) Accession: CDK89963.1/GI: –572154655; (subunit GlcE—*Escherichia coli* IS29) Accession: CDK89962.1/GI: 572154654; (subunit GlcF—*Escherichia coli* IS29) Accession: CDK89961.1/GI: 572154653; (subunit GlcD—*Escherichia coli* IS35) Accession: CDL03303.1/GI: 571239987; (subunit GlcE—*Escherichia coli* IS35) Accession: CDL03302.1/GI: 571239986; (subunit GlcF—*Escherichia coli* IS35) Accession: CDL03301.1/GI: 571239985; (subunit GlcD—*Escherichia coli* IS9) Accession: CDK59008.1/GI: 571218906; (subunit GlcF—*Escherichia coli* IS9) Accession: CDK59453.1/GI: 571218606; (subunit GlcE—*Escherichia coli* IS9) Accession: CDK59452.1/GI: 571218605; (subunit GlcF—*Klebsiella pneumoniae* IS22) Accession: CDK76008.1/GI: 571209818; (subunit GlcF—*Klebsiella pneumoniae* IS22) Accession: CDK76007.1/GI: 571209817; (subunit GlcE—*Klebsiella pneumoniae* IS22) Accession: CDK76006.1/GI: 571209816; (subunit GlcD—*Klebsiella pneumoniae* IS22) Accession: CDK76005.1/GI: 571209815; (subunit GlcD—*Escherichia coli* ISC7) Accession: CDL25131.1/GI: 571185631; (subunit GlcE—*Escherichia coli* ISC7) Accession: CDL27302.1/GI: 571183498; (subunit GlcF—*Escherichia coli* ISC7) Accession: CDL27301.1/GI: 571183497; (subunit GlcF—*Escherichia coli* ISC7) Accession: CDL27300.1/GI: 571183496; (subunit GlcF—*Escherichia coli* ISC7) Accession: CDL27299.1/GI: 571183495; (subunit GlcD—*Escherichia coli* IS25) Accession: CDK81232.1/GI: 571178845; (subunit GlcE—*Escherichia coli* IS25) Accession: CDK81231.1/GI: 571178844; (subunit GlcF—*Escherichia coli* IS25) Accession: CDK81230.1/GI: 571178843; (subunit GlcD—*Bacillus toyonensis* BCT-7112) Accession: AHA09808.1/GI: 557475986; (subunit GlcF—*Bacillus toyonensis* BCT-7112) Accession: AHA09807.1/GI: 557475985; (subunit GlcF—*Escherichia coli* IS5) Accession: CDK49908.1/GI: 568396699; (subunit GlcE—*Escherichia coli* IS5) Accession: CDK49907.1/GI: 568396698; (subunit GlcD—*Escherichia coli* IS5) Accession: CDK51787.1/GI: 568394700; (subunit GlcF—*Escherichia coli* IS1) Accession: CDK49045.1/GI: 568385473; (subunit GlcE—*Escherichia coli* IS1) Accession: CDK49044.1/GI: 568385472; (subunit GlcD—*Escherichia coli* IS1) Accession: CDK49093.1/GI: 568385414; (subunit GlcD—*Pseudomonas aeruginosa* SCV20265) Accession: YP_008985079.1/GI: 568312810; (subunit GlcE—*Pseudomonas aeruginosa* SCV20265) Accession: YP_008985078.1/GI: 568312809; (subunit GlcF—*Pseudomonas aeruginosa* SCV20265) Accession: YP_008985077.1/GI: 568312808; (subunit GlcF—*Achromobacter xylosoxidans*) Accession: WP_024068248.1/GI: 568193884; (subunit GlcE—*Achromobacter xylosoxidans*) Accession: WP_024068247.1/GI: 568193883; (subunit GlcD—*Achromobacter xylosoxidans*) Accession: WP_024068246.1/GI: 568193882; (subunit GlcF—*Achromobacter xylosoxidans* NBRC 15126=ATCC 27061) Accession: YP_008923560.1/GI: 568126913; (subunit GlcE—*Achromobacter xylosoxidans* NBRC 15126=ATCC 27061) Accession: YP_008923559.1/GI: 568126912; (subunit GlcD—*Achromobacter xylosoxidans* NBRC 15126=ATCC 27061) Accession: YP_008923558.1/GI: 568126911; (subunit GlcF—*Escherichia coli* AA86) Accession: EGH37547.1/GI: 330909033; (subunit GlcF—*Paenibacillus* sp. JCM 10914) Accession: WP_023965351.1/GI: 565884101; (subunit GlcF—*Paenibacillus* sp. JCM 10914) Accession: WP_023965347.1/GI: 565884097; (subunit GlcD—*Paenibacillus* sp. JCM 10914) Accession: WP_023965344.1/GI: 565884094; (subunit GlcD—*Paenibacillus* sp. JCM 10914) Accession: WP_023965343.1/GI: 565884093; (subunit GlcF—*Escherichia coli* E1777) Accession: ESV01283.1/GI: 559784071; (subunit GlcE—*Escherichia coli* E1777) Accession: ESV01282.1/GI: 559784070; (subunit GlcD—*Escherichia coli* E1777) Accession: ESV01281.1/GI: 559784069; (subunit glcF—*Loktanella cinnabarina* LL-001) Accession: GAD55046.1/GI: 543422469; (subunit glcE—*Loktanella cinnabarina* LL-001) Accession: GAD55045.1/GI: 543422468; (subunit glcD—*Loktanella cinnabarina* LL-001) Accession: GAD55044.1/GI: 543422467; (*Bacillus thuringiensis* YBT-1518) Accession: YP_008817887.1/GI: 558679758; (subunit GlcF—*Bacillus thuringiensis* YBT-1518) Accession: YP_008817886.1/GI: 558679757; (subunit GlcD—*Burkholderia cenocepacia*) Accession: WP_023477001.1/GI: 558016316; (subunit GlcE—*Burkholderia cenocepacia*) Accession: WP_023477000.1/GI: 558016313; (subunit GlcD—*Escherichia coli* CE516) Accession: ESS91591.1/GI: 557927411; (subunit GlcE—*Escherichia coli* CE516) Accession: ESS91590.1/GI: 557927410; (subunit GlcF—*Escherichia coli* CE516) Accession: ESS91589.1/GI: 557927409; (subunit GlcF—*Escherichia coli* CE549) Accession: ESS91299.1/GI: 557927049; (subunit GlcE—*Escherichia coli* CE549) Accession: ESS91298.1/GI: 557927048; (subunit GlcD—*Escherichia coli* CE549) Accession: ESS91297.1/GI: 557927047; (subunit GlcD—*Burkholderia cenocepacia* KC-01) Accession: ESS38209.1/GI: 557794185; (subunit GlcE—*Burkholderia cenocepacia* KC-01) Accession: ESS38208.1/GI: 557794184; (subunit GlcF—*Lutibaculum baratangense*) Accession: WP_023431022.1/GI: 557676479; (subunit GlcE—*Lutibaculum baratangense*) Accession: WP_023431021.1/GI: 557676475; (subunit GlcD—*Lutibaculum baratangense*) Accession: WP_023431020.1/GI: 557676472; (subunit GlcD—*Bacillus toyonensis* BCT-7112) Accession: YP_008784498.1/GI: 557623366; (subunit GlcF—*Bacillus toyonensis* BCT-7112) Accession: YP_008784497.1/GI: 557623365; (subunit GlcF—*Lutibaculum baratangense* AMV1) Accession: ESR26376.1/GI: 557406299; (subunit GlcE—*Lutibaculum baratangense* AMV1) Accession: ESR26375.1/GI: 557406298; (subunit GlcD—*Lutibaculum baratangense* AMV1) Accession: ESR26374.1/GI: 557406297; (subunit GlcF—*Escherichia coli* SCD1) Accession: ESA31008.1/GI: 553024184; (subunit GlcE—*Escherichia coli* SCD1) Accession: ESA31007.1/GI: 553024183; (subunit GlcD—*Escherichia coli* SCD1) Accession: ESA31006.1/GI: 553024182; (subunit GlcF—*Escherichia coli* SCD2) Accession: ESA29685.1/GI: 553022841; (subunit GlcE—*Escherichia coli* SCD2) Accession: ESA29684.1/GI: 553022840; (subunit GlcD—*Escherichia coli* SCD2) Accession: ESA29683.1/GI: 553022839; (subunit GlcF—*Crocosphaera watsonii* WH 0401) Accession:

CCQ63359.1/GI: 543428392; (subunit GlcE—*Crocosphaera watsonii* WH 0401) Accession: CCQ63358.1/GI: 543428391; (subunit GlcD—*Crocosphaera watsonii* WH 0401) Accession: CCQ64344.1/GI: 543427231; (subunit GlcD—*Bacillus* sp. GeD10) Accession: CCW04120.1/GI: 482659080; (subunit GlcF—*Bacillus* sp. GeD10) Accession: CCW04119.1/GI: 482659079; (subunit GlcE—*Crocosphaera watsonii*) Accession: WP_021836465.1/GI: 546233603; (subunit GlcE—*Crocosphaera watsonii*) Accession: WP_021832550.1/GI: 546225655; (subunit GlcE—*Crocosphaera watsonii*) Accession: WP_021830164.1/GI: 546209745; (subunit GlcF—*Crocosphaera watsonii*) Accession: WP_021830163.1/GI: 546209744; (subunit GlcD—*Crocosphaera watsonii*) Accession: WP_021829695.1/GI: 546207139; (subunit glcF—*Loktanella cinnabarina*) Accession: WP_021693154.1/GI: 545456215; (subunit glcE—*Loktanella cinnabarina*) Accession: WP_021693153.1/GI: 545456214; (subunit glcD—*Loktanella cinnabarina*) Accession: WP_021693152.1/GI: 545456213; (subunit GlcD—*Thalassobacter arenae*) Accession: WP_021101159.1/GI: 544667804; (subunit GlcE—*Thalassobacter arenae*) Accession: WP_021101158.1/GI: 544667803; (subunit GlcF—*Thalassobacter arenae*) Accession: WP_021101157.1/GI: 544667802; (*Myxococcus* sp.) Accession: ERK85659.1/GI: 544268043; (subunit GlcD—*Crocosphaera watsonii* WH 0402) Accession: CCQ68714.1/GI: 543534437; (subunit GlcF—*Crocosphaera watsonii* WH 0402) Accession: CCQ69206.1/GI: 543533753; (subunit GlcE—*Crocosphaera watsonii* WH 0402) Accession: CCQ69205.1/GI: 543533752; (subunit GlcF—*Crocosphaera watsonii* WH 0005) Accession: CCQ54800.1/GI: 543527779; (subunit GlcE—*Crocosphaera watsonii* WH 0005) Accession: CCQ54799.1/GI: 543527778; (subunit GlcD—*Crocosphaera watsonii* WH 0005) Accession: CCQ57454.1/GI: 543523890; (subunit GlcD—*Crocosphaera watsonii* WH 8502) Accession: CCQ49822.1/GI: 543517710; (subunit GlcE—*Crocosphaera watsonii* WH 8502) Accession: CCQ50520.1/GI: 543516532; (subunit GlcF—*Crocosphaera watsonii* WH 8502) Accession: CCQ50519.1/GI: 543516531; (subunit GlcF—*Burkholderia* sp. AU4i) Accession: ERJ36103.1/GI: 543288458; (subunit GlcE—*Burkholderia* sp. AU4i) Accession: ERJ33770.1/GI: 543285528; (subunit GlcD—*Burkholderia* sp. AU4i) Accession: ERJ33769.1/GI: 543285527; (subunit GlcF—*Burkholderia* sp. AU4i) Accession: ERJ33412.1/GI: 543284995; (subunit GlcE—*Burkholderia* sp. AU4i) Accession: ERJ33411.1/GI: 543284994; (subunit GlcD—*Burkholderia* sp. AU4i) Accession: ERJ33410.1/GI: 543284993; (subunit GlcF—*Bacillus*) Accession: WP_006917711.1/GI: 493974627; (subunit GlcD—*Lactobacillus casei* group) Accession: WP_003607194.1/GI: 489703057; (subunit GlcD—*Lactobacillus casei* group) Accession: WP_003603233.1/GI: 489699094; (subunit GlcD family (*Lactobacillus casei* group) Accession: WP_003580769.1/GI: 489676531; (subunit GlcD—*Acidithiobacillus caldus* SM-1) Accession: YP_004749764.1/GI: 340783157; (subunit GlcE—*Acidithiobacillus caldus* SM-1) Accession: YP_004749763.1/GI: 340783156; (subunit GlcF—*Acidithiobacillus caldus* SM-1) Accession: YP_004749762.1/GI: 340783155; (subunit GlcF—*Nitrosospira* sp. APG3) Accession: CCU61652.1/GI: 475054192; (subunit GlcE—*Nitrosospira* sp. APG3) Accession: CCU61651.1/GI: 475054191; (subunit GlcD—*Nitrosospira* sp. APG3) Accession: CCU61650.1/GI: 475054190; (subunit GlcF—*Nitrosospira* sp. APG3) Accession: CCU62734.1/GI: 475052935; (subunit GlcF—*Salipiger mucosus* DSM 16094) Accession: EPX83070.1/GI: 528101421; (subunit GlcD—*Thalassobacter arenae* DSM 19593) Accession: EPX81660.1/GI: 528099957; (subunit GlcE—*Thalassobacter arenae* DSM 19593) Accession: EPX81659.1/GI: 528099956; (subunit GlcF—*Thalassobacter arenae* DSM 19593) Accession: EPX81658.1/GI: 528099955; (subunit GlcD—*Burkholderia cepacia* GG4) Accession: YP_006619672.1/GI: 402570328; (subunit GlcD—*Lactobacillus plantarum* 16) Accession: YP_008120101.1; GI: 513840129; (subunit GlcD—*Lactobacillus rhamnosus* LOCK908) Accession: YP_008206863.1/GI: 523520783; (subunit GlcD—*Lactobacillus rhamnosus* LOCK900) Accession: YP_008203896.1/GI: 523517814; (subunit GlcD—*Lactobacillus casei* LOCK919) Accession: YP_008201043.1/GI: 523514959; (subunit GlcF—*Candidatus Pelagibacter* sp. IMCC9063) Accession: YP_004357666.1/GI: 330813427; (subunit GlcE—*Candidatus Pelagibacter* sp. IMCC9063) Accession: YP_004357665.1/GI: 330813426; (subunit GlcD—*Candidatus Pelagibacter* sp. IMCC9063) Accession: YP_004357664.1/GI: 330813425; (subunit GlcD—*Rhodococcus* sp. EsD8) Accession: CCW15042.1/GI: 482629058; (subunit GlcD—*Halanaerobium saccharolyticum* subsp. *saccharolyticum* DSM 6643) Accession: CCU78735.1/GI: 460789796; (subunit GlcD—*Halanaerobium saccharolyticum* subsp. *saccharolyticum* DSM 6643) Accession: CCU78906.1/GI: 460788890; (subunit GlcD—*Escherichia coli* E2265) Accession: EPH48303.1/GI: 514335898; (subunit GlcE—*Escherichia coli* E2265) Accession: EPH48302.1/GI: 514335897; (subunit GlcF—*Escherichia coli* E2265) Accession: EPH48301.1/GI: 514335896; (subunit GlcD—*Lactobacillus plantarum*) Accession: WP_016526882.1/GI: 513881376; (subunit GlcD—*Lactobacillus plantarum*) Accession: WP_016511414.1/GI: 513804516; (subunit GlcD—*Lactobacillus plantarum* IPLA88) Accession: EPD24615.1/GI: 511781180; (subunit GlcD—*Lactobacillus paracasei*) Accession: WP_016388090.1/GI: 511754494; (subunit GlcD—*Lactobacillus paracasei*) Accession: WP_016385692.1/GI: 511751024; (subunit GlcD—*Lactobacillus paracasei*) Accession: WP_016384795.1/GI: 511749995; (subunit GlcD—*Burkholderia* sp. KJ006) Accession: YP_006331739.1/GI: 387901400; (subunit GlcE—*Burkholderia* sp. KJ006) Accession: YP_006331738.1/GI: 387901399; (subunit GlcD—*Lactobacillus paracasei* subsp. *paracasei* Lpp225) Accession: EPC38404.1/GI: 511400394; (subunit GlcD—*Lactobacillus paracasei* subsp. *paracasei* Lpp120) Accession: EPC34604.1/GI: 511396438; (subunit GlcD—*Lactobacillus paracasei* subsp. *paracasei* Lpp22) Accession: EPC33420.1/GI: 511395164; (subunit GlcD—*Lactobacillus paracasei* subsp. *paracasei* Lpp223) Accession: EPC32806.1/GI: 511394511; (subunit GlcD—*Lactobacillus paracasei* subsp. *paracasei* Lpp46) Accession: EPC26602.1/GI: 511387879; (subunit GlcD—*Lactobacillus paracasei* subsp. *paracasei* Lpp17) Accession: EPC22692.1/GI: 511383770; (subunit GlcD—*Lactobacillus paracasei* subsp. *paracasei* Lpp226) Accession: EPC21198.1/GI: 511382182; (subunit GlcD—*Lactobacillus paracasei* subsp. *paracasei* Lpp122) Accession: EPC19465.1/GI: 511380408; (subunit GlcD—*Lactobacillus paracasei* subsp. *tolerans* Lp17) Accession: EPC15010.1/GI: 511375735; (subunit GlcD—*Lactobacillus paracasei* subsp. *paracasei* Lpp230) Accession: EPC12340.1/GI: 511372931; (*Bacillus thuringiensis* serovar *thuringiensis* str. IS5056) Accession: YP_007477703.1/GI: 452197622; (subunit GlcF—*Bacillus thuringiensis* serovar *thuringiensis* str. IS5056) Accession: YP_007477702.1/GI: 452197621; (subunit GlcD—*Lactobacillus plantarum* ZJ316) Accession: YP_007413172.1/GI: 448820010; (subunit GlcF—*Thioalkalivibrio nitratireducens* DSM 14787) Accession: YP_007217376.1/GI: 430761519; (subunit GlcE—*Thioalkalivibrio nitratireducens* DSM 14787) Accession: YP_007217375.1/GI: 430761518; (subunit GlcD—*Thioalkalivibrio nitratireducens* DSM 14787) Accession: YP_007217374.1/GI: 430761517; (subunit GlcD—*Escherichia coli* NA114) Accession: YP_006140168.1/GI: 386620588; (subunit GlcD—*Rhodobacter capsulatus* SB 1003) Accession: YP_003579007.1/GI: 294678392; (subunit GlcE—*Rhodobacter capsulatus* SB 1003) Accession: YP_003579006.1/GI: 294678391; (subunit GlcF—*Rhodobacter capsulatus* SB 1003) Accession: YP_003579005.1/GI: 294678390; (subunit GlcF—*Methylacidiphilum infernorum* V4) Accession: YP_001940250.1/GI: 189219609; (subunit GlcD—*Methylacidiphilum infernorum* V4) Accession: YP_001940248.1/GI: 189219607; (subunit GlcF—*Methylacidiphilum infernorum* V4) Accession: YP_001939550.1/GI: 189218909; (subunit GlcE—*Methylacidiphilum infernorum* V4) Accession: YP_001939549.1/GI: 189218908; (subunit GlcD—*Rhodobacter* sp. AKP1) Accession: WP_009563066.1/GI: 497248849; (subunit GlcE—*Rhodobacter* sp. AKP1) Accession: WP_009563065.1/GI: 497248848; (subunit GlcF—*Rhodobacter* sp. AKP1) Accession: WP_009563064.1/GI: 497248847; (subunit GlcF—*Caenispirillum salinarum*) Accession: WP_009542738.1/GI: 497228476; (subunit GlcE—*Caenispirillum salinarum*) Accession: WP_009542737.1/GI: 497228475; (subunit GlcD—*Caenispirillum salinarum*) Accession: WP_009542736.1/GI: 497228474; (subunit GlcE—*Crocosphaera watsonii*) Accession: WP_007309487.1/GI: 494520033; (subunit GlcE—*Herbaspirillum frisingense*) Accession: WP_006464790.1/GI: 493510439; (subunit GlcD—*Clostridiaceae bacterium* L21-TH-D2) Accession: WP_006311157.1/GI: 493354535; (subunit GlcD—*Lactobacillus rhamnosus*) Accession: WP_005716550.1/GI: 492011914; (subunit GlcD—*Halanaerobium saccharolyticum*) Accession: WP_005488303.1/GI: 491630764; (subunit GlcD—*Halanaerobium saccharolyticum*) Accession: WP_005488139.1/GI: 491630600; (subunit GlcD—*Amycolatopsis azurea*) Accession: WP_005160695.1/GI: 491302692; (subunit GlcD—*Amycolatopsis azurea*) Accession: WP_005150580.1/GI: 491292564; (subunit GlcD—*Lactobacillus plantarum*) Accession: WP_015379716.1/GI: 505192614; (subunit GlcF—*Thioalkalivibrio nitratireducens*) Accession: WP_015259016.1/GI: 505071914; (subunit GlcE—*Thioalkalivibrio nitratireducens*) Accession: WP_015259015.1/GI: 505071913; (subunit GlcD—*Thioalkalivibrio nitratireducens*) Accession: WP_015259014.1/GI: 505071912; (subunit GlcD (*Lactobacillus casei*) Accession: WP_004469756.1/GI: 490604736; (subunit GlcF—*Bacillus atrophaeus*) Accession: WP_010789427.1/GI: 498487739; (subunit GlcD—*Bacillus atrophaeus*) Accession: WP_010789426.1/GI: 498487738; (subunit GlcF—*Nitrosospira* sp. APG3) Accession: WP_004178149.1/GI: 490282255; (subunit GlcF—*Nitrosospira* sp. APG3) Accession: WP_004175407.1/GI: 490279470; (subunit GlcE—*Nitrosospira* sp. APG3) Accession: WP_004175406.1/GI: 490279469; (subunit GlcD—*Nitrosospira* sp. APG3) Accession: WP_004175404.1/GI: 490279467; (subunit GlcD—*Lactobacillus plantarum*) Accession: WP_003646405.1/GI: 489742349; (subunit GlcD—*Lactobacillus casei*) Accession: WP_003605020.1/GI: 489700883; (subunit GlcD—*Lactobacillus casei*) Accession: WP_003591621.1/GI: 489687412; (subunit GlcD—*Lactobacillus casei*) Accession: WP_003576201.1/GI: 489671946; (subunit GlcD—*Pseudomonas aeruginosa*) Accession: WP_003162880.1/GI: 489254909; (subunit GlcD—*Cystobacter fuscus*) Accession: WP_002627940.1/GI: 488703965; (subunit GlcF—*Grimontia* sp. AK16) Accession: WP_002536222.1/GI: 488492778; (subunit GlcE—*Grimontia* sp. AK16) Accession: WP_002536220.1/GI: 488492776; (subunit GlcD—*Grimontia* sp. AK16) Accession: WP_002536218.1/GI: 488492774; (subunit GlcF—*Grimontia* sp. AK16) Accession: EOD81473.1/GI: 486374710; (subunit GlcE—*Grimontia* sp. AK16) Accession: EOD81472.1/GI: 486374709; (subunit GlcD—*Grimontia* sp. AK16) Accession: EOD81471.1/GI: 486374708; (subunit GlcF—*Bacillus atrophaeus* UCMB-5137) Accession: EOB36005.1/GI: 485131200; (subunit GlcD—*Bacillus atrophaeus* UCMB-5137) Accession: EOB36004.1/GI: 485131199; (subunit GlcD—*Clostridiaceae bacterium* L21-TH-D2) Accession: EOD00877.1/GI: 485596261; (subunit GlcE—*Herbaspirillum frisingense* GSF30) Accession: EOA03090.1/GI: 481868141; (subunit GlcD—*Pseudomonas aeruginosa* 18A) Accession: CCQ87198.1/GI: 451755860; (subunit GlcD—*Lactobacillus plantarum* UCMA 3037) Accession: EMP43043.1/GI: 468443300; (subunit GlcF—*Pseudomonas savastanoi* pv. *savastanoi* NCPPB 3335) Accession: EFH98862.1/GI: 298157783; (subunit GlcE—*Pseudomonas savastanoi* pv. *savastanoi* NCPPB 3335) Accession: EFH98861.1/GI: 298157782; (subunit GlcD—*Pseudomonas savastanoi* pv. *savastanoi* NCPPB 3335) Accession: EFH98860.1/GI: 298157781; (subunit GlcD—*Amycolatopsis azurea* DSM 43854) Accession: EMD29767.1/GI: 449424468; (subunit GlcD—*Amycolatopsis azurea* DSM 43854) Accession: EMD25329.1/GI: 449419808; (subunit GlcD—*Rhodobacter* sp. AKP1) Accession: EKX58087.1/GI: 428189534; (subunit GlcE—*Rhodobacter* sp. AKP1) Accession: EKX58086.1/GI: 428189533; (subunit GlcF—*Rhodobacter* sp. AKP1) Accession: EKX58085.1/GI: 428189532; (subunit GlcF—*Caenispirillum salinarum* AK4) Accession: EKV26455.1/GI: 425877724; (subunit GlcE—*Caenispirillum salinarum* AK4) Accession: EKV26454.1/GI: 425877723; (subunit GlcD—*Caenispirillum salinarum* AK4) Accession: EKV26453.1/GI: 425877722; (subunit GlcD—*Lactobacillus rhamnosus* LRHMDP2) Accession: EKS50474.1/GI: 411183335; (subunit GlcD—*Lactobacillus rhamnosus* LRHMDP3) Accession: EKS48724.1/GI: 411181555; (subunit GlcD—*Lactobacillus casei* Lpc-37) Accession: EKQ29053.1/GI: 410555090; (subunit GlcD—*Lactobacillus casei* Lc-10) Accession: EKQ27271.1/GI: 410553268; (subunit GlcD—*Lactobacillus casei* UW4) Accession: EKQ19867.1/GI: 410545576; (subunit GlcD—*Lactobacillus casei* UW1) Accession: EKQ19363.1/GI: 410545055; (subunit GlcD family (*Lactobacillus casei* UCD174) Accession: EKQ17333.1/GI: 410542932; (subunit GlcD—*Lactobacillus casei* T71499) Accession: EKQ12735.1/GI: 410538178; (subunit GlcD—*Lactobacillus casei* A2-362) Accession: EKQ08992.1/GI: 410534338; (subunit GlcD—*Lactobacillus casei* M36) Accession: EKQ08475.1/GI: 410533809; (subunit GlcD—*Lactobacillus casei* CRF28) Accession: EKQ05619.1/GI: 410530856; (subunit GlcD—*Lactobacillus casei* 21/1) Accession: EKQ00611.1/GI: 410525713; (subunit GlcD—*Lactobacillus casei* 32G) Accession: EKP97870.1/GI: 410522932; (subunit GlcD—*Rhodovulum* sp. PH10) Accession: EJW11438.1/GI: 402499743; (subunit GlcE—*Rhodovulum* sp. PH10) Accession: EJW11437.1/GI: 402499742; (subunit GlcF—*Rhodovulum* sp. PH10) Accession: EJW11435.1/GI: 402499740; (subunit GlcD—*Lactococcus raffinolactis* 4877) Accession: CCK18617.1/GI:

399207544; (subunit GlcD—*Lactobacillus pentosus* KCA1) Accession: EIW15038.1/GI: 392437148; (subunit GlcE—*Methylacidiphilum fumariolicum* SolV) Accession: CCG91738.1/GI: 384526958; (subunit GlcF—*Methylacidiphilum fumariolicum* SolV) Accession: CCG91737.1/GI: 384526957; (subunit GlcF—*Methylacidiphilum fumariolicum* SolV) Accession: CCG92195.1/GI: 384526449; (subunit GlcD—*Methylacidiphilum fumariolicum* SolV) Accession: CCG92194.1/GI: 384526448; (subunit GlcD—*Lactobacillus plantarum* WCFS1) Accession: CCC77816.1/GI: 342240582; (subunit GlcD—*Lactobacillus plantarum* subsp. *plantarum* NC8) Accession: EHS83950.1/GI: 376010625; (subunit GlcD—*Burkholderia cenocepacia* H111) Accession: CCE46351.1/GI: 358076106; (subunit GlcF—*Burkholderia cenocepacia* H111) Accession: CCE51249.1/GI: 358071291; (subunit GlcE—*Burkholderia cenocepacia* H111) Accession: CCE51248.1/GI: 358071290; (subunit GlcD—*Burkholderia cenocepacia* H111) Accession: CCE51247.1/GI: 358071289; (subunit GlcE—*Crocosphaera watsonii* WH 0003) Accession: EHJ14361.1/GI: 357265620; (subunit GlcF—*Crocosphaera watsonii* WH 0003) Accession: EHJ14350.1/GI: 357265608; (subunit GlcD—*Crocosphaera watsonii* WH 0003) Accession: EHJ10223.1/GI: 357260887; (subunit GlcE—endosymbiont of *Riftia pachyptila* (vent Ph05)) Accession: EGV51965.1/GI: 344225612; (subunit GlcF—endosymbiont of *Riftia pachyptila* (vent Ph05)) Accession: EGV51964.1/GI: 344225611; (subunit GlcD—*Escherichia coli* EC4100B) Accession: EFW76461.1/GI: 320201886; (subunit GlcE—*Escherichia coli* EC4100B) Accession: EFW76460.1/GI: 320201885; (subunit GlcF—*Escherichia coli* EC4100B) Accession: EFW76459.1/GI: 320201884; (subunit GlcD—*Escherichia coli* WV 060327) Accession: EFW69751.1/GI: 320195122; (subunit GlcE—*Escherichia coli* WV 060327) Accession: EFW69750.1/GI: 320195121; (subunit GlcF—*Escherichia coli* WV 060327) Accession: EFW69749.1/GI: 320195120; (subunit GlcF—*Shigella boydii* ATCC 9905) Accession: EFW55921.1/GI: 320181000; (subunit GlcE—*Shigella boydii* ATCC 9905) Accession: EFW55920.1/GI: 320180999; (subunit GlcD—*Shigella boydii* ATCC 9905) Accession: EFW55919.1/GI: 320180998; (subunit GlcD—*Shigella boydii* ATCC 9905) Accession: EFW55918.1/GI: 320180997; (subunit GlcD—*Pseudomonas fluorescens* F113) Accession: AEV61992.1/GI: 359759913; (subunit GlcE—*Pseudomonas fluorescens* F113) Accession: AEV61991.1/GI: 359759912; (subunit GlcF—*Pseudomonas fluorescens* F113) Accession: AEV61990.1/GI: 359759911; (subunit GlcE—*Escherichia coli* A35218R) Accession: ESE33291.1/GI: 553718318; (subunit GlcF—*Escherichia coli* A35218R) Accession: ESE33290.1/GI: 553718317; (subunit GlcF—*Escherichia coli* A25922R) Accession: ESE30344.1/GI: 553715255; (subunit GlcE—*Escherichia coli* A25922R) Accession: ESE30343.1/GI: 553715254; (subunit GlcF—*Escherichia coli* 908691) Accession: ESE21639.1/GI: 553706155; (subunit GlcE—*Escherichia coli* 908691) Accession: ESE21638.1/GI: 553706154; (subunit GlcE—*Escherichia coli* 910096-2) Accession: ESE18833.1/GI: 553703214; (subunit GlcF—*Escherichia coli* 910096-2) Accession: ESE18831.1/GI: 553703212; (subunit GlcF—*Escherichia coli* 908675) Accession: ESE17737.1/GI: 553702096; (subunit GlcE—*Escherichia coli* 908675) Accession: ESE17736.1/GI: 553702095; (subunit GlcF—*Escherichia coli* 908632) Accession: ESE05561.1/GI: 553689341; (subunit GlcE—*Escherichia coli* 908632) Accession: ESE05560.1/GI: 553689340; (subunit GlcF—*Escherichia coli* 908624) Accession: ESD97562.1/GI: 553680913; (subunit GlcE—*Escherichia coli* 908624) Accession: ESD97561.1/GI: 553680912; (subunit GlcF—*Escherichia coli* 908616) Accession: ESD86368.1/GI: 553669064; (subunit GlcE—*Escherichia coli* 908616) Accession: ESD86367.1/GI: 553669063; (subunit GlcF—*Escherichia coli* 908573) Accession: ESD77743.1/GI: 553659862; (subunit GlcE—*Escherichia coli* 908573) Accession: ESD77742.1/GI: 553659861; (subunit GlcF—*Escherichia coli* 908524) Accession: ESD50621.1/GI: 553631397; (subunit GlcE—*Escherichia coli* 908524) Accession: ESD50620.1/GI: 553631396; (subunit GlcE—*Escherichia coli* 907889) Accession: ESD41111.1/GI: 553621475; (subunit GlcF—*Escherichia coli* 907889) Accession: ESD41110.1/GI: 553621474; (subunit GlcF—*Escherichia coli* 907892) Accession: ESD39087.1/GI: 553619321; (subunit GlcE—*Escherichia coli* 907892) Accession: ESD39086.1/GI: 553619320; (subunit GlcE—*Escherichia coli* 908519) Accession: ESD37595.1/GI: 553617775; (subunit GlcF—*Escherichia coli* 908519) Accession: ESD37594.1/GI: 553617774; (subunit GlcF—*Escherichia coli* 907391) Accession: ESC99480.1/GI: 553577909; (subunit GlcE—*Escherichia coli* 907391) Accession: ESC99479.1/GI: 553577908; (subunit GlcE—*Escherichia coli* 907779) Accession: ESA94412.1/GI: 553367942; (subunit GlcF—*Escherichia coli* 907779) Accession: ESA94411.1/GI: 553367941; (subunit GlcF—*Escherichia coli* 113290) Accession: ESA73887.1/GI: 553346580; (subunit GlcE—*Escherichia coli* 113290) Accession: ESA73885.1/GI: 553346578; (subunit GlcD—*Pseudomonas fluorescens* F113) Accession: YP_005207387.1/GI: 378949899; (subunit GlcE—*Pseudomonas fluorescens* F113) Accession: YP_005207386.1/GI: 378949898; (subunit GlcF—*Pseudomonas fluorescens* F113) Accession: YP_005207385.1/GI: 378949897.

The invention may also use variants of the glycolate dehydrogenase polypeptide(s) herein described. Variants include, but are not limited to, deletions, additions, substitutions, insertions of e.g. 1 to 20 amino acids, such as 1 to 10, or 1 to 5). Generally, amino acid sequence variants of glycolate dehydrogenase polypeptide(s) described herein will have at least 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% sequence identity to the amino acid sequences of the glycolate dehydrogenases explicitly described herein, and will retain glycolate dehydrogenase activity. Variant glycolate dehydrogenase may have at least 60% sequence identity to the amino acid sequence of SEQ ID No 6. Variant glycolate dehydrogenase may have at least 60% sequence identity to the amino acid sequence of SEQ ID No 9. Variant glycolate dehydrogenase may have at least 60% sequence identity to the amino acid sequence of SEQ ID No 3, 4 and 5. Variant glycolate dehydrogenase may have at least 95% sequence identity to the amino acid sequence of SEQ ID No 6. Variant glycolate dehydrogenase may have at least 95% sequence identity to the amino acid sequence of SEQ ID No 9. Variant glycolate dehydrogenase may have at least 95% sequence identity to the amino acid sequence of SEQ ID No 3, 4 and 5. Generally, nucleotide sequence variants have at least 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% sequence identity to the nucleotide sequences encoding the glycolate dehydrogenases described herein, and the encoded products retain glycolate dehydrogenase activity. Variant nucleic acids encoding glycolate dehydrogenase polypeptide(s) may have at least 60% sequence identity to the nucleotide sequence of SEQ ID No 10 from the nucleotide position 3666-6845. Variant nucleic acids encoding glycolate dehydrogenase polypeptide(s) may have at least 95% sequence identity to the nucleotide sequence of SEQ ID No 10 from the nucleotide position 3666-6845.

The nucleic acid molecules encoding glycolate dehydrogenase polypeptide(s) as described herein may be modified, for example, by codon optimization to facilitate expression in heterologous cells, as described elsewhere for SBPases. The glycolate dehydrogenase polypeptide(s) may be linked to chloroplast targeting signals as described elsewhere. The nucleic acids may be linked to regulatory regions as described above, and the nucleic acids may be either inserted in plastid, such as chloroplast genomes, or in the nuclear genome as described above in the context of expression of SBPase polypeptide(s). Each of the embodiments described for SBPase expression should be considered to have been disclosed mutatis mutandis in connection with the glycolate dehydrogenases and encoding nucleotides herein mentioned.

It is expected that the methods of the invention will be suitable for any plant, including for monocotyledonous, dicotyledonous Angiosperm plants, as well as for gymnosperm plants. The methods of the invention will be particularly suitable for crop plants, including wheat, rice, millet, corn, *sorghum*, rye, oats, sugarcane, cotton, soybean or *Brassica* (oilseed) plants including musterd.

Plants according to the invention can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention. The present invention also relates to any products such as meal, oil, fibers etc. which are obtained by processing the plants, parts thereof, or seeds of the invention.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The following non-limiting examples describe the generation of transgenic plants expressing simultaneously glycolate dehydrogenase enzymes and SBPase and the effect on growth, biomass and carbon assimilation.

Unless states otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy R D D (ed.) (1993) Plant Molecular Biology LabFax, BIOS Scientific Publishers Ltd., Oxford and Blackwell Scientific Publications, Oxford" and in "Brown T A, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com".

The sequence listing contained in the file named "BCS14-2011-WO1_ST25.txt", which is 78 kilobytes (size as measured in Microsoft Windows®), contains 12 sequences. SEQ ID NO: 1 through SEQ ID NO: 12 is filed herewith by electronic submission and is incorporated by reference herein.

In the description and examples, reference is made to the following sequences:

SEQ ID 1: nucleotide sequence of the coding sequence of the sedoheptulose 1,7—bisphosphate gene of *Oryza sativa*

SEQ ID 2: amino acid sequence of the SBPase from *Oryza sativa*

SEQ ID 3: amino acid sequence of the GlcD subunit from *Escherichia coli*

SEQ ID 4: amino acid sequence of the GlcE subunit from *Escherichia coli*

SEQ ID 5: amino acid sequence of the GlcD subunit from *Escherichia coli*

SEQ ID 6: amino acid sequence of the *Chlamydomonas rheinhardtii* mature glycolate dehydrogenase SEQ ID 7: amino acid sequence of the *Chlamydomonas rheinhardtii* mature glycolate dehydrogenase (truncated)

SEQ ID 8: amino acid sequence of the *Synechocystis* mature glycolate dehydrogenase SEQ ID 9: amino acid of glycolate dehydrogenase from *Arabidopsis thaliana*

SEQ ID 10: nucleotide sequence of the T-DNA of vector PTCD155

SEQ ID 11: nucleotide sequence of the T-DNA of vector PTMV548

SEQ ID 12: nucleotide sequence of the T-DNA of vector PTCD163

EXAMPLES

Example 1. Effect of Combined Expression of SPBase and Glycolate Dehydrogenase in *Arabidopsis thaliana*

*Arabidopsis thaliana* plants comprising a recombinant gene encoding glycolate dehydrogenase from *Chlamydomonas rheinhardtii*, as described in WO2010/012796, were crossed with *Arabidopsis thaliana* plants comprising a recombinant gene encoding SBPase/FBPase (as described in Miyagawa et al. 2001, supra) and progeny plants comprising both chimeric genes were selected.

Plants comprising both transgenes encoding glycolatedehydrogenase GDH and SBPase were compared to plant that only contain one transgene encoding GDH or only SBPase. In a first experiment, whereby plants were grown under light levels of approximately 120 µE, an increase of 5% in rosette diameter, 10% in fresh weight and 11% in dry weight was observed.

TABLE 1A

| Genotype | AV rosette (cm) | SE | Av Fresh weight (g) | SE | Av dry weight (g) | SE |
|---|---|---|---|---|---|---|
| GDH/SBPase | 12.52 | 0.2384 | 1.49 | 0.0711 | 0.098 | 2.4 |
| GDH only or SBPase only | 11.90 | 0.3894 | 1.36 | 0.0941 | 0.088 | 3.6 |
| Ttest | 0.157 | | 0.244 | | 0.23 | |
| % increase | 5.19 | | 10.01 | | 11 | |

In a second experiment, whereby plants were grown under light levels of approximately 120 µE, an increase of 4% in rosette diameter, 11% in fresh weight and 7% in dry weight was observed.

TABLE 1B

| Genotype | AV rosette (cm) | SE | Av Fresh weight (g) | SE | Av dry weight (g) | SE |
|---|---|---|---|---|---|---|
| GDH/SBPase | 12.5 | 0.2 | 2.0 | 0.1 | 0.15 | 0.0 |
| GDH only or SBPase only | 12.0 | 0.2 | 1.7 | 0.1 | 0.14 | 0.0 |
| Ttest | 0.1 | | 0.1 | | 0.3 | |
| % increase | 4.2 | | 11.0 | | 6.9 | |

In a third experiment, plants were grown under higher light levels of approximately 250 µE. No positive impact on growth was observed in this experiment.

Example 2. Effect of Combined Expression of SBPase and Glycolate Dehydrogenase in Wheat Using conventional recombinant gene techniques, a recombinant gene encoding glycolate dehydrogenase under control of a rice Rubisco small subunit promoter was constructed by operably linking the following DNA regions:
a. A DNA region having a sequence including the promoter region of the ribulosebisphosphate carboxylase small subunit gene of *Oryza sativa* (rice) (Nomura et al., 2000) (SEQ ID No 10 between nucleotides 75-2824)
b. A DNA region coding for the first intron of the Actin 1 gene of *Oryza sativa* (rice) (Mc Elroy et al., 1990). (SEQ ID No 10 between nucleotides 2825-3293)
c. A DNA region encoding the optimized transit peptide, containing sequence of the RuBisCO small subunit genes of *Zea mays* (corn) and *Helianthus annuus* (sunflower) (Lebrun et al., 1996), adapted to wheat codon usage (SEQ ID No 10 between nucleotides 3294-3665)
d. A DNA region encoding the mature part of the glycolate dehydrogenase gene of *Chlamydomonas reinhardtii* (Nakamura et al., 2005), adapted to wheat codon usage (SEQ ID No 10 between nucleotides 3666-6845)
e. A DNA region sequence including the 3' untranslated region of the nopaline synthase gene from the T-DNA of pTiT37 (Depicker et al., 1982) (SEQ ID No 10 between nucleotides 6846-7143)

Using conventional recombinant gene techniques, a recombinant gene encoding glycolate dehydrogenase under control of a rice fructose 1,6 bisphosphatase gene promoter was constructed by operably linking the following DNA regions:
a. A DNA region having a sequence including the promoter region of the fructose 1,6 bisphosphatase gene of *Oryza sativa* (rice) (Si et al., 2003) (SEQ ID No 11 between nucleotides 75-1272)
b. A DNA region coding for the first intron of the Actin 1 gene of *Oryza sativa* (rice) (Mc Elroy et al., 1990). (SEQ ID No 11 between nucleotides 1273-1741)
c. A DNA region encoding the optimized transit peptide, containing sequence of the RuBisCO small subunit genes of *Zea mays* (corn) and *Helianthus annuus* (sunflower) (Lebrun et al., 1996), adapted to wheat codon usage (SEQ ID No 11 between nucleotides 1742-2113)
d. A DNA region encoding the mature part of the glycolate dehydrogenase gene of *Chlamydomonas reinhardtii* (Nakamura et al., 2005), adapted to wheat codon usage (SEQ ID No 11 between nucleotides 2114-5293)
e. A DNA region sequence including the 3' untranslated region of the nopaline synthase gene from the T-DNA of pTiT37 (Depicker et al., 1982) (SEQ ID No 11 between nucleotides 5294-5591)

Using conventional recombinant gene techniques, a recombinant gene encoding SBPase under control of a rice RuBisCO small subunit gene promoter was constructed by operably linking the following DNA regions:
a. A DNA region having a the promoter region of the ribulosebisphosphate carboxylase small subunit gene of *Oryza sativa* (rice) (Nomura et al., 2000) (SEQ ID No 12 between nucleotides 2010-4759 counter clockwise)
b. A DNA region coding for the first intron of the actin 1 gene of *Oryza sativa* (rice) (Mc Elroy et al., 1990). (SEQ ID No 12 between nucleotides 1541-2009 counter clockwise)
c. A DNA region encoding coding sequence of the sedoheptulose-1,7-bisphosphatase gene of *Oryza sativa* (rice) (Feng et al., 2007) (SEQ ID No 12 between nucleotides 362-1540)
d. A DNA region sequence including the 3' untranslated region of the octopine synthase gene of *Agrobacterium* (De Greve et al 1982) (SEQ ID No 12 between nucleotides 26-361 counter clockwise).

The recombinant gene encoding glycolate dehydrogenase under control of a rice RuBisCO small subunit promoter was combined with the glufosinate tolerance gene (bar) as selectable marker and cloned between the T-DNA borders of pTCD155. The nucleotide sequence of the T-DNA of this vector is included in the sequence listing as SEQ ID No 10. A list of the features of this sequence is included as Table 2.

In a similar manner, the recombinant gene encoding glycolate dehydrogenase under control of a rice fructose 1,6 bisphosphatase gene promoter was combined with the glufosinate tolerance gene (bar) as selectable marker and cloned between the T-DNA borders of pTMV548. The nucleotide sequence of the T-DNA of this vector is included in the sequence listing as SEQ ID No 11. A list of the features of this sequence is included as Table 3.

In addition, the recombinant gene encoding SBPase under control of a rice Rubisco small subunit promoter was combined with recombinant gene encoding glycolate dehydrogenase under control of a rice RuBisCo small subunit promoter and the glufosinate tolerance gene (bar) as selectable marker and cloned between the T-DNA borders of pTCD163. The nucleotide sequence of the T-DNA of this vector is included in the sequence listing as SEQ ID No 12. A list of the features of this sequence is included as Table 4.

The T-DNA vectors were introduced into *Agrobacterium tumefaciens* comprising a helper Ti-plasmid and the resulting strains were used to generate transgenic wheat plants, according to the method described in WO2011/013764.

Transgenic wheat plants are assayed for biomass production, seed yield and $CO_2$ assimilation. Wheat plants expressing both SBPase and glycolate dehydrogenase have an increased biomass (dry weight), increased seed yield and increased $CO_2$ assimilation when compared to transgenic wheat plant expression only glycolate dehydrogenase.

TABLE 2

Description of the genetic elements of pTCD155.

| Nucleotide positions | Orientation | Description |
|---|---|---|
| 1-25 | | RB: right border repeat from the T-DNA of *Agrobacterium tumefaciens* (Zambryski, 1988) |
| 75-2824 | Clockwise | PrbcSOs: sequence including the promoter region of the ribulosebisphosphate carboxylase small subunit gene of *Oryza sativa* (rice) (Nomura et al., 2000) |
| 2825-3293 | Clockwise | intron_act1Os: first intron of the actin 1 gene of *Oryza sativa* (rice) (Mc Elroy et al., 1990). |
| 3294-3665 | Clockwise | TPotpC-1Pm: coding sequence of the optimized transit peptide, containing sequence of the RuBisCO small subunit genes of *Zea mays* (corn) and *Helianthus annuus* (sunflower) (Lebrun et al., 1996), adapted to wheat codon usage |
| 3666-6845 | Clockwise | gdhCrh-2Pd: coding sequence of the mature part of the glycolate dehydrogenase gene of *Chlamydomonas reinhardtii* (Nakamura et al., 2005), adapted to wheat codon usage |
| 6846-7143 | Clockwise | 3'nos: sequence including the 3' untranslated region of the nopaline synthase gene from the T-DNA of pTiT37 (Depicker et al., 1982) |
| 7220-8056 | Clockwise | P35S3: sequence including the promoter region of the Cauliflower Mosaic Virus 35S transcript (Odell et al., 1985) |
| 8057-8608 | Clockwise | bar: coding sequence of the phosphinothricin acetyltransferase gene of *Streptomyces hygroscopicus* (Thompson et al., 1987). |
| 8609-8892 | Clockwise | 3'nos: sequence including the 3' untranslated region of the nopaline synthase gene from the T-DNA of pTiT37 (Depicker et al., 1982) |
| 8989-9013 | | LB: left border repeat from the T-DNA of *Agrobacterium tumefaciens* (Zambryski, 1988) |

TABLE 3

Description of the genetic elements of pTMV548.

| Nucleotide positions | Orientation | Description |
|---|---|---|
| 1-25 | | RB: right border repeat from the T-DNA of *Agrobacterium tumefaciens* (Zambryski, 1988 |
| 75-1272 | Clockwise | Pfbp1Os: sequence including the promoter region of the cytosolic fructose-1,6-bisphosphatase gene of *Oryza sativa* (Si et al., 2003) |
| 1273-1741 | Clockwise | intron_act1Os: first intron of the actin 1 gene of *Oryza sativa* (rice) (Mc Elroy et al., 1990). |
| 1742-2113 | Clockwise | TPotpC-1Pm: coding sequence of the optimized transit peptide, containing sequence of the RuBisCO small subunit genes of *Zea mays* (corn) and *Helianthus annuus* (sunflower) (Lebrun et al., 1996), adapted to wheat codon usage |
| 2114-5293 | Clockwise | gdhCrh-2Pd: coding sequence of the mature part of the glycolate dehydrogenase gene of *Chlamydomonas reinhardtii* (Nakamura et al., 2005), adapted to wheat codon usage |
| 5294-5591 | Clockwise | Tnos: sequence including the 3' untranslated region of the nopaline synthase gene from the T-DNA of pTiT37 (Depicker et al., 1982) |
| 5668-6504 | Clockwise | 5668-6504 Clockwise P35S3: sequence including the promoter region of the Cauliflower Mosaic Virus 35S transcript (Odell et al., 1985) |
| 6505-7056 | Clockwise | bar: coding sequence of the phosphinothricin acetyltransferase gene of *Streptomyces hygroscopicus* (Thompson et al., 1987). |
| 7057-7340 | Clockwise | Tnos: sequence including the 3' untranslated region of the nopaline synthase gene from the T-DNA of pTiT37 (Depicker et al., 1982) |

TABLE 3-continued

Description of the genetic elements of pTMV548.

| Nucleotide positions | Orientation | Description |
|---|---|---|
| 7437-7461 | | LB: left border repeat from the T-DNA of *Agrobacterium tumefaciens* (Zambryski, 1988) |

TABLE 4

Description of the genetic elements of pTCD163.

| Nt positions | Orientation | Description |
|---|---|---|
| 1-25 | | RB: right border repeat from the T-DNA of *Agrobacterium tumefaciens* (Zambryski, 1988) |
| 26-361 | Counter Clockwise | 3'ocs: sequence including the 3' untranslated region of the octopine synthase gene of *Agrobacterium tumefaciens* (De Greve et al., 1982) |
| 362-1540 | Counter Clockwise | sbpaseOs-1Pa: coding sequence of the sedoheptulose-1,7-bisphosphatase gene of *Oryza sativa* (rice) (Feng et al., 2007) |
| 1541-2009 | Counter Clockwise | intron_act1Os: first intron of the actin 1 gene of *Oryza sativa* (rice) (Mc Elroy et al., 1990). |
| 2010-4759 | Counter Clockwise | PrbcSOs: sequence including the promoter region of the ribulosebisphosphate carboxylase small subunit gene of *Oryza sativa* (rice) (Nomura et al., 2000) |
| 4760-4959 | Counter clockwise | 3'35S: sequence including the 3' untranslated region of the 35S transcript of the Cauliflower Mosaic Virus (Sanfacon et al., 1991) |
| 4960-7733 | Clockwise | PrbcSOs: sequence including the promoter region of the ribulosebisphosphate carboxylase small subunit gene of *Oryza sativa* (rice) (Nomura et al., 2000) |
| 7734-8202 | Clockwise | intron_act1Os: first intron of the actin 1 gene of *Oryza sativa* (rice) (Mc Elroy et al., 1990). |
| 8203-8574 | Clockwise | TPotpC-1Pm: coding sequence of the optimized transit peptide, containing sequence of the RuBisCO small subunit genes of *Zea mays* (corn) and *Helianthus annuus* (sunflower) (Lebrun et al., 1996), adapted to wheat codon usage |
| 8575-11754 | Clockwise | gdhCrh-2Pd: coding sequence of the mature part of the glycolate dehydrogenase gene of *Chlamydomonas reinhardtii* (Nakamura et al., 2005), adapted to wheat codon usage |
| 11755-12052 | Clockwise | 3'nos: sequence including the 3' untranslated region of the nopaline synthase gene from the T-DNA of pTiT37 (Depicker et al., 1982) |
| 12129-12965 | Clockwise | P35S3: sequence including the promoter region of the Cauliflower Mosaic Virus 35S transcript (Odell et al., 1985) |
| 12966-13517 | Clockwise | bar: coding sequence of the phosphinothricin acetyltransferase gene of *Streptomyces hygroscopicus* (Thompson et al., 1987). |
| 13518-13801 | Clockwise | 3'nos: sequence including the 3' untranslated region of the nopaline synthase gene from the T-DNA of pTiT37 (Depicker et al., 1982) |
| 13898-13922 | | LB: left border repeat from the T-DNA of *Agrobacterium tumefaciens* (Zambryski, 1988) |

REFERENCES

Carrington & Freed 1990 Journal of Virology 64(4): 1590-1597
Christou et al., 1991 Plant Mol Biol. 35(1-2): 197-203
Clemente et al, 2000 Crop Sci. 40:797
De Greve et al., 1982 Journal of Molecular and Applied Genetics 1: 499-511
de Pater et al., 1992 Plant J. 2:837-844
Depicker et al., 1982 Journal of Molecular and Applied Genetics, 1: 561-573
Droste et al, 2002 Euphytica. 2002; 127:367-376
Feng et al., 2007 Plant Cell Rep 26: 1635-1646
Hiei et al., 1994 The Plant Journal 6(2): 271-282
Hiei et al., 1997 Plant Mol Biol. 35: 205-218
Kyozuka J. et al., 1993 Plant Physiology 102: 991-1000
Lebrun et al., 1996 U.S. Pat. No. 5,510,471
Maughan et al, 1999 In Vitro Cell. Dev. Biol Plant. 1999; 35:344-349
McElroy D. et al., 1990 The Plant Cell, 2: 163-171
Nakamura et al., 2005 Canadian Journal of Botany, 83: 820-833
Nomura et al., 2000 Plant Molecular Biology, 44(1): 99-106
Odell et al., 1985 Nature, 313: 810-812
Olhoft & Somers, 2001 Plant Cell Rep, 20: 706-711
Olhoft et al, 2001 Plant Cell Rep, 20: 731-737
Sanfaçon et al., 1991 Genes and Development 5: 141-149

Santarem & Finer, 1999 In Vitro Cellular and Developmental Biology—Plant. 35:451-455
Si et al., 2003 Acta Botanica Sinica, 45(3): 359-364
Thompson et al., 1987 EMBO Journal, 6: 2519-2523
Trick & Finer, 1998 In Vitro Cellular and Developmental Biology—Plant 35:57-60
Zambryski, 1988 Annual Review of Genetics, 22: 1-30
Zhang et al, 1999 Plant Cell Tiss. Organ Cult. 56:37

The invention claimed is:

1. A method for improving the assimilation of carbon in a plant comprising the steps of:
   a. inserting into the genome of a plant a nucleic acid encoding an enzyme comprising sedoheptulose 1,7-bisphosphatase activity operably linked to a plant-expressible promoter, and optionally to a 3' end region involved in transcription termination and/or polyadenylation, wherein said enzyme comprising sedoheptulose 1,7-bisphosphatase activity comprises an amino acid sequence having at least 95% identity to the amino acid sequence of SEQ ID No. 2; and
   b. inserting into the genome of said plant one or more nucleic acids encoding one or more polypeptides having the enzymatic activity of glycolate dehydrogenase operably linked to a plant-expressible promoter, and optionally to a 3' end region involved in transcription termination and/or polyadenylation, wherein said one or more polypeptides are located in chloroplasts of said plants.

2. The method of claim 1, wherein said enzyme comprising sedoheptulose 1,7-bisphosphatase activity further comprises FBPase activity or is from a source heterologous with respect to the plant into which the nucleic acid is inserted.

3. The method of claim 1, wherein said enzyme comprising sedoheptulose 1,7-bisphosphatase activity comprises the amino acid sequence of SEQ ID No. 2.

4. The method of claim 3, wherein said enzyme comprising sedoheptulose 1,7-bisphosphatase activity is encoded by a nucleic acid comprising the nucleotide sequence of SEQ ID No. 1.

5. The method according to claim 1, wherein said promoter includes the promoter region of the ribulose-bisphosphate carboxylase small subunit gene of *Oryza sativa*.

6. The method according to claim 5, wherein said promoter comprises the complement of the nucleotide sequence of SEQ ID No. 12 from nucleotide position 2010 to 4759.

7. The method according to claim 1, wherein said enzyme comprising sedoheptulose 1,7-bisphosphatase activity further comprises an amino acid sequence targeting said enzyme comprising sedoheptulose 1,7-bisphosphatase activity to the chloroplast or the chloroplast membrane or wherein said nucleic acid encoding an enzyme comprising sedoheptulose 1,7-bisphosphatase activity is integrated in the chloroplast genome of cells of said plant.

8. The method according to claim 1, wherein said one or more polypeptides having the enzymatic activity of a glycolate dehydrogenase are derived from the *E. coli* glc operon or wherein said one or more polypeptides having the enzymatic activity of a glycolate dehydrogenase is a *Chlamydomonas* or *Synechocystis* glycolate dehydrogenase or wherein said one or more polypeptides having the enzymatic activity of a glycolate dehydrogenase is an *Arabidopsis* glycolate dehydrogenase.

9. The method according to claim 8, wherein said one or more polypeptides comprise an amino acid sequence having at least 95% sequence identity to the amino acid sequence of SEQ ID No. 3, SEQ ID No. 4 and SEQ ID No. 5 or to the amino acid sequence of SEQ ID No. 6, SEQ ID No. 7 or SEQ ID No. 8 or to the amino acid sequence of SEQ ID No. 9.

10. The method according to claim 8, wherein said polypeptides form a multi-subunit fusion protein.

11. The method according to claim 1, wherein said one or more polypeptides having glycolate dehydrogenase activity further comprise an amino acid sequence targeting said enzyme to the chloroplast or the chloroplast membrane or wherein said one or more nucleic acids encoding one or more polypeptides having glycolate dehydrogenase activity are integrated in the chloroplast genome of cells of said plant.

12. The method according to claim 1, wherein said promoter includes the promoter region of the cytosolic fructose 1,6 bisphosphatase gene of *Oryza sativa*.

13. The method according to claim 12, wherein said promoter comprises the nucleotide sequence of SEQ ID No. 11 from nucleotide position 75 to 1272.

14. The method according to claim 1, wherein said plant is a monocotyledonous plant or a dicotyledonous plant or a Gymnosperm.

15. The method according to claim 14, wherein said plant is selected from wheat, rice, maize, *sorghum*, millet, rye, oats, sugarcane, cotton, soybean or a *Brassica* plant.

16. A plant cell, a plant part, a plant or a seed comprising in its genome a nucleic acid encoding an enzyme comprising sedoheptulose 1,7-bisphosphatase activity operably linked to a plant-expressible promoter, and optionally to a 3' end region involved in transcription termination and/or polyadenylation; and one or more nucleic acids encoding one or more polypeptides having the enzymatic activity of glycolate dehydrogenase operably linked to a plant-expressible promoter, and optionally to a 3' end region involved in transcription termination and/or polyadenylation, wherein said enzyme comprising sedoheptulose 1,7-bisphosphatase activity comprises an amino acid sequence having at least 95% identity to the amino acid sequence of SEQ ID No. 2, and wherein said one or more polypeptides are located in chloroplasts of said plants.

17. The plant cell, a plant part, a plant or a seed of claim 16, wherein said enzyme comprising sedoheptulose 1,7-bisphosphates activity further comprises FBPase activity or is from a source heterologous with respect to the plant into which the nucleic acid is inserted.

18. The plant cell, a plant part, a plant or a seed of claim 16, wherein said enzyme comprising sedoheptulose 1,7-bisphosphatase activity comprises the amino acid sequence of SEQ ID No. 2.

19. The plant cell, a plant part, a plant or a seed of claim 18, wherein said enzyme comprising sedoheptulose 1,7-bisphosphatase activity is encoded by a nucleic acid comprising the nucleotide sequence of SEQ ID No. 1.

20. The plant cell, a plant part, a plant or a seed of claim 16, wherein said promoter includes the promoter region of the ribulose-bisphosphate carboxylase small subunit gene of *Oryza sativa*.

21. The plant cell, a plant part, a plant or a seed of claim 20, wherein said promoter comprises the complement of the nucleotide sequence of SEQ ID No. 12 from nucleotide position 2010 to 4759.

22. The plant cell, a plant part, a plant or a seed according to claim 16, wherein said enzyme comprising sedoheptulose 1,7-bisphosphatase activity further comprises an amino acid sequence targeting said enzyme comprising sedoheptulose 1,7-bisphosphatase activity to the chloroplast or the chloroplast membrane or wherein said nucleic acid encoding an enzyme comprising sedoheptulose 1,7-bisphosphatase activity is integrated in the chloroplast genome of cells of said plant.

23. The plant cell, a plant part, a plant or a seed according to claim 16, wherein said one or more polypeptides having the enzymatic activity of a glycolate dehydrogenase are derived from the *E. coli* glc operon or wherein said one or more polypeptides having the enzymatic activity of a glycolate dehydrogenase is a *Chlamydomonas* or *Synechocystis* glycolate dehydrogenase or wherein said one or more polypeptides having the enzymatic activity of a glycolate dehydrogenase is an *Arabidopsis* glycolate dehydrogenase.

24. The plant cell, a plant part, a plant or a seed according to claim 23, wherein said one or more polypeptides comprise an amino acid sequence having at least 95% sequence identity to the amino acid sequence of SEQ ID No. 3, SEQ ID No. 4 and SEQ ID No. 5 or to the amino acid sequence of SEQ ID No. 6, SEQ ID No. 7 or SEQ ID No. 8 or to the amino acid sequence of SEQ ID No. 9.

25. The plant cell, a plant part, a plant or a seed according claim 23, wherein said polypeptides form a multi-subunit fusion protein.

26. The plant cell, a plant part, a plant or a seed according to claim 16, wherein said one or more polypeptides having glycolate dehydrogenase activity further comprise an amino acid sequence targeting said enzyme to the chloroplast or the chloroplast membrane or wherein said one or more nucleic acids encoding one or more polypeptides having glycolate dehydrogenase activity are integrated in the chloroplast genome of cells of said plant.

27. The plant cell, a plant part, a plant or a seed according to claim 16, wherein said promoter includes the promoter region of the ribulose-bisphosphate carboxylase small subunit gene of *Oryza sativa* or the promoter region of the cytosolic fructose 1,6 bisphosphatase gene of *Oryza sativa*.

28. The plant cell, a plant part, a plant or a seed according to claim 27, wherein said promoter comprises the complement of the nucleotide sequence of SEQ ID No. 12 from nucleotide position 2010 to 4759 or the nucleotide sequence of SEQ ID No. 11 from nucleotide position 75 to 1272.

29. The plant cell, a plant part, a plant or a seed according to claim 16, wherein said plant is a monocotyledonous plant or a dicotyledonous plant or a Gymnosperm.

30. The plant cell, a plant part, a plant or a seed according to claim 29, wherein said plant is selected from wheat, rice, maize, *sorghum*, millet, rye, oats, sugarcane, cotton, soybean or a *Brassica* plant.

31. A method for improving the assimilation of carbon in a plant or for increasing the growth rate or improving the biomass production of a plant, said method comprising the steps of inserting into the genome of a plant
   a. a nucleic acid encoding an enzyme comprising sedoheptulose 1,7-bisphosphatase activity operably linked to a plant-expressible promoter, and optionally to a 3' end region involved in transcription termination and/or polyadenylation, wherein said enzyme comprising sedoheptulose 1,7-bisphosphatase activity comprises an amino acid sequence having at least 95% identity to the amino acid sequence of SEQ ID No. 2; and
   b. one or more nucleic acids encoding one or more polypeptides having the enzymatic activity of glycolate dehydrogenase operably linked to a plant-expressible promoter, and optionally to a 3' end region involved in transcription termination and/or polyadenylation, wherein said one or more polypeptides are located in chloroplasts of said plants.

32. The method of claim 1, wherein said enzyme comprising sedoheptulose 1,7-bisphosphatase activity comprises an amino acid sequence having at least 98% identity to the amino acid sequence of SEQ ID No. 2.

33. The method of claim 32, said enzyme comprising sedoheptulose 1,7-bisphosphatase activity comprises the amino acid sequence of SEQ ID No. 2.

* * * * *